(12) United States Patent
Choi et al.

(10) Patent No.: US 11,352,399 B2
(45) Date of Patent: Jun. 7, 2022

(54) PEPTIDE FOR TOLL-LIKE RECEPTOR (TLR) INHIBITION AND PHARMACEUTICAL COMPOSITION COMPRISING SAME

(71) Applicant: GENESEN CO., LTD., Seoul (KR)

(72) Inventors: Sang Dun Choi, Suwon-si (KR); Hyuk Kwon Kwon, Pyeongtaek-si (KR); Hyeon Jun Shin, Suwon-si (KR); Xiang Ai Gui, Suwon-si (KR)

(73) Assignee: GENESEN CO., LTD., Seoul (KR)

( * ) Notice: Subject to any disclaimer, the term of this patent is extended or adjusted under 35 U.S.C. 154(b) by 257 days.

(21) Appl. No.: 16/610,278

(22) PCT Filed: Apr. 25, 2018

(86) PCT No.: PCT/KR2018/004803
§ 371 (c)(1),
(2) Date: Nov. 1, 2019

(87) PCT Pub. No.: WO2018/203613
PCT Pub. Date: Nov. 8, 2018

(65) Prior Publication Data
US 2020/0140504 A1    May 7, 2020

(30) Foreign Application Priority Data

May 4, 2017    (KR) .................. 10-2017-0056842
Apr. 23, 2018    (KR) .................. 10-2018-0046715

(51) Int. Cl.
| | |
|---|---|
| C07K 7/08 | (2006.01) |
| C07K 14/435 | (2006.01) |
| C07K 14/475 | (2006.01) |
| A61K 38/10 | (2006.01) |
| A61K 38/17 | (2006.01) |
| A61K 38/18 | (2006.01) |
| C07K 14/705 | (2006.01) |
| C07K 14/47 | (2006.01) |
| C07K 16/24 | (2006.01) |
| C07K 16/28 | (2006.01) |
| A61K 38/00 | (2006.01) |
| C07K 14/71 | (2006.01) |

(52) U.S. Cl.
CPC .......... *C07K 14/4703* (2013.01); *A61K 38/10* (2013.01); *A61K 38/1767* (2013.01); *A61K 38/18* (2013.01); *C07K 7/08* (2013.01); *C07K 14/43581* (2013.01); *C07K 14/475* (2013.01); *C07K 14/705* (2013.01); *C07K 16/241* (2013.01); *C07K 16/249* (2013.01); *C07K 16/2896* (2013.01); *A61K 38/00* (2013.01); *A61K 38/179* (2013.01); *C07K 14/71* (2013.01); *C07K 2317/73* (2013.01); *C07K 2317/76* (2013.01); *C07K 2319/00* (2013.01); *C07K 2319/10* (2013.01); *C07K 2319/32* (2013.01)

(58) Field of Classification Search
CPC ...... A61K 38/00; A61K 38/177; A61K 38/17; A61K 38/18; A61K 38/08; A61K 38/10; C07K 14/705; C07K 7/08; C07K 7/06; C07K 14/70596; C07K 14/71
See application file for complete search history.

(56) References Cited

U.S. PATENT DOCUMENTS

| | | | |
|---|---|---|---|
| 10,435,443 B2 * | 10/2019 | Choi | ................ A61P 37/00 |
| 2005/0257280 A1 | 11/2005 | Akira | |
| 2010/0069297 A1 * | 3/2010 | Fenton | .............. A61P 29/00 |
| | | | 435/375 |
| 2013/0203649 A1 | 8/2013 | Toshchakov | |
| 2014/0045759 A1 | 2/2014 | Awasthi | |

FOREIGN PATENT DOCUMENTS

JP    2004-73073 A    3/2004

OTHER PUBLICATIONS

Achek et al. Toll-like receptors: promising therapeutic targets for inflammatory diseases. Arch Pharm Res 39: 1032-1049, 2016.*
Cuny, G.D. Neurodegenerative diseases: challenges and opportunities. Future Med Chem 4(13): 1647-1649, 2012.*
El-Zayat et al. Toll-like receptors activation, signaling, and targeting: an overview. Bull Natl Res Centre 43: 187, 2019 (12 total pages).*
Godyn et al. Therapeutic strategies for Alzheimer's dsiease in clincal trials. Pharmacol Reports 68: 127-138, 2016.*
Goh et al. Huntington's disease: neuropsychiatric manifestations of Huntington's disease. Australasian Psychiatry 26(4): 366-375, 2018.*
Herbst et al. Biomarkers for systemic lupus erythematosus. Int J Rheumatic Dis 15: 433-434, 2012.*
Liu et al. TLR2 and TLR4 in autoimmune diseases: a comprehensive review. Clinic Rev Allerg Immunol 47: 136-147, 2014.*
Molteni et al. The role of toll-like receptor 4 in infectious and noninfectious inflammation. Mediators Inflamm 2016: 6978936, 2016.*
Olejnik et al. Toll-like receptor 4 in acute viral infection: too much of a good thing. PLoS Pathog 14(12): e1007390, 2018.*
Park et al. TLR4/MD2 specific peptides stalled in vivo LPS-induced immune exacerbation. Biomaterials 126: 49-60, 2017.*

(Continued)

*Primary Examiner* — Bridget E Bunner
(74) *Attorney, Agent, or Firm* — Sughrue Mion, PLLC

(57) ABSTRACT

The present invention relates to a fusion polypeptide that inhibits TLR1/2, TLR2/6, TLR7, TLR8 and TLR9 signaling pathways as well as Toll-like receptor 4 (TLR4) and TLR3, and a pharmaceutical composition for preventing or treating TLR pathway mediated diseases. The fusion peptide of the present invention has an excellent effect of inhibiting TLR4 and various TLR pathways and can be effectively used in preventing and treating various TLR pathway mediated diseases caused by the signaling pathways, such as autoimmune diseases, inflammatory diseases and degenerative neurological diseases, by inhibiting the TLR mediated immune responses.

13 Claims, 47 Drawing Sheets
(28 of 47 Drawing Sheet(s) Filed in Color)
Specification includes a Sequence Listing.

(56) References Cited

OTHER PUBLICATIONS

Pires et al. Old and new challenges in Parkinson's disease therapeutics. Progress Neurobiol 156: 69-89, 2017.*
White et al. Cancer prevention for the next generation. J Adolescent Health 52: S1-S7, 2013.*
Couture et al. Targeting toll-like receptor (TLR) signaling by toll/interleukin-1 receptor (TIR) domain-containing adapter protein/MyD88 adapter-like (TIRAP/Mal)-derived decoy peptides. J Biol Chem 287(29): 24641-24648, 2012.*
Derossi et al. The third helix of the antennapedia homeodomain translocates through biological membranes. J Biol Chem 268(14): 10444-10450, 1994.*
Toshchakov et al. Targeting TLR4 signaling by TLR4 toll/IL-1 receptor domain-derived decoy peptides: identification of the TLR4 toll/IL-1 receptor domain dimerization interface. J Immunol 186: 4819-4827, 2011.*
Piao et al., "A Decoy Peptide that Disrupts TIRAP Recruitment to TLRs Is Protective in a Murine Model of Influenza", Cell Reports, Jun. 30, 2015, vol. 11, pp. 1941-1952 (13 pages).
Predicted: toll/interleukin-1 receptor domain-containing adapter protein isoform X1 [Cebus capucinus imitator], NCBI Reference Sequence: XP_017382104.1, Jul. 18, 2016.
Maria Loiarro et al., "Targeting TLR/IL-1R Signalling in Human Diseases", Mediators of Inflammation, 2010, pp. 1-12, vol. 2010, Article ID 674363.
Deformed [Echinococcus granulosus], GenBank: CDS15727.1, Aug. 15, 2014.
Deformed [Hymenolepis microstoma], GenBank: CDS27878.1, Dec. 8, 2015.
International Search Report for PCT/KR2018/004803, dated Jul. 26, 2018.

* cited by examiner mBMDM

Fig. 21

```
                        SEQUENCE LISTING

<160> NUMBER OF SEQ ID NOS: 55

<210> SEQ ID NO 1
<211> LENGTH: 8
<212> TYPE: PRT
<213> ORGANISM: Artificial Sequence
<220> FEATURE:
<223> OTHER INFORMATION: Decoy peptide 1

<400> SEQUENCE: 1

Ser His Cys Arg Val Leu Leu Ile
1               5

<210> SEQ ID NO 2
<211> LENGTH: 4
<212> TYPE: PRT
<213> ORGANISM: Artificial Sequence
<220> FEATURE:
<223> OTHER INFORMATION: Decoy peptide 1-2

<400> SEQUENCE: 2

Ser His Cys Arg
1

<210> SEQ ID NO 3
<211> LENGTH: 24
<212> TYPE: PRT
<213> ORGANISM: Artificial Sequence
<220> FEATURE:
<223> OTHER INFORMATION: TIP1

<400> SEQUENCE: 3

Arg Gln Ile Lys Ile Trp Phe Gln Asn Arg Arg Met Lys Trp Lys Lys
1               5                   10                  15

Ser His Cys Arg Val Leu Leu Ile
            20

<210> SEQ ID NO 4
<211> LENGTH: 20
<212> TYPE: PRT
<213> ORGANISM: Artificial Sequence
<220> FEATURE:
<223> OTHER INFORMATION: TIP1-2

<400> SEQUENCE: 4

Arg Gln Ile Lys Ile Trp Phe Gln Asn Arg Arg Met Lys Trp Lys Lys
1               5                   10                  15

Ser His Cys Arg
            20

<210> SEQ ID NO 5
<211> LENGTH: 6
```

```
<212> TYPE: PRT
<213> ORGANISM: Artificial Sequence
<220> FEATURE:
<223> OTHER INFORMATION: Decoy peptide 2

<400> SEQUENCE: 5

Thr Ile Pro Leu Leu Ser
1               5

<210> SEQ ID NO 6
<211> LENGTH: 22
<212> TYPE: PRT
<213> ORGANISM: Artificial Sequence
<220> FEATURE:
<223> OTHER INFORMATION: TIP2

<400> SEQUENCE: 6

Arg Gln Ile Lys Ile Trp Phe Gln Asn Arg Arg Met Lys Trp Lys Lys
1               5                   10                  15

Thr Ile Pro Leu Leu Ser
            20

<210> SEQ ID NO 7
<211> LENGTH: 4
<212> TYPE: PRT
<213> ORGANISM: Artificial Sequence
<220> FEATURE:
<223> OTHER INFORMATION: Decoy peptide 1-3

<400> SEQUENCE: 7

Val Leu Leu Ile
1

<210> SEQ ID NO 8
<211> LENGTH: 20
<212> TYPE: PRT
<213> ORGANISM: Artificial Sequence
<220> FEATURE:
<223> OTHER INFORMATION: TIP1-3

<400> SEQUENCE: 8

Arg Gln Ile Lys Ile Trp Phe Gln Asn Arg Arg Met Lys Trp Lys Lys
1               5                   10                  15

Val Leu Leu Ile
            20

<210> SEQ ID NO 9
<211> LENGTH: 16
<212> TYPE: PRT
<213> ORGANISM: Artificial Sequence
<220> FEATURE:
<223> OTHER INFORMATION: CPP(Penetratin)

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: TAT(48-60)

<400> SEQUENCE: 10

Gly Arg Lys Lys Arg Arg Gln Arg Arg Arg Pro Pro Gln
```

```
<210> SEQ ID NO 11
<211> LENGTH: 18
<212> TYPE: PRT
<213> ORGANISM: Artificial Sequence
<220> FEATURE:
<223> OTHER INFORMATION: pVEC

<400> SEQUENCE: 11

Leu Leu Ile Ile Leu Arg Arg Arg Ile Arg Lys Gln Ala His Ala His
1               5                   10                  15

Ser Lys

<210> SEQ ID NO 12
<211> LENGTH: 27
<212> TYPE: PRT
<213> ORGANISM: Artificial Sequence
<220> FEATURE:
<223> OTHER INFORMATION: Transportan10/TP10

<400> SEQUENCE: 12

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 13
<211> LENGTH: 21
<212> TYPE: PRT
<213> ORGANISM: Artificial Sequence
<220> FEATURE:
<223> OTHER INFORMATION: TP10, PepFect 3
<220> FEATURE:
<221> NAME/KEY: MOD_RES
<222> LOCATION: (21)
<223> OTHER INFORMATION: Amidation on the C-terminal end

<400> SEQUENCE: 13

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 14
<211> LENGTH: 21
<212> TYPE: PRT
<213> ORGANISM: Artificial Sequence
<220> FEATURE:
<223> OTHER INFORMATION: TP10, PepFect 6
<220> FEATURE:
<221> NAME/KEY: MOD_RES
<222> LOCATION: (21)
<223> OTHER INFORMATION: Amidation on the C-terminal end

<400> SEQUENCE: 14

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 15
<211> LENGTH: 18
<212> TYPE: PRT
<213> ORGANISM: Artificial Sequence
<220> FEATURE:
```

<223> OTHER INFORMATION: TP10, PepFect 14
<220> FEATURE:
<221> NAME/KEY: MOD_RES
<222> LOCATION: (18)
<223> OTHER INFORMATION: Amidation on the C-terminal end

<400> SEQUENCE: 15

Ala Gly Tyr Leu Leu Gly Lys Leu Leu Leu Ala Ala Ala Ala Leu Ala
1               5                   10                  15

Leu Leu

<210> SEQ ID NO 16
<211> LENGTH: 21
<212> TYPE: PRT
<213> ORGANISM: Artificial Sequence
<220> FEATURE:
<223> OTHER INFORMATION: NickFect 1
<220> FEATURE:
<221> NAME/KEY: MOD_RES
<222> LOCATION: (21)
<223> OTHER INFORMATION: Amidation on the C-terminal end

<400> SEQUENCE: 16

Ala Gly Tyr Leu Leu Gly Lys Thr Asn Leu Lys Ala Leu Ala Ala Leu
1               5                   10                  15

Ala Lys Lys Ile Leu
            20

<210> SEQ ID NO 17
<211> LENGTH: 21
<212> TYPE: PRT
<213> ORGANISM: Artificial Sequence
<220> FEATURE:
<223> OTHER INFORMATION: NickFect 2
<220> FEATURE:
<221> NAME/KEY: MOD_RES
<222> LOCATION: (21)
<223> OTHER INFORMATION: Amidation on the C-terminal end

<400> SEQUENCE: 17

Ala Gly Tyr Leu Leu Gly Lys Thr Asn Leu Lys Ala Leu Ala Ala Leu
1               5                   10                  15

Ala Lys Lys Ile Leu
            20

<210> SEQ ID NO 18
<211> LENGTH: 21
<212> TYPE: PRT
<213> ORGANISM: Artificial Sequence
<220> FEATURE:
<223> OTHER INFORMATION: NickFect 3
<220> FEATURE:
<221> NAME/KEY: MOD_RES
<222> LOCATION: (21)
<223> OTHER INFORMATION: Amidation on the C-terminal end

<400> SEQUENCE: 18

Ala Gly Tyr Leu Leu Gly Lys Thr Asn Leu Lys Ala Leu Ala Ala Leu
1               5                   10                  15

Ala Lys Lys Ile Leu
            20

<210> SEQ ID NO 19
<211> LENGTH: 27
<212> TYPE: PRT
<213> ORGANISM: Artificial Sequence
<220> FEATURE:

<223> OTHER INFORMATION: MPG

<400> SEQUENCE: 19

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 20
<211> LENGTH: 21
<212> TYPE: PRT
<213> ORGANISM: Artificial Sequence
<220> FEATURE:
<223> OTHER INFORMATION: Pep-1

<400> SEQUENCE: 20

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 21
<211> LENGTH: 18
<212> TYPE: PRT
<213> ORGANISM: Artificial Sequence
<220> FEATURE:
<223> OTHER INFORMATION: MAP

<400> SEQUENCE: 21

Lys Leu Ala Leu Lys Leu Ala Leu Lys Ala Leu Lys Ala Ala Leu Lys
1               5                   10                  15

Leu Ala

<210> SEQ ID NO 22
<211> LENGTH: 9
<212> TYPE: PRT
<213> ORGANISM: Artificial Sequence
<220> FEATURE:
<223> OTHER INFORMATION: R6/W3

<400> SEQUENCE: 22

Arg Arg Trp Trp Arg Arg Trp Arg Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Polyarginine(R8)

<400> SEQUENCE: 23

Arg Arg Arg Arg Arg Arg Arg Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Polyarginine(R9)

<400> SEQUENCE: 24

Arg Arg Arg Arg Arg Arg Arg Arg Arg
1               5

<210> SEQ ID NO 25
<211> LENGTH: 17
<212> TYPE: PRT
<213> ORGANISM: Artificial Sequence
<220> FEATURE:
<223> OTHER INFORMATION: VP22

<400> SEQUENCE: 25

Asn Ala Lys Thr Arg Arg His Glu Arg Arg Arg Lys Leu Ala Ile Glu
1               5                   10                  15

Arg

<210> SEQ ID NO 26
<211> LENGTH: 16
<212> TYPE: PRT
<213> ORGANISM: Artificial Sequence
<220> FEATURE:
<223> OTHER INFORMATION: YTA2

<400> SEQUENCE: 26

Tyr Thr Ala Ile Ala Trp Val Lys Ala Phe Ile Arg Lys Leu Arg Lys
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: YTA4

<400> SEQUENCE: 27

Ile Ala Trp Val Lys Ala Phe Ile Arg Lys Leu Arg Lys Gly Pro Leu
1               5                   10                  15

Gly

<210> SEQ ID NO 28
<211> LENGTH: 22
<212> TYPE: PRT
<213> ORGANISM: Artificial Sequence
<220> FEATURE:
<223> OTHER INFORMATION: M918

<400> SEQUENCE: 28

Met Val Thr Val Leu Phe Arg Arg Leu Arg Ile Arg Arg Ala Cys Gly
1               5                   10                  15

Pro Pro Arg Val Arg Val
            20

<210> SEQ ID NO 29
<211> LENGTH: 20
<212> TYPE: PRT
<213> ORGANISM: Artificial Sequence
<220> FEATURE:
<223> OTHER INFORMATION: CADY

<400> SEQUENCE: 29

Gly Leu Trp Arg Ala Leu Trp Arg Leu Leu Arg Ser Leu Trp Arg Leu
1               5                   10                  15

Leu Trp Arg Ala
            20

<210> SEQ ID NO 30
<211> LENGTH: 21

```
<212> TYPE: PRT
<213> ORGANISM: Artificial Sequence
<220> FEATURE:
<223> OTHER INFORMATION: SAP

<400> SEQUENCE: 30

Val Arg Leu Leu Pro Pro Pro Val Arg Leu Leu Pro Pro Pro Val Arg
1               5                   10                  15

Leu Leu Pro Pro Pro
            20

<210> SEQ ID NO 31
<211> LENGTH: 22
<212> TYPE: PRT
<213> ORGANISM: Artificial Sequence
<220> FEATURE:
<223> OTHER INFORMATION: SAP(E)
<220> FEATURE:
<221> NAME/KEY: MOD_RES
<222> LOCATION: (1)
<223> OTHER INFORMATION: Acetylation on the N-terminal end

<400> SEQUENCE: 31

Cys Gly Gly Trp Val Glu Leu Pro Pro Pro Val Glu Leu Pro Pro Pro
1               5                   10                  15

Val Glu Leu Pro Pro Pro
            20

<210> SEQ ID NO 32
<211> LENGTH: 10
<212> TYPE: PRT
<213> ORGANISM: Artificial Sequence
<220> FEATURE:
<223> OTHER INFORMATION: CyLoP-1

<400> SEQUENCE: 32

Cys Arg Trp Arg Trp Lys Cys Cys Lys Lys
1               5                   10

<210> SEQ ID NO 33
<211> LENGTH: 20
<212> TYPE: PRT
<213> ORGANISM: Artificial Sequence
<220> FEATURE:
<223> OTHER INFORMATION: gH 625

<400> SEQUENCE: 33

His Gly Leu Ala Ser Thr Leu Thr Arg Trp Ala His Tyr Asn Ala Leu
1               5                   10                  15

Ile Arg Ala Phe
            20

<210> SEQ ID NO 34
<211> LENGTH: 30
<212> TYPE: PRT
<213> ORGANISM: Artificial Sequence
<220> FEATURE:
<223> OTHER INFORMATION: GALA

<400> SEQUENCE: 34

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

```
<210> SEQ ID NO 35
<211> LENGTH: 21
<212> TYPE: PRT
<213> ORGANISM: Artificial Sequence
<220> FEATURE:
<223> OTHER INFORMATION: CADY
<220> FEATURE:
<221> NAME/KEY: MOD_RES
<222> LOCATION: (1)
<223> OTHER INFORMATION: Acetylation on the N-terminal end
<220> FEATURE:
<221> NAME/KEY: MISC_FEATURE
<222> LOCATION: (21)
<223> OTHER INFORMATION: X = cysteamide

<400> SEQUENCE: 35

Gly Leu Trp Arg Ala Leu Trp Arg Leu Leu Arg Ser Leu Trp Arg Leu
1               5                   10                  15

Leu Trp Arg Ala Xaa
            20

<210> SEQ ID NO 36
<211> LENGTH: 25
<212> TYPE: PRT
<213> ORGANISM: Artificial Sequence
<220> FEATURE:
<223> OTHER INFORMATION: L17E

<400> SEQUENCE: 36

Ile Trp Leu Thr Ala Leu Lys Phe Leu Gly Lys His Ala Ala Lys His
1               5                   10                  15

Glu Ala Lys Gln Gln Leu Ser Lys Leu
            20                  25

<210> SEQ ID NO 37
<211> LENGTH: 8
<212> TYPE: PRT
<213> ORGANISM: Artificial Sequence
<220> FEATURE:
<223> OTHER INFORMATION: MPPs
<220> FEATURE:
<221> NAME/KEY: MISC_FEATURE
<222> LOCATION: (1)
<223> OTHER INFORMATION: X = cyclohexylalanine
<220> FEATURE:
<221> NAME/KEY: MISC_FEATURE
<222> LOCATION: (3)
<223> OTHER INFORMATION: X = cyclohexylalanine
<220> FEATURE:
<221> NAME/KEY: MISC_FEATURE
<222> LOCATION: (5)
<223> OTHER INFORMATION: X = cyclohexylalanine
<220> FEATURE:
<221> NAME/KEY: MISC_FEATURE
<222> LOCATION: (7)
<223> OTHER INFORMATION: X = cyclohexylalanine

<400> SEQUENCE: 37

Xaa Arg Xaa Lys Xaa Arg Xaa Lys
1               5

<210> SEQ ID NO 38
<211> LENGTH: 40
<212> TYPE: PRT
<213> ORGANISM: Artificial Sequence
<220> FEATURE:
<223> OTHER INFORMATION: RR5-APP

<400> SEQUENCE: 38

Arg Pro Arg Arg Pro Arg Arg Pro Arg Arg Pro Gly Arg Arg Ala Pro
```

```
                1               5                  10                 15
Val Glu Asp Leu Ile Arg Phe Tyr Asn Asp Leu Gln Gln Tyr Leu Asn
                20                 25                 30

Val Val Thr Arg His Arg Tyr Cys
            35                 40
```

<210> SEQ ID NO 39
<211> LENGTH: 38
<212> TYPE: PRT
<213> ORGANISM: Artificial Sequence
<220> FEATURE:
<223> OTHER INFORMATION: RR4-APP

<400> SEQUENCE: 39

```
Arg Arg Pro Arg Arg Pro Arg Arg Pro Gly Arg Arg Ala Pro Val Glu
1               5                  10                 15

Asp Leu Ile Arg Phe Tyr Asn Asp Leu Gln Gln Tyr Leu Asn Val Val
                20                 25                 30

Thr Arg His Arg Tyr Cys
            35
```

<210> SEQ ID NO 40
<211> LENGTH: 37
<212> TYPE: PRT
<213> ORGANISM: Artificial Sequence
<220> FEATURE:
<223> OTHER INFORMATION: RR3-APP

<400> SEQUENCE: 40

```
Gly Pro Arg Arg Pro Arg Arg Pro Gly Arg Arg Ala Pro Val Glu Asp
1               5                  10                 15

Leu Ile Arg Phe Tyr Asn Asp Leu Gln Gln Tyr Leu Asn Val Val Thr
                20                 25                 30

Arg His Arg Tyr Cys
            35
```

<210> SEQ ID NO 41
<211> LENGTH: 15
<212> TYPE: PRT
<213> ORGANISM: Artificial Sequence
<220> FEATURE:
<223> OTHER INFORMATION: TATp-D-1
<220> FEATURE:
<221> NAME/KEY: MOD_RES
<222> LOCATION: (1)
<223> OTHER INFORMATION: Acetylation on the N-terminal end

<400> SEQUENCE: 41

```
Gly Arg Lys Lys Arg Arg Gln Arg Arg Arg Pro Pro Gln Lys Lys
1               5                  10                 15
```

<210> SEQ ID NO 42
<211> LENGTH: 13
<212> TYPE: PRT
<213> ORGANISM: Artificial Sequence
<220> FEATURE:
<223> OTHER INFORMATION: TATp-D-2
<220> FEATURE:
<221> NAME/KEY: MOD_RES
<222> LOCATION: (1)
<223> OTHER INFORMATION: Acetylation on the N-terminal end

<400> SEQUENCE: 42

```
Gly Arg Lys Lys Arg Arg Gln Arg Arg Arg Pro Pro Gln
1               5                  10
```

<210> SEQ ID NO 43
<211> LENGTH: 12
<212> TYPE: PRT
<213> ORGANISM: Artificial Sequence
<220> FEATURE:
<223> OTHER INFORMATION: Cyclic Tat

<400> SEQUENCE: 43

Lys Arg Arg Arg Gln Arg Arg Lys Lys Arg Gly Glu
1               5                   10

<210> SEQ ID NO 44
<211> LENGTH: 22
<212> TYPE: PRT
<213> ORGANISM: Artificial Sequence
<220> FEATURE:
<223> OTHER INFORMATION: K10(QW)6

<400> SEQUENCE: 44

Lys Lys Lys Lys Lys Lys Lys Lys Lys Gln Trp Gln Trp Gln Trp
1               5                   10                  15

Gln Trp Gln Trp Gln Trp
            20

<210> SEQ ID NO 45
<211> LENGTH: 9
<212> TYPE: PRT
<213> ORGANISM: Artificial Sequence
<220> FEATURE:
<223> OTHER INFORMATION: TAT(49-57)

<400> SEQUENCE: 45

Arg Lys Lys Arg Arg Gln Arg Arg Arg
1               5

<210> SEQ ID NO 46
<211> LENGTH: 19
<212> TYPE: PRT
<213> ORGANISM: Artificial Sequence
<220> FEATURE:
<223> OTHER INFORMATION: DPV1047

<400> SEQUENCE: 46

Val Lys Arg Gly Leu Lys Leu Arg His Val Arg Pro Arg Val Thr Arg
1               5                   10                  15

Met Asp Val

<210> SEQ ID NO 47
<211> LENGTH: 22
<212> TYPE: PRT
<213> ORGANISM: Artificial Sequence
<220> FEATURE:
<223> OTHER INFORMATION: ARF(1-22)

<400> SEQUENCE: 47

Met Val Arg Arg Phe Leu Val Thr Leu Arg Ile Arg Arg Ala Cys Gly
1               5                   10                  15

Pro Pro Arg Val Arg Val
            20

<210> SEQ ID NO 48
<211> LENGTH: 28
<212> TYPE: PRT
<213> ORGANISM: Artificial Sequence
<220> FEATURE:
<223> OTHER INFORMATION: BPrPr(1-28)

<400> SEQUENCE: 48

Met Val Lys Ser Lys Ile Gly Ser Trp Ile Leu Val Leu Phe Val Ala
1               5                   10                  15
Met Trp Ser Asp Val Gly Leu Cys Lys Lys Arg Pro
            20                  25

<210> SEQ ID NO 49
<211> LENGTH: 28
<212> TYPE: PRT
<213> ORGANISM: Artificial Sequence
<220> FEATURE:
<223> OTHER INFORMATION: p28

<400> SEQUENCE: 49

Leu Ser Thr Ala Ala Asp Met Gln Gly Val Val Thr Asp Gly Met Ala
1               5                   10                  15
Ser Gly Leu Asp Lys Asp Tyr Leu Lys Pro Asp Asp
            20                  25

<210> SEQ ID NO 50
<211> LENGTH: 26
<212> TYPE: PRT
<213> ORGANISM: Artificial Sequence
<220> FEATURE:
<223> OTHER INFORMATION: VT5

<400> SEQUENCE: 50

Asp Pro Lys Gly Asp Pro Lys Gly Val Thr Val Thr Val Thr Val Thr
1               5                   10                  15
Val Thr Gly Lys Gly Asp Pro Lys Pro Asp
            20                  25

<210> SEQ ID NO 51
<211> LENGTH: 17
<212> TYPE: PRT
<213> ORGANISM: Artificial Sequence
<220> FEATURE:
<223> OTHER INFORMATION: C105Y

<400> SEQUENCE: 51

Cys Ser Ile Pro Pro Glu Val Lys Phe Asn Lys Pro Phe Val Tyr Leu
1               5                   10                  15
Ile

<210> SEQ ID NO 52
<211> LENGTH: 6
<212> TYPE: PRT
<213> ORGANISM: Artificial Sequence
<220> FEATURE:
<223> OTHER INFORMATION: PFVYLI

<400> SEQUENCE: 52

Pro Phe Val Tyr Leu Ile
1               5

<210> SEQ ID NO 53
<211> LENGTH: 15
<212> TYPE: PRT
<213> ORGANISM: Artificial Sequence
<220> FEATURE:
<223> OTHER INFORMATION: Pep-7

```
<400> SEQUENCE: 53

Ser Asp Leu Trp Glu Met Met Met Val Ser Leu Ala Cys Gln Tyr
1               5                   10                  15

<210> SEQ ID NO 54
<211> LENGTH: 11
<212> TYPE: PRT
<213> ORGANISM: Artificial Sequence
<220> FEATURE:
<223> OTHER INFORMATION: BB-loop of TIR domain

<400> SEQUENCE: 54

Arg Asp Phe Ile Pro Gly Val Ala Ile Ala Ala
1               5                   10

<210> SEQ ID NO 55
<211> LENGTH: 16
<212> TYPE: PRT
<213> ORGANISM: Artificial Sequence
<220> FEATURE:
<223> OTHER INFORMATION: C-terminal region of TIR domain

<400> SEQUENCE: 55

Glu Gly Thr Val Gly Thr Gly Cys Asn Trp Gln Glu Ala Thr Ser Ile
1               5                   10                  15
```

PEPTIDE FOR TOLL-LIKE RECEPTOR (TLR) INHIBITION AND PHARMACEUTICAL COMPOSITION COMPRISING SAME

CROSS REFERENCE TO RELATED APPLICATIONS

This application is a National Stage of International Application No. PCT/KR2018/004803 filed Apr. 25, 2018, claiming priority based on Korean Patent Application No. 10-2017-0056842 filed May 4, 2017 and Korean Patent Application No. 10-2018-0046715 filed Apr. 23, 2018.

SEQUENCE LISTING

The content of the electronically submitted sequence listing, file name: Sequence_Listing_As_Filed_20211214. txt; size: 16,533 bytes; and date of creation: Dec. 13, 2021, filed herewith, is incorporated herein by reference in its entirety.

TECHNICAL FIELD

The present invention relates to a fusion peptide that inhibits signaling pathways of Toll-like receptor (TLR)1/2, TLR2/6, TLR7, TLR8, and TLR9 as well as TLR4 and TLR3, and a pharmaceutical composition for preventing or treating a TLR pathway-mediated disease, comprising the same.

BACKGROUND ART

Innate immunity is the first line of defense against bacterial infection in a mammalian immune system and is activated via recognition of pathogen-associated molecular patterns (PAMPs) or danger-associated molecular patterns (DAMPs) by pattern recognition receptors such as Toll-like receptors (TLRs).

TLRs play an important role in innate immune responses and may be divided into extracellular TLRs, which act on the plasma membrane and include TLR1, TLR2, TLR4, TLR5, TLR6, and TLR11, and intracellular TLRs, which act in the inside of cell such as endosome and include TLR3, TLR7, TLR8, and TLR9. Structurally, TLRs have a leucine-rich repeat (LRR) site, which is recognized by a ligand or an accessory molecule, at the N-terminus of the extracellular domain, and a Toll/interleukin 1 receptor (TIR) domain, which transduces a signal, at the C-terminus of the intracellular portion.

In particular, TLR4 is the first identified receptor in the TLR family, and activates innate immune signals which are amplified through myeloid differentiation 88 (MyD88)-dependent and MyD88-independent signaling pathways. In contrast, TLR3 activates only the MyD88-independent signaling pathway. Due to this role of TLRs, there is a growing interest in studies intended to use TLRs as targets for treating various immune diseases.

MyD88-dependent signaling of TLR4 is initiated by LPS recognition through accessory molecules such as cluster of differentiation 14 (CD14) and myeloid differentiation factor 2 (MD2). After binding of LPS, TLR4 dimerizes, which allows the TIR domain of TLR4 and the TIR domain of TIR domain adapter protein (TIRAP or MyD88 adapter-like (MAL)) to bind to each other so as to form a complex with MyD88, thereby activating its signaling pathway. Activated TLR4 induces early activation of NFκB, migration to the nucleus, and activation of MAPK, through a Myd88-dependent signaling process. The activation of NFκB and MAPK secretes inflammatory cytokines such as tumor necrosis factor α (TNF-α), interleukin 1β (IL-1β), and interleukin 6 (IL-6). MyD88-independent signaling processes of TLR4 and TLR3 are initiated by binding between TIR domain of each TLR and TIR domain of TIR domain-containing adapter-inducing interferon-β (TRIF)/TRIF-related adaptor molecule (TRAM) complex, and secrete type 1 interferons by activation of interferon-regulatory factors (IRFs). In addition, TLR4 activity produces oxidative stressors such as NO and ROS in macrophages.

As such, since TLRs may be targets for treating various diseases such as autoimmune diseases, inflammatory diseases, and cancer, studies on substances targeting TLRs and medical compositions for treating diseases related to TLRs have been conducted. In particular, a number of TLR4 promoters and antagonists have been obtained by modifying the main skeletal structure of lipid A, and it has been found that eritoran, lipid A, and *Rhodobacter sphaeroids* lipid A (RsLA) can inhibit interaction between LPS and MD2 and prevent LPS-induced shock in mice. In addition, it has been reported that the TLR4 signaling pathway induced by LPS is involved in formation of NLRP3 inflammasome, and thus is closely related to degenerative neurological diseases such as Alzheimer's disease and Parkinson's disease.

On the other hand, studies are actively conducted on peptides that act similar to or opposite to pathogen-associated molecular patterns (PAMPs) by using decoy peptides which use a part of a binding domain of a protein and control signaling by binding, in place of the protein, to a protein that originally interacts therewith. Peptides are known to have fewer side effects, and easier modification and quality control, than common small-molecule therapeutic agents, and low cell permeability thereof is also improved due to development of cell-penetrating peptides (CPPs).

DISCLOSURE OF INVENTION

Technical Problem

The present inventors have identified that a novel peptide (decoy peptide 1) consisting of the amino acid sequence of SEQ ID NO: 1, and a fusion peptide (Toll-like receptor inhibitory peptide 1, TIP1) in which the novel peptide is linked to the N-terminus of a cell-penetrating peptide inhibit a lipopolysaccharide (LPS)-induced TLR4 signaling pathway, thereby not only inhibiting secretion of cytokines (IL-6, TNF-α, IFN-β), NO, and ROS, and activation of NF-κB and MAPK, but also alleviating renal and hepatic damage caused by hyperactivity of TLR4, sepsis, and rheumatoid arthritis in animals. The present inventors have also proven that the novel peptide and the fusion peptide inhibit a TLR3 signaling pathway induced by Poly(I:C) and formation of NLRP3 inflammasome induced by LPS/ATP, thereby completing the present invention. In addition, it was identified by cell experiments that the novel peptide and the fusion peptide also partially inhibit TLR1/2, TLR2/6, TLR7, TLR8, and TLR9.

Accordingly, an object of the present invention is to provide a peptide consisting of the amino acid sequence of SEQ ID NO: 1, and a fusion peptide in which a peptide consisting of the amino acid sequence of SEQ ID NO: 1 or SEQ ID NO: 2 is linked to the N-terminus of a cell-penetrating peptide.

In addition, another object of the present invention is to provide a pharmaceutical composition for preventing or treating at least one TLR pathway-mediated disease selected from the group consisting of autoimmune diseases, inflammatory diseases, and degenerative neurological diseases, comprising, as an active ingredient, a peptide consisting of the amino acid sequence of SEQ ID NO: 1 or SEQ ID NO: 2.

Solution to Problem

In order to achieve the above objects, the present invention provides a peptide consisting of the amino acid sequence of SEQ ID NO: 1.

In addition, the present invention provides a fusion peptide in which a peptide consisting of the amino acid sequence of SEQ ID NO: 1 or SEQ ID NO: 2 is linked to the N-terminus of a cell-penetrating peptide.

In addition, the present invention provides a pharmaceutical composition for preventing or treating at least one TLR pathway-mediated disease selected from the group consisting of autoimmune diseases, inflammatory diseases, and degenerative neurological diseases, comprising, as an active ingredient, a peptide consisting of the amino acid sequence of SEQ ID NO: 1 or SEQ ID NO: 2.

In addition, the present invention provides a pharmaceutical composition for preventing or treating at least one TLR pathway-mediated disease selected from the group consisting of autoimmune diseases, inflammatory diseases, and degenerative neurological diseases, comprising, as an active ingredient, a fusion peptide in which a peptide consisting of the amino acid sequence of SEQ ID NO: 1 or SEQ ID NO: 2 is linked to the N-terminus of a cell-penetrating peptide.

Advantageous Effects of Invention

The fusion peptide of the present invention has an excellent effect of inhibiting signaling pathways of various TLRs including TLR4, and thus hinders immune responses mediated by the TLRs so that the fusion peptide can be usefully used for preventing and treating various TLR pathway-mediated diseases caused by the signaling pathways, such as autoimmune diseases, inflammatory diseases, or degenerative neurological diseases.

BRIEF DESCRIPTION OF DRAWINGS

The patent or application file contains at least one drawing executed in color. Copies of this patent or application publication with the color drawing(s) will be provided by the Office upon request and payment of the necessary fee

FIGS. 4(a), 4(b), and 4(c) illustrate secretion levels of TNF-α, IL-6, and IFN-β, respectively.

FIGS. 5(a), 5(b), and 5(c) illustrate a generation level of NO in the cytoplasm, a generation level of ROS in the cytoplasm, and a level of NO secreted out of a cell, respectively.

FIGS. 6(a), 6(b), 6(c), and 6(d) illustrate generation levels of TNF-α, IL-6, NO, and IFN-β, respectively.

FIG. 12 illustrates results obtained by identifying NF-κB activity and NO secretion levels of peptides having the entire or partial amino acid sequence of TIP1. In FIG. 12(a) and FIG. 12(b), the sequences of TIP1, TIP1-1, TIP1-2, and TIP1-3 are the sequence of SEQ ID NOs: 3, 9, 4, and 8, respectively.

FIGS. 14(a), 14(b), and 14(c) illustrate secretion levels of TNF-α, IL-12p40, and IL-6, respectively.

FIG. 15(a) illustrates results obtained by identifying, through Western blotting, secretion levels of TNF-α and IL-6, and FIG. 15(b) graphically illustrates quantification of band intensities with the Westin blotting.

FIG. 16 illustrate results obtained by subjecting C57BL/6J mice to combined treatment with PBS and LPS, or with TIP1 and LPS, and then identifying an effect of TIP1 on renal and hepatic damage through the blood collected 24 hours after the treatment.

FIGS. 20(a), 20(b), 20(c), and 20(d) illustrate results obtained by observing body weight, squeaking (made by a mouse), degree of foot swelling, and arthritis index, respectively.

FIG. 21 illustrates results obtained by subjecting a CIA model of DAB-1J mice to treatment with TIP1, and then measuring a 3D image and bone mineral density (BMD) using micro-computed tomography (Micro-CT), indicating that arthritis was treated.

BEST MODE FOR CARRYING OUT THE INVENTION

Figure 1A:
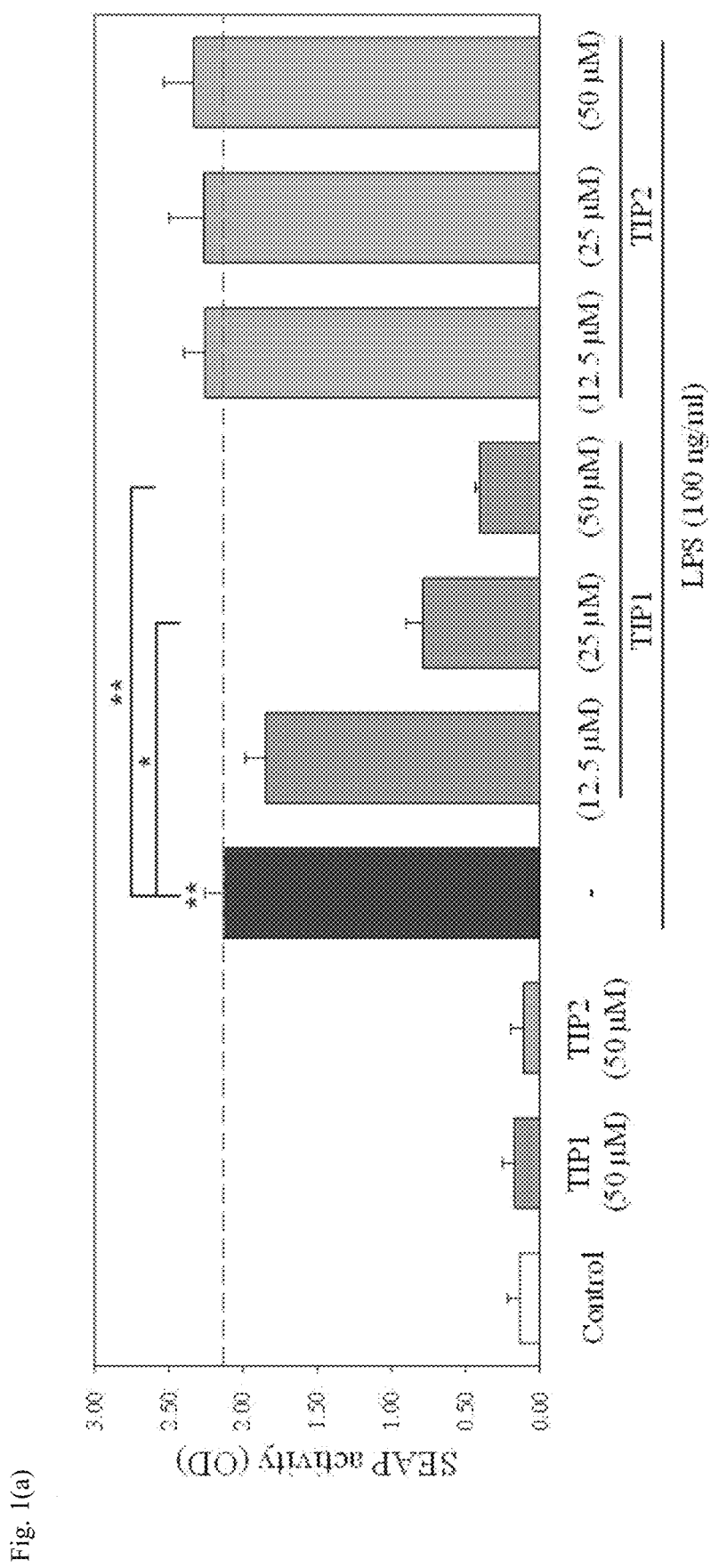
FIG. 1(a) illustrates that in a case where HEK-Blue™ hTLR4 (human TLR4) cells were treated with different concentrations of TIPs (TIP1, TIP2, in which TIP2 was used as a control) together with LPS, secreted alkaline phosphatase (SEAP) activity was decreased by TIP1.

Hereinafter, the present invention will be described in detail.

The present invention provides a peptide consisting of the amino acid sequence of SEQ ID NO: 1.

As used herein, the term "peptide" refers to a linear molecule formed by binding of amino acid residues to each other with peptide bonds. The peptide may be prepared according to chemical synthesis methods known in the art. The peptide may preferably be prepared according to a solid phase synthesis technique, but the method is not limited thereto.

As used herein, the term "TLR4" refers to a protein which is encoded by TLR4 gene and belongs to Toll-like receptors (TLRs), a family of transmembrane proteins that function as surveillants for pathogen infection, and is also called cluster of differentiation 284 (CD284). The TLR4 is very important for activation of the innate immune system because it recognizes a variety of pathogen-associated molecular patterns (PAMPs), including LPS of Gram-negative bacteria.

As used herein, the term "TLR3" refers to a protein which is encoded by TLR3 gene and belongs to Toll-like receptors (TLRs), a family of transmembrane proteins that function as surveillants for pathogen infection, and is also called cluster of differentiation 283 (CD283). The TLR3 is very important for activation of the innate immune system because it recognizes a variety of PAMPs, including viral double-strand RNA (dsRNA).

As used herein, the term "NLRP3 inflammasome" refers to a receptor and sensor of the intrinsic immune system that regulates activation of caspase-1; and the NLRP3 inflammasome is a type of inflammasome that causes inflammation in response to microbial infection or the like, and is activated in response to various stimuli. NLRP3 requires priming, an example of which is binding of LPS to TLR4. Along with ATP, the TLR4 signaling pathway by LPS promotes formation of NLRP3 inflammasome. Abnormally activated NLRP3 inflammasome leads to development of a variety of inflammatory diseases, in particular, degenerative neurological diseases. Recent studies have shown that a direct link exists between accumulation of beta amyloid (amyloid β), which is considered a major cause of Alzheimer's disease, and NLRP3 inflammasome, and have also reported association of NLRP3 inflammasome with Parkinson's disease.

As used herein, the term "signaling pathway mediated by TLR4" refers to a signaling pathway through TLR4. This pathway may be an LPS response that depends on the TLR4/MD2 complex formed by TLR4 and MD2, through which signals are transduced. TLR4 transduces signals by several adapter proteins and operates through Mal (also called TIRAP) and MyD88, TRAM and TRIF, or the like. Activated TLR4 activates NF-κB through a Myd88-dependent signaling process, and thus causes NF-κB to migrate to the nucleus, thereby inducing activation of MAPK. Due to the activation of NF-κB and MAPK, inflammatory cytokines such as TNF-α, IL-1β, and IL-6 are secreted, and oxidative stressors such as nitric oxide (hereinafter referred to as NO) and reactive oxygen species (hereinafter referred to as ROS) are produced in macrophages. In addition, activation of TRAM/TRIF, interferon-regulatory factors (IRFs), and NF-κB induces a MyD88-independent signaling process so that type 1 interferon is secreted.

As used herein, the term "TIR domain" refers to a domain for intracellular signaling, which has three highly conserved regions and mediates interactions between TLRs and other signaling molecules. Activated TIR domains induce binding of MyD88 and activate TLR signaling pathways.

As used herein, the term "inhibition" refers to a phenomenon in which biological action or signaling activity is deteriorated due to deficiency, disproportion, and many other causes, and this phenomenon may be a phenomenon of partially or completely blocking, decreasing, or preventing activity of TLRs, delaying activation thereof, or inactivating or down-regulating TLRs. According to an embodiment of the present invention, there is provided a use of the peptide or fusion peptide according to the present invention, for inhibition of TLR4 and TLR3 signaling pathways and NLRP3 inflammasome. In addition, there is provided a use thereof for partial inhibition of TLR1/2, TLR2/6, TLR7, TLR8, and TLR9.

In the present invention, the S-H-C-R sequence (SEQ ID NO: 2) in a peptide consisting of the amino acid sequence of SEQ ID NO: 1 is characterized by specifically binding to the Toll/interleukin-1 receptor (TIR) domain of a Toll-like receptor (TLR).

In binding to the TIR domain of TLR4, the peptide consisting of the amino acid sequence of SEQ ID NO: 1 according to the invention has sequence specificity. The present inventors searched for the minimal amino acid region of TIP1 which binds to the TIR domain of TLR4 and examined whether this region can effectively inhibit the signaling pathway of TLR4. That is, according to an embodiment of the present invention, a decoy peptide was selected from the TIR domain of TIRAP. Using the amino acid sequence thereof, S-H-C-R-V-L-L-I, sequences S-H-C-R (decoy peptide 1-2, SEQ ID NO: 2) and V-L-L-I (decoy peptide 1-3, SEQ ID NO: 7) were respectively bound to the N-terminus of the same CPP sequence as used in Example 1-1. HEK-Blue™-hTLR4 cells and hPBMC cells were treated with the respective resulting products together with LPS, and then NF-κB activity and NO secretion levels were measured from the respective cells. As a result, it was identified that the S-H-C-R (decoy peptide 1-2) sequence is important for producing an inhibitory effect.

In addition, the present invention provides a fusion peptide in which a peptide consisting of the amino acid sequence of SEQ ID NO: 1 or SEQ ID NO: 2 is linked to the N-terminus of a cell-penetrating peptide.

In the present invention, the fusion peptide may inhibit a signaling pathway mediated by a Toll-like receptor (TLR), in which the Toll-like receptor (TLR) may be any one selected from the group consisting of Toll-like receptor 1/2 (TLR1/2), Toll-like receptor 2/6 (TLR2/6), Toll-like receptor 3 (TLR3), Toll-like receptor 4 (TLR4), Toll-like receptor 7 (TLR7), Toll-like receptor 8 (TLR8), and Toll-like receptor 9 (TLR9). The TLR may be characterized by being preferably Toll-like receptor 4 (TLR4) or Toll-like receptor 3 (TLR3), and more preferably Toll-like receptor 4 (TLR4).

In addition, in the present invention, blockage of the TLR signaling pathway by the fusion peptide may result in inhibition of expression of TNF-α, IL-6, or IFN-β; inhibition of secretion of NO or ROS; or inhibition of activity of NF-κB, MAPK, or NLRP3 inflammasome; and the fusion peptide may be characterized by inhibiting both MyD88-dependent and MyD88-independent TLR4 signaling pathways.

As used herein, the term "cell-penetrating peptide (CPP)" refers to a type of signal peptide which is a type of combination of specific amino acid sequences used for the purpose of delivering high-molecular substances such as protein, DNA, or RNA, into a cell. To date, the cell-penetrating peptide has been used for delivering a variety of low-molecular compounds, high-molecular substances, such as protein, peptide, RNA, or DNA, into a cell.

The fusion peptide of the present invention uses a cell-penetrating peptide. There is no particular limitation on the cell-penetrating peptide as long as the cell-penetrating peptide has a characteristic of entering into a cell by endocytosis mechanism. Preferably, the cell-penetrating peptide may be selected from the cell-penetrating peptides listed in Table 1, or variants thereof, and used.

TABLE 1

| Peptide | Origin | Sequence | SEQ ID NO |
|---|---|---|---|
| Penetratin | Drosophila Antennapedia homeodomain | RQIKIWFQNRRMKWKK | 9 |
| TAT$_{(48-60)}$ | Human immunodeficiency virus type 1 (HIV-1) TAT | GRKKRRQRRRPPQ | 10 |
| pVEC | VE-Cadherin(615-632) | LLIILRRRIRKQAHAHSK | 11 |
| Transportan10/ TP10 | Galanin-Lys-mastoparan | GWTLNSAGYLLGKINLKALAALA KKIL | 12 |
| MPG | A hydrophobic domain from the fusion sequence of HIV gp41 and NLS of SV40 T-antigen | GALFLGFLGAAGSTMGAWSQPKK KRKV | 19 |
| Pep-1 | NLS from Simian Virus 40 large T antigen and reverse transcriptase of HIV-1 | KETWWETWWTEWSQPKKKRKV | 20 |

TABLE 1-continued

| Peptide | Origin | Sequence | SEQ ID NO |
|---|---|---|---|
| MAP | Amphipathic model peptide | KLALKLALKALKAALKLA | 21 |
| $R_6/W_3$ | Based on penetratin | RRWWRRWRR | 22 |
| Polyarginine($R_9$, $R_8$) | Positively charged sequence | $R_n$, n = 8 or 9 | 23, 24 |
| VP22 | Herpes simplex virus | NAKTRRHERRRKLAIER | 25 |
| YTA2 | MMP cleavage site as seeding sequence | YTAIAWVKAFIRKLRK | 26 |
| YTA4 | MMP cleavage site as seeding sequence | IAWVKAFIRKLRKGPLG | 27 |
| M918 | The tumor suppressor protein p14ARF | MVTVLFRRLRIRRACGPPRVRV | 28 |
| CADY | Derived from PPTG1 peptide, W and charged amino acids | GLWRALWRLLRSLWRLLWRA | 29 |
| SAP | Designed based on a natural protein of maize, γ-zein VHL (PPP)$_8$ | (VRLLPPP)$_3$ | 30 |
| SAP(E) | Design inspired by SAP; Arg residue replaced by Glu | Ac-CGGW(VELPPP)3 | 31 |
| CyLoP-1 | Derived from crotamine toxin found in snake venom, crot(27-39) | CRWRWKCCKK | 32 |
| gH 625 | Based on the 625-644 residues of the glycoprotein HSV 1 | HGLASTLTRWAHYNALIRAF | 33 |
| GALA | Glu-rich an containing His (imidazole group) in order to be pH responsive (endosomes) (Designed to efficiently escape endosomes) | WEAALAEALAEALAEHLAEALAE ALEALAA | 34 |
| CADY | Designed; based on chimeric peptide carrier PPTG1 derived from the fusion peptide JTS1 | Ac-GLWRALWRLLRSLWRLLWRA-cysteamide | 35 |
| L17E | Inspired by the spider venom M-lycotoxin | IWLTALKFLGKHAAKHEAKQQLS KL | 36 |
| MPPs | Designed to contain un-natural, cyclohexylalanine ($F_x$) residues and to have differential intracellular localization | Mitochondria-penetrating peptides (example: $F_X rF_X KF_X rF_X K$) | 37 |
| RR$_5$-APP RR$_4$-APP RR$_3$-APP | Small proteins (36-residue polypeptides) | RPRRPRRPRRPGRRAPVEDLIRFY NDLQQYLNVVTRHRYC RRPRRPRRPGRRAPVEDLIRFYND LQQYLNVVTRHRYC GPRRPRRPGRRAPVEDLIRFYNDL QQYLNVVTRHRYC | 38 39 40 |

TABLE 1-continued

| Peptide | Origin | Sequence | SEQ ID NO |
|---|---|---|---|
| TATp-D | Analogue of TAT | Ac-GRKKRRQRRRPPQ-K-K<br>Ac-GRKKRRQRRRPPQ | 41<br>42 |
| Cyclic Tat | Lys- and Glu- amino acids added to the linear Tat sequence to obtain a ring with the same overall charge as the native form | c[K-rRrQrRkKrG-E]c | 43 |
| K$_{10}$(QW)$_6$ | The design was based on combining W and K at the primary structure level to obtain self-assembly into a variety of nanostructures | KKKKKKKKKKQWQWQWQWQW | 44 |
| TAT$_{(49-57)}$ | HIV-1 TAT protein | RKKRRQRRR | 45 |
| DPV1047 | Chemically synthesized | VKRGLKLRHVRPRVTRMDV | 46 |
| ARF$_{(1-22)}$ | p14ARF protein | MVRRFLVTLRIRRACGPPRVRV | 47 |
| BPrPr$_{(1-28)}$ | N terminus of unprocessed bovine prion protein | MVKSKIGSWILVLFVAMWSDVGLCKKRP | 48 |
| p28 | Azurin | LSTAADMQGVVTDGMASGLDKDYLKPDD | 49 |
| VT5 | Chemically synthesized | DPKGDPKGVTVTVTVTGKGDPKPD | 50 |
| C105Y | α1-Antitrypsin | CSIPPEVKFNKPFVYLI | 51 |
| PFVYLI | Derived from synthetic C105Y | PFVYLI | 52 |

Meanwhile, among the cell-penetrating peptides in Table 1, Transportan includes those used in the form of the following variants: AGYLLGKINLKALAALAKKIL-NH$_2$ (TP10, PepFect 3, SEQ ID NO: 13), AGYLLGKINLKA-LAALAKKIL-NH$_2$ (TP10, PepFect 6, SEQ ID NO: 14), AGYLLGKLLOOLAAAALOOLL-NH$_2$ (TP10, PepFect 14, SEQ ID NO: 15), AGYLLGKTNLKALAALAKKIL-NH$_2$ (NickFect 1, SEQ ID NO: 16), AGYLLGKTNLKA-LAALAKKIL-NH$_2$ (NickFect 2, SEQ ID NO: 17), and AGYLLGKTNLKALAALAKKIL-NH$_2$ (NickFect 3, SEQ ID NO: 18).

In addition, in the amino acid sequence (MPPs) consisting of SEQ ID NO: 37 in Table 1, r means d-arginine, and the 2$^{nd}$ and 6$^{th}$ amino acids in the amino acid sequence of SEQ ID NO: 37 correspond thereto. In addition, SEQ ID NO: 41 and 42 in Table 1 are branched with each other and constitute one peptide (TATp-D) which is characterized in that branching is made by linking of the 14$^{th}$ Lys residue (K) in the amino acid sequence of SEQ ID NOs: 41 to the 13$^{th}$ Gln residue (Q) in the amino acid sequence of SEQ ID NO: 42. Further, in the amino acid sequence (Cyclic Tat) consisting of SEQ ID NO: 43 in Table 1, r means d-arginine, and the 2$^{nd}$, 4$^{th}$, 6$^{th}$ and 10$^{th}$ amino acids in the amino acid sequence of SEQ ID NO: 43 correspond thereto. Likewise, k means d-lysine, and the 8$^{th}$ amino acid in the amino acid sequence of SEQ ID NO: 43 corresponds thereto. SEQ ID NO: 43 is characterized by being a cyclic peptide.

In an embodiment of the present invention, an experiment was performed by selecting the Penetratin sequence (RQIKIWFQNRRMKWKK, SEQ ID NO: 9) among the cell-penetrating peptides in Table 1, and it will be apparent to those skilled in the art that a similar effect to the present invention is exhibited even in a case where a cell-penetrating peptide other than the actually used cell-penetrating peptide is fused with the peptide of the present invention.

In the present invention, the fusion peptide in which a peptide consisting of the amino acid sequence of SEQ ID NO: 1 or SEQ ID NO: 2 is linked to the N-terminus of a cell-penetrating peptide may be characterized by preferably consisting of the amino acid sequence of SEQ ID NO: 3 or SEQ ID NO: 4. In addition, variants of the amino acid sequences may also be included within the scope of the present invention. Specifically, the variants may encompass all peptides having a sequence homology, to SEQ ID NO: 3 or 4, respectively, of at least 70%, preferably at least 80%, more preferably at least 90%, even more preferably at least 95%, still more preferably at least 98%, and most preferably at least 99%. The term "homology" is intended to refer to a degree of similarity with a wild type amino acid sequence or a wild type nucleic acid sequence.

According to an embodiment of the present invention, the fusion peptide according to the present invention inhibits a lipopolysaccharide (LPS)-induced TLR4 signaling pathway, thereby exhibiting excellent effects of not only inhibiting secretion of cytokines (IL-6, TNF-α, IFN-β), NO, and ROS, and activation of NF-κB and MAPK, but also alleviating renal and hepatic damage caused by hyperactivity of TLR4, sepsis, and rheumatoid arthritis in animals, and inhibiting Poly(I:C)-induced TLR3 signaling pathway and LPS/ATP-induced formation of NLRP3 inflammasome. Thus, the fusion peptide can be usefully used for preventing and treating autoimmune diseases, inflammatory diseases, caused by the signaling pathway, or degenerative neurological diseases caused by NLRP3 inflammasome.

In addition, in the present invention, the fusion peptide according to the present invention can be used as an inhibitor for TLR4, TLR3, and NLRP3 inflammasome.

As used herein, the term "inhibitor" refers to a molecule that partially or completely hinders an effect of other molecules, such as receptors or intracellular mediators, by any mechanism.

As used herein, the term "inhibitor for TLR4, TLR3, and NLRP3 inflammasome" refers to a substance that can directly or indirectly, or substantially interfere with, decrease, or hinder biological activity of TLR4, TLR3, and NLRP3 inflammasome. Preferably, a peptide that is reactive with TLR4, TLR3 refers to a substance which can bind directly to TIR domain of TLR4, TLR3 and neutralize activity of TLR4, TLR3, thereby blocking TLR4, TLR3 signaling pathways, so that decreased activation of NF-κB and MAPK, and NLRP3 inflammasome is caused to decrease secretion of inflammatory cytokines, NO, and ROS.

In addition, the present invention provides a pharmaceutical composition for preventing or treating at least one TLR pathway-mediated disease selected from the group consisting of autoimmune diseases, inflammatory diseases, and degenerative neurological diseases, comprising, as an active ingredient, a peptide consisting of the amino acid sequence of SEQ ID NO: 1 or SEQ ID NO: 2.

In addition, the present invention provides a pharmaceutical composition for preventing or treating at least one TLR pathway-mediated disease selected from the group consisting of autoimmune diseases, inflammatory diseases, and degenerative neurological diseases, comprising, as an active ingredient, a fusion peptide in which a peptide consisting of the amino acid sequence of SEQ ID NO: 1 or SEQ ID NO: 2 is linked to the N-terminus of a cell-penetrating peptide. The fusion peptide may be characterized by preferably consisting of the amino acid sequence of SEQ ID NO: 3 or SEQ ID NO: 4, and variants of the amino acid sequences may also be included within the scope of the present invention.

As used herein, the term "pathway-mediated disease" refers to any pathological condition in which activation of one or more TLRs and TLR-mediated signaling pathways are contributing factors. The condition may be characterized by being preferably at least one selected from the group consisting of autoimmune diseases, inflammatory diseases, and degenerative diseases. However, the condition is not limited thereto.

As used herein, the term "autoimmune disease" refers to a disease that is caused by a process in which a phenomenon is generated where a problem occurs in inducing or maintaining self-tolerance, which causes immune responses to self-antigens, so that the body's own tissue is attacked thereby. The self-tolerance refers to immunologic unresponsiveness that does not harmfully respond to antigenic substances constituting the self. The autoimmune disease of the present invention include, but is not limited to, insulin-dependent diabetes, multiple sclerosis, experimental autoimmune encephalomyelitis, rheumatoid arthritis, experimental autoimmune arthritis, myasthenia gravis, thyroiditis, experimental form of uveitis, Hashimoto thyroiditis, primary myxedema, thyroid poisoning, malignant anemia, autoimmune atrophic gastritis, Addison's disease, premature menopause, male infertility, childhood diabetes, Goodpasture syndrome, common pemphigus, pemphigoid, sympathetic ophthalmitis, lens uveitis, autoimmune hemolytic anemia, idiopathic leukocytopenia, primary biliary cirrhosis, chronic active hepatitis Hbs-ve, latent cirrhosis, ulcerative colitis, Sjogren's syndrome, scleroderma, Wegener's granulomatosis, polymyositis/skin myositis, discoid LE, and systemic lupus erythematosus.

In addition, as used herein, the term "inflammatory disease" refers to a disease caused by inflammatory agents (inflammatory cytokines), such as TNF-α, IL-1, IL-6, prostaglandin, leukotriene, or NO, which are secreted by immune cells such as macrophages in a case where the immune system is excessively accentuated due to harmful stimuli such as inflammation-inducing factors or irradiation. The inflammatory disease in the present invention includes, but is not limited to, asthma, eczema, psoriasis, allergy, rheumatoid arthritis, psoriatic arthritis, atopic dermatitis, acne, atopic rhinitis, pneumonia, allergic dermatitis, chronic sinusitis, contact dermatitis, seborrheic dermatitis, gastritis, gout, gouty arthritis, ulcer, chronic bronchitis, Crohn's disease, ulcerative colitis, ankylosing spondylitis, sepsis, vasculitis, bursitis, lupus, rheumatoid polymyalgia, temporal arteritis, multiple sclerosis, solid tumor, Alzheimer's disease, atherosclerosis, obesity, and viral infection.

As used herein, the term "degenerative neurological disease" refers to abnormalities in motor control ability, cognitive function, perceptual function, sensory function, and autonomic nerve function due to decrease or loss of function of nerve cells. The degenerative neurological diseases are mainly classified by clinical features, in which classification is based on major symptoms and affected areas. The degenerative neurological disease in the present invention includes, but is not limited to, Alzheimer's disease, frontal temporal dementia, Louis dementia, corticobasal degeneration, Parkinson's disease, multiple system atrophy, Huntington's disease, progressive supranuclear palsy, Lou Gehrig's disease, primary lateral sclerosis, spinal muscular atrophy.

The pharmaceutical composition of the present invention may comprise a pharmaceutically effective amount of the peptide alone or in combination with one or more pharmaceutically acceptable carriers, excipients, or diluents. The pharmaceutically effective amount refers to an amount sufficient to prevent, ameliorate, and treat symptoms of autoimmune diseases.

The term "pharmaceutically acceptable" refers to a composition which is physiologically acceptable, and typically does not cause gastrointestinal disorders, allergic reactions such as dizziness, or similar reactions in a case of being administered to a human. Examples of the carrier, the excipient, and the diluent may include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinyl pyrrolidone, water, methylhydroxy benzoate, propylhydroxy benzoate, talc, magnesium stearate, and mineral oil.

In addition, the pharmaceutical composition of the present invention may further comprise a filler, an anti-coagulant, a lubricant, a wetting agent, a fragrance, an emulsifier, a preservative, and the like.

In addition, along with the peptide, the pharmaceutical composition of the present invention may comprise at least one known active ingredient having a therapeutic effect on autoimmune diseases, inflammatory diseases, or degenerative neurological diseases.

The pharmaceutical composition of the present invention may be formulated using methods known in the art so that the pharmaceutical composition can provide rapid, sustained, or delayed release of the active ingredient after being administered to a mammal. The formulation may be in the form of powders, granules, tablets, emulsions, syrups, aerosols, soft or hard gelatin capsules, sterile injectable solutions, sterile powders.

The pharmaceutical composition of the present invention may be administered through various routes including oral, transdermal, subcutaneous, intravenous, or intramuscular route, and a dose of the active ingredient may be appropriately selected depending on various factors such as route of administration, the patient's age, sex, body weight, and severity of the patient's condition. The pharmaceutical composition may be administered in combination with known compounds having an effect of preventing, ameliorating, or treating symptoms of autoimmune diseases, inflammatory diseases, or degenerative neurological diseases.

In addition, the present invention provides a method for preventing or treating a TLR pathway-mediated disease, comprising: a step of administering, to an individual in need thereof, a peptide consisting of the amino acid sequence of SEQ ID NO: 1 or SEQ ID NO: 2.

In addition, the present invention provides a method for preventing or treating a TLR pathway-mediated disease, comprising: a step of administering, to an individual in need thereof, a fusion peptide in which a peptide consisting of the amino acid sequence of SEQ ID NO: 1 or SEQ ID NO: 2 is linked to the N-terminus of a cell-penetrating peptide.

The individual is preferably a mammal including a human, and includes all patients in need of treatment for a TLR pathway-mediated disease, such as patients who are being treated for a TLR pathway-mediated disease, patients who have been treated for a TLR pathway-mediated disease, patients who need to be treated for a TLR pathway-mediated disease, with patients who have undergone a surgical operation to treat a TLR pathway-mediated disease being also included.

In addition, the peptide consisting of the amino acid sequence of SEQ ID NO: 1 or SEQ ID NO: 2 of the present invention; or the fusion peptide in which the peptide consisting of the amino acid sequence of SEQ ID NO: 1 or SEQ ID NO: 2 is linked to the N-terminus of a cell-penetrating peptide may be simultaneously/sequentially applied in combination with other conventional drugs or methods for treating a TLR pathway-mediated disease.

MODE FOR THE INVENTION

Hereinafter, the present invention will be described in more detail by way of examples and experimental examples. The following examples and experimental examples are only for illustrating the present invention, and the scope of the present invention is not limited by the following examples and experimental examples.

Example 1. Preparation of Test Samples 1-1. Selection of Peptides that Specifically Bind to TIR Domain of TLR4

In order to select peptides that specifically bind to the TIR domain of TLR4, the present inventors selected two sequences (decoy peptides 1, 2) from the TIR domain of TIRAP, and linked a cell-penetrating peptide (CPP) derived from *Drosophila* antennapedia homeodomain to the N terminus of each of the sequences, thereby synthesizing novel peptides TIP1 and TIP2. The sequences of all peptides used in the present example are shown in Table 2.

TABLE 2

| Name | Sequence | SEQ ID NO |
|---|---|---|
| Decoy peptide 1 (TIP1 W/O CPP) | SHCRVLLI | 1 |
| TIP1 | RQIKIWFQNRRMKWKK SHCRVLLI | 3 |
| Decoy peptide 2 (TIP2 W/O CPP) | TIPLLS | 5 |
| TIP2 | RQIKIWFQNRRMKWKK<u>TIPLLS</u> | 6 |
| CPP | RQIKIWFQNRRMKWKK | 9 |

* Decoy peptide sequences are underlined.

1-2. Cell Culture and Preparation

HEK-Blue™-hTLR4 cells (InvivoGen, San Diego, Calif., USA) were added to DMEM (Dulbecco's modified Eagle's medium) (Thermo Fisher Scientific Inc.) supplemented with 1% penicillin/streptomycin, 10% fetal bovine serum (FBS) (Thermo Fisher Scientific Inc., Waltham, Mass., USA), and 0.2% normocin (InvivoGen), and culture was performed. RAW 264.7 cells (Korean Cell Line Bank, Seoul, Korea), which are mouse macrophages, were added to low-glucose DMEM supplemented with 1% penicillin/streptomycin, and 10% FBS (Thermo Fisher Scientific, Inc.), and culture was performed. THP1 cells, which are human monocytes, were cultured in RPMI 1640 supplemented with 1% penicillin/streptomycin, 10% FBS (Thermo Fisher Scientific, Inc.), and then were induced to differentiate into macrophages for 24 hours using 10 nM phorbol 12-myristate 13-acetate (PMA) (Sigma-Aldrich Co. LLC., St. Louis, Mo., USA). hPBMC cells (PromoCell, Heidelberg, Germany), which are human peripheral blood monocytes, were cultured in RPMI 1640 (Thermo Fisher Scientific Inc.) supplemented with 2.05 mM L-glutamine, 1% penicillin/streptomycin, and 10% FBS. mBMDM cells, which are mouse bone marrow-derived macrophages, were cultured in DMEM (Thermo Fisher Scientific Inc.) supplemented with 1% penicillin/streptomycin and 10% FBS. All cells were cultured in a culture system (Thermo Fisher Scientific Inc.) under a humidified condition at 5% $CO_2$, 37° C., and medium replacement was performed every 16 hours. $PAM_3CSK_4$, Poly(I:C), R848, and CpG-ODN were purchased from Thermo Fisher Scientific, Inc.; FSL-1 was purchased from InvivoGen; LPS (*Escherichia coli* 0111: B4) and ATP were purchased from Sigma-Aldrich Co. (St. Louis, Mo., USA); and all peptides used in the experiments were synthesized by and purchased from Peptron, Inc. (Daejeon, Korea).

Example 2. Assay Methods 2-1. MTT Assay

HEK-Blue™-hTLR4 cells were dispensed into 96-well plates (BD Biosciences, San Jose, Calif., USA) to a cell number of $5 \times 10^4$ cells/well, and RAW264.7 cells were dispensed thereinto to a cell number of $2 \times 10^5$ cells/well. Incubation was performed overnight. Subsequently, MTT assay was performed using 1-(4,5-dimethylthiazol-2-yl)-3,5-diphenylformazan (MTT) solution (Sigma-Aldrich Co. LLC).

2-2. Assay for SEAP Activity

HEK-Blue™-hTLR4 cells were dispensed into 24-well plates (BD Biosciences) to a cell number of $2 \times 10^5$ cells/well, and incubation was performed overnight. The next day, the culture was removed and medium replacement was performed. Then, a portion (200 μl) of the culture was transferred to a microcentrifuge tube and heated at 65° C. for 10 minutes using a heating block (FINEPCR. Co., Seoul, Korea). Subsequently, the culture was transferred to 96-well plates (BD Biosciences), and absorbance was measured at 405 nm using the HEK-Blue™ detection kit (InvivoGen) and a microplate reader spectrophotometer (Molecular Devices Inc., Silicon Valley, Calif., USA), to analyze an expression level of SEAP (secreted alkaline phosphatase).

2-3. Western Blotting

In order to perform Western blotting, a pre-protein extraction solution (M-PER, Thermo Fisher Scientific Inc.) was mixed with a protease and phosphatase inhibitor mixture, and was added to RAW 264.7 cell or hPBMC cell pellets. The pellets were cooled for 10 minutes, and then the lysates were centrifuged at 16000×g for 10 minutes. Then, NE-PER nuclear and cytoplasmic extraction reagents (Thermo Fisher Scientific Inc.) were used to extract cytoplasmic and nuclear proteins, respectively, and a BCA kit (Sigma-Alderich Co. LLC) was used to measure concentrations of the proteins. Subsequently, the same amounts of proteins were developed on SDS-polyacrylamide gels, and electrophoresis was performed using the Mini-PROTEAN Tetra Cell two-dimensional electrophoresis system (Bio-Rad Laboratories, Hercules, Calif., USA). The membrane was immunoblotted with primary antibodies by gentle shaking overnight at a temperature of 4° C. (in which the primary antibodies were antibodies against p-p65, p-JNK, p-IRF3, ERK, p38, and human IL-1β (Cell Signaling Technology Inc., Danvers, Mass., USA); p-ERK, p-p38, IκB-α, JNK, ATF3, COX2, caspase-1, and β-actin (Santa Cruz Biotechnology Inc., Santa Cruz, Calif., USA); iNOS (BD Biosciences); IL-6 and mouse IL-1β (R&D Systems Inc., Minneapolis, Minn., USA); TNF-α (Thermo Fisher Scientific, Inc.); NLRP3 (Adipogen, San Diego, Calif., USA)). Then, after thorough shaking with PBST, the membrane was incubated with anti-mouse/-rabbit HRP-conjugated secondary antibodies (Thermo Fisher Scientific Inc.) for 2 hours; and the proteins were detected with SuperSignal West Pico ECL solution (Thermo Fisher Scientific Inc.) and were visualized with the Fuji LAS-3000 system (Fujifilm, Tokyo, Japan).

2-4. Confocal Microscopy

RAW 264.7 cells and THP1 cells were dispensed into 24-well plates to a cell number of 2×10$^5$ cells/well, and then grown in an incubator overnight. Subsequently, combined treatment with TIP1 and LPS was performed. After 24 hours, the RAW 264.7 cells and the THP1 cells were fixed with 3.7% formaldehyde (Sigma-Aldrich Co. LLC) for 15 minutes, and immersed into 0.2% Triton X-100 (AMRESCO, Solon, Ohio, USA) for 15 minutes. Then, washing with PBS was performed three times and blocking with 2% BSA solution was performed. The blocked cells were incubated for 2 hours with TIP1-FITC (25 μM; Peptron, Inc., Daejeon, Korea), p-p65, TLR4, Myd88, TOM20 (1:1000; Santa Cruz Biotechnology Inc.), and NLRP3 (Adipogen) antibodies. Then, washing with PBS was performed three times. Subsequently, the cells were incubated with AlexaFluor 408 and/or 488 and/or 546-conjugated secondary antibodies (Invitrogen, Carlsbad, Calif., USA) for 1 hour, and washed three times with PBS. Subsequently, the cells were stained at room temperature for 15 minutes using 5 μM Hoechst 33258 (Sigma-Aldrich Co.), and the number of the fluorescently stained cells was counted using a confocal laser scanning microscope (LSM-700, Carl Zeiss MicroImaging GmbH). The images were analyzed using Zen 2009 software.

2-5. Assay for TNF-α, IL-6, IFN-β, and IL-1β

RAW 264.7 cells, THP1 cells, and mBMDM cells were dispensed into 96-well plates to a cell number of 2×10$^5$ cells/well, or into 24-well plates to a cell number of 5×10$^5$ cells/well. Incubation was performed overnight. Subsequently, combined treatment with TIP1 and LPS was performed. After 24 hours, secretion levels of IFN-β, IL-6, and TNF-α were measured using a LEGEND MAX™ Mouse IL-6 pre-coated ELISA kit (BioLegend), Mouse IL-6 Platinum ELISA (eBiosciences), and a Mouse TNF alpha ELISA Ready SET-Go! kit (eBiosciences). Absorbance was measured at 450 nm using a microplate reader spectrophotometer (Molecular Devices), and the results were analyzed using Softmax Pro 5.3 software (Molecular Devices Inc.).

2-6. Assay for Intracytoplasmic NO and ROS

RAW 264.7 cells were dispensed into 6-cm dishes (SPL Life Sciences, Pocheon, Korea) to a cell number of 1×10$^6$ cells/well and incubation was performed overnight. Subsequently, treatment with TIP1 was performed and respective staining with DAF-FM and DCF-DA (Thermo Fisher Scientific, Inc.) was performed. Then, incubation was performed for 1 hour. Thereafter, the cells were collected by centrifugation at 200×g for 5 minutes, transferred to brown tubes, and stored in PBS at a temperature of 4° C. The intensities of DAF-FM, DCF-DA fluorescent materials were measured using FACSAria III with Diva software (BD Biosciences), and quantified.

2-7. Assay for NO Secretion Level

RAW 264.7 cells and mBMDM cells were dispensed into 96-well plates (BD Biosciences) to a cell number of 2×10$^5$ cells/well and incubated overnight. Then, a NO level of the culture supernatant was measured using a NO detection kit (iNtRON Biotechnology Inc., Seongnam, Korea). Absorbance was measured at 550 nm using a microplate reader spectrophotometer (Molecular Devices Inc.), and the results were analyzed using Softmax Pro 5.3 software (Molecular Devices Inc.).

2-8. Surface Plasmon Resonance (SPR) Assay

Surface plasmon resonance assay was performed using a ProteOn XPR36 instrument (Bio-Rad Laboratories, Inc.) with a ProteOn NLC sensor chip. Specifically, a synthetic peptide encoding BB-loop (RDFIPGVAIAA) (SEQ ID NO: 54) and C-terminal region (EGTVGTGCNWQEATSI) (SEQ ID NO: 55) of the TIR domain was immobilized on the surface of the NLC sensor chip using NeutrAvidin bound to the GLC polymer layer. For a control, PBS supplemented with 0.05% Tween 20, which is a running buffer, was flowed. Various types of TIP1, TIP1-2, and TIP1-3 (50 μM), and different concentrations of TIP1 (12.5, 25, and 50 μM) were flowed onto the chip to identify their binding affinity with the immobilized peptide. After the measurement, the surface of the sensor chip was regenerated using 0.85% phosphoric acid or PBST. Dissociation constants were calculated using ProteOn manager™ software (version 2.0), and data acquired from various doses of TIP1 were grouped to match kinematic rate constants ($K_a$ and $K_d$). The equilibrium dissociation constant $K_D$ was calculated using the equation $K_D=K_d/K_a$.

Experimental Example 1. Identification of TLR4-Binding Affinity of TIPs

In order to identify TLR4-binding affinity of the TIPs (TIP1, TIP2) prepared in Example 1-1, NF-κB activity was measured in HEK-Blue™-hTLR4 cells cultured in Example 1-2. To this end, the inducible secreted embryonic alkaline phosphatase (SEAP) reporter gene was placed under the control of an IL-12 p40 minimal promoter (IL-12 p40 is produced by activation of NF-κB and AP-1 (activator protein 1) after stimulation of TLR4) which contains sites where DNAs of NF-κB and AP-1 bind. Then, HEK-Blue™-hTLR4 cells were treated with varying concentrations of TIP or TIP (TIP W/O CPP), to which CPP is not linked, at 12.5, 25, 50 µM, and then an average value of SEAP activity was calculated to measure TLR4 activity. The results are illustrated in FIGS. 1(a) and 1(b).

Figure 1B:
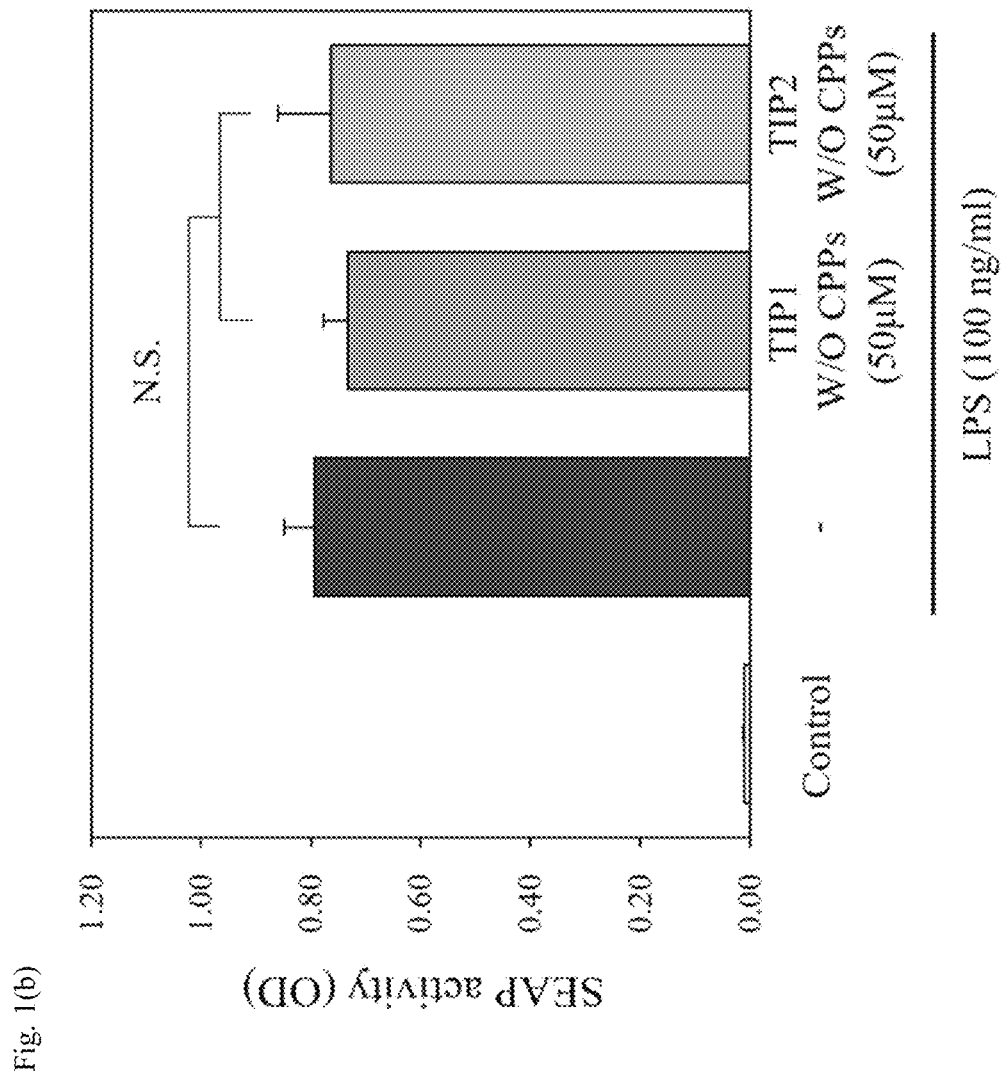
FIG. 1(b) illustrates results obtained by measuring SEAP activity depending on TIP1 (TIP1 W/O CPP) and TIP2 (TIP2 W/O CPP) to which a CPP sequence was not linked.

As illustrated in FIG. 1(a), it was identified that in a case where only TIP was added, no great change was observed in SEAP activity; however, in a case where treatment with TIP was performed, and then TLR4 was stimulated with LPS, unlike TIP2, TIP1 decreased LPS-induced SEAP activity in a concentration-dependent manner. In addition, as illustrated in FIG. 1(b), it was identified that in a case where the CPP sequence was not linked, neither TIP1 (TIP1 W/O CPP) nor TIP2 (TIP2 W/O CPP) changed SEAP activity. From these results, it was identified that TIP1 of the present invention, once linked to CPP and thus translocated into a cell, interferes with adapter molecules downstream of the signaling pathway, and blocks activation of the TLR4-mediated signaling pathway induced by LPS, which allows TIP1 to be used as an effective TLR4 inhibitor.

Experimental Example 2. Inhibitory Effect of TIP1 on TLR Signaling Pathway In Vitro TLR4-mediated responses induced by LPS induce direct interactions between the TIR domain of TIRAP and MyD88, thereby activating MyD88-dependent signaling pathways. In addition, the TLR4-mediated responses induce interactions between the TIR domain of TRAM and TRIF, thereby also activating MyD88-independent signaling pathways. In the MyD88-dependent signaling pathways, initial activity of NF-κB induces secretion of pro-inflammatory cytokines such as tumor necrosis factor alpha (TNF-α) and interleukin 6 (IL-6). On the other hand, in the MyD88-independent signaling pathways, late secretory responses of type I interferons (IFNs) such as IFN-α and IFN-β, including activity of IRF3 and 7, are induced. In order to examine an effect of TIP1 on TLR4 signaling pathways, the present inventors subjected RAW 264.7 cells to treatment with LPS, and then conducted the following experiments.

2-1. Western Blotting of NF-κB and MAPK

Western blotting was performed according to the method described in Example 2-3 to identify an effect of TIP1 prepared in Example 1-1 on activity of NF-κB and MAPK. The results are illustrated in FIGS. 2(a) and 2(b).

Figure 2A:
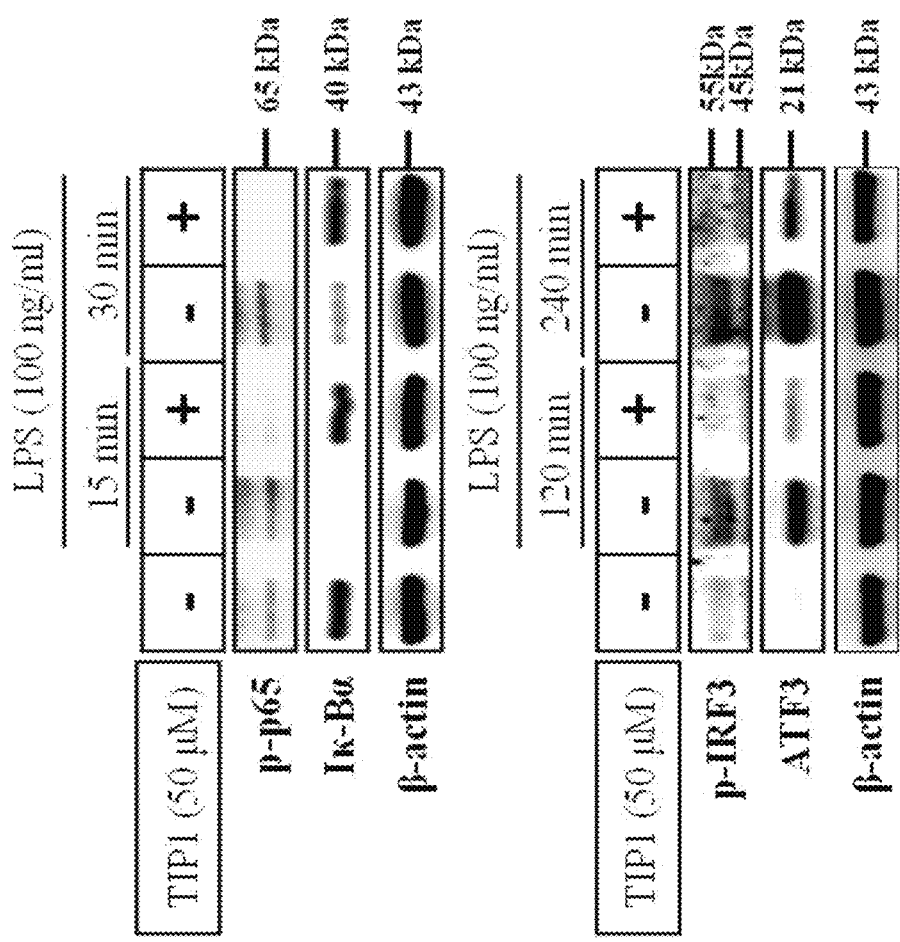
FIG. 2(a) illustrates results obtained by identifying, through Western blotting, NF-κB (p65) and IRF3 activity in a case where RAW 264.7 cells, which were mouse macrophages, were treated with TIP1 together with LPS.
Figure 2B:
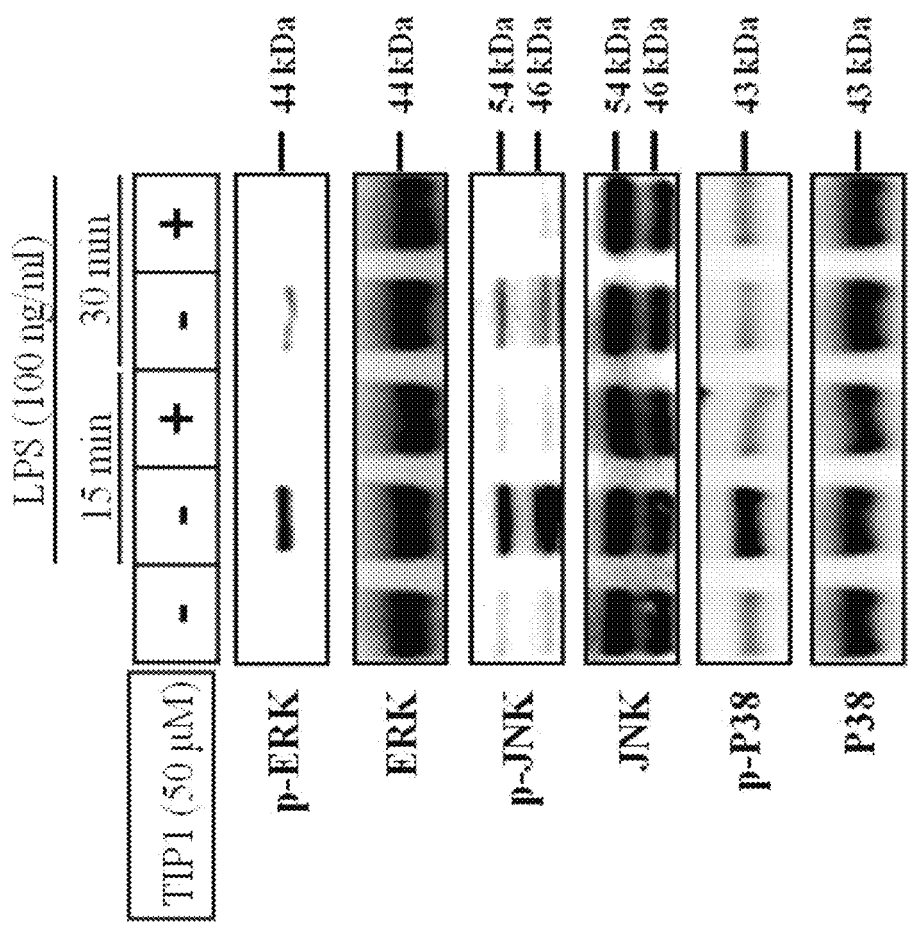
FIG. 2(b) illustrates results obtained by identifying, through Western blotting, MAPK activity under the same conditions.

As illustrated in FIG. 2(a), it was identified that in a case where RAW 264.7 cells, which were mouse macrophages and used as a control, were treated with only LPS, NF-κB activity was increased so that Iκ-Bα was degraded and activity of IRF3 and ATF3 was increased; however, it was identified that in a case of being treated with LPS together with TIP1, NF-κB activity was inhibited so that degree of degradation of Iκ-Bα, and activity of IRF3 and ATF3 were decreased. In addition, as illustrated in FIG. 2(b), it was identified that in a case of being treated with only LPS, MAPK activity was increased so that ERK, JNK, and p38 were phosphorylated; however, it was identified that in a case of being treated with LPS together with TIP1, MAPK activity was inhibited so that degree of phosphorylation of the enzymes was decreased. From these results, it was identified that TIP1 according to the present invention binds to the TIR domain of TLR4, thereby inhibiting MyD88-dependent signaling pathways induced by LPS as well as MyD88-independent signaling pathways.

2-2. Identification of Activation of NF-κB

Confocal laser microscopy was performed according to the method described in Example 2-4, to identify an effect of TIP1 prepared in Example 1 on NF-κB activity. The results are illustrated in FIG. 3.

Figure 3:
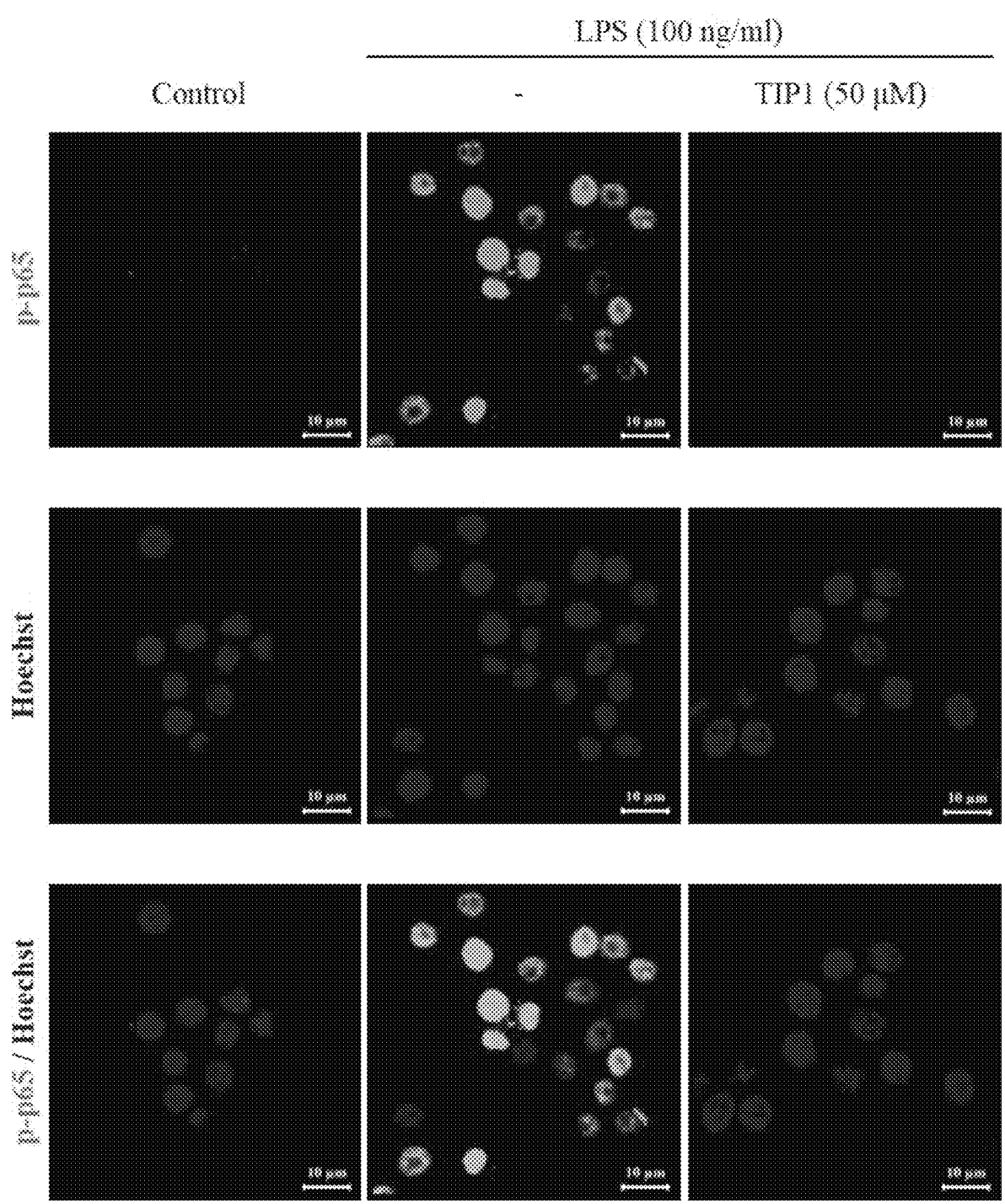
FIG. 3 illustrates results obtained by identifying NF-κB activity (p-p65, green) with a confocal laser scanning microscope in a case where RAW 264.7 cells, which were mouse macrophages, were treated with TIP1 together with LPS, indicating that migration of p-p65 into the nucleus was blocked by TIP1.

As illustrated in FIG. 3, it was identified that in a case of being treated with only LPS, activated NF-κB (p-p65) was expressed in the nucleus; however, it was identified that in a case of being treated with LPS together with TIP1, NF-κB activity was decreased due to a decrease of LPS-induced p65 phosphorylation level in the nucleus.

Experimental Example 3. Effect of TIP1 on Secretion of Cytokines, NO, and ROS

The following experiments were conducted to identify whether in a case where RAW 264.7 cells, which are mouse macrophages, cultured in Example 1-2 are treated with TIP1 prepared in Example 1-1, secretion of cytokines (TNF-α, IL-6, IFN-β) and nitric oxide (NO), and generation of reactive oxygen species (ROS) in the cytoplasm are inhibited.

3-1. Effect of TIP1 on Cytokine Secretion

TNF-α, IL-6, IFN-β levels in the culture supernatant of RAW 264.7 cells were measured using mouse TNF-α, IL-6, IFN-β Ready-SET-Go! ELISA kits according to the method described in Example 2-5. The results are illustrated in FIGS. 4(a)-4(c).

Figure 4A:
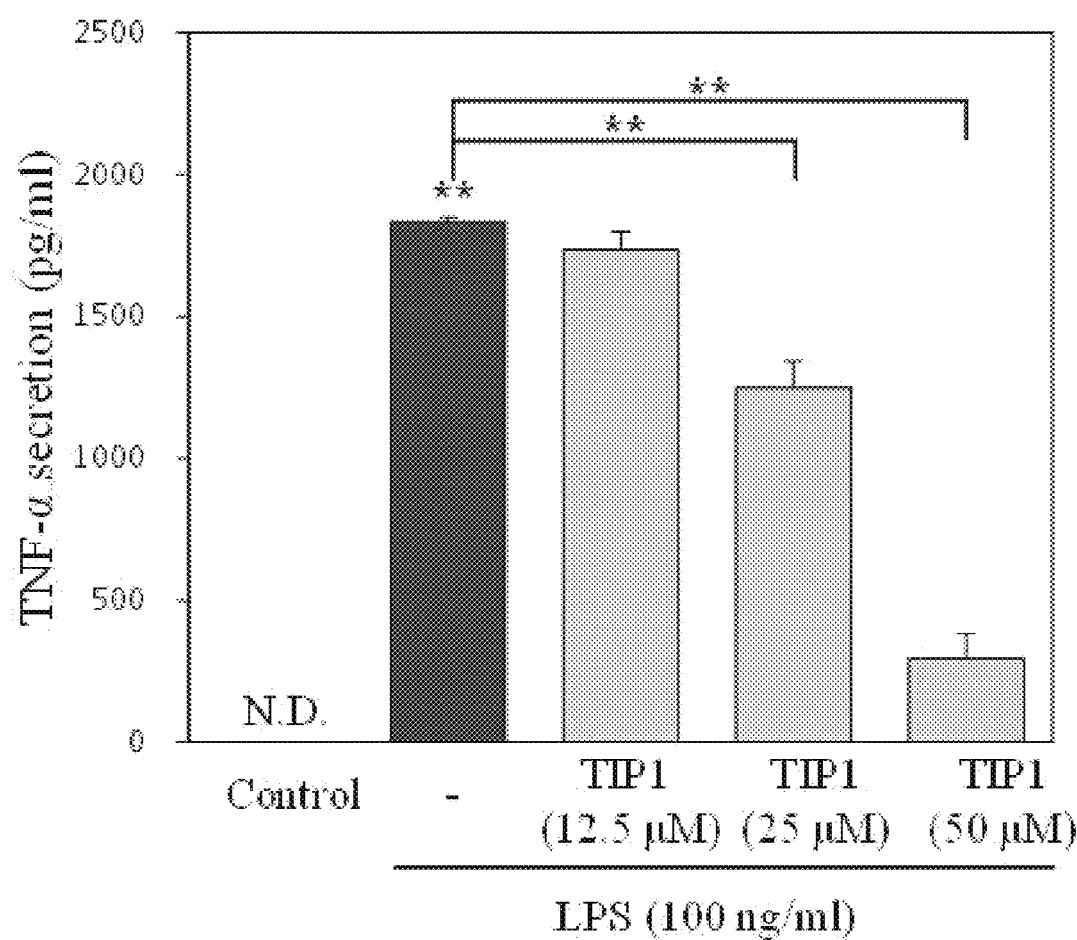
FIGS. 4(a)-4(c) illustrate results obtained by identifying cytokine secretion levels in a case where RAW 264.7 cells, which were mouse macrophages, were treated with different concentrations of TIP1 together with LPS.
Figure 4B:
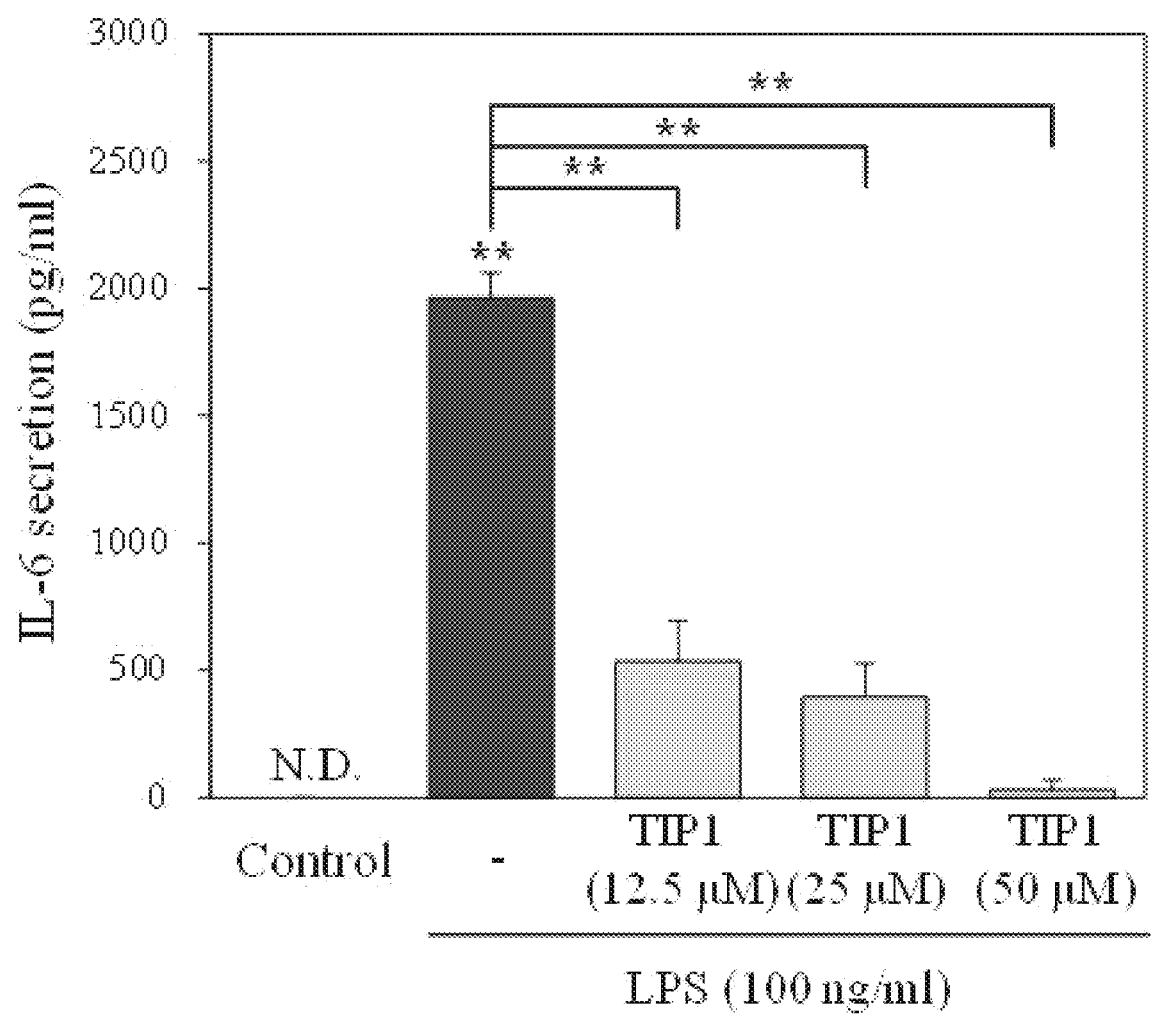
Figure 4C:
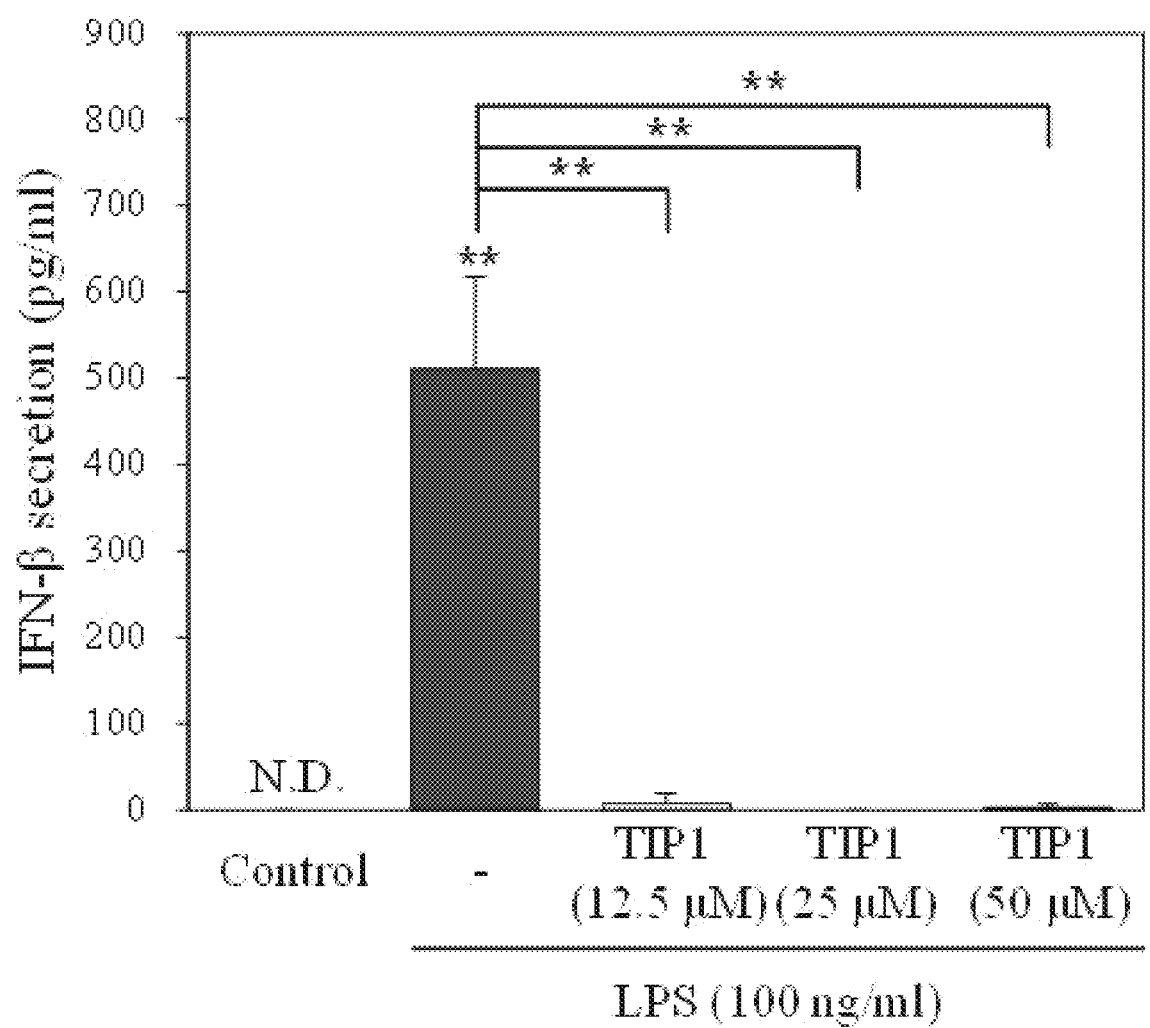

As illustrated in FIGS. 4(a)-4(c), it was identified that in a case where combined treatment with TIP1 and LPS was performed, secretion of TNF-α, IL-6, IFN-β was decreased in a concentration-dependent manner. From these results, it was identified that TIP1 according to the present invention inhibits LPS-induced secretion of cytokines.

3-2. Effect of TIP1 on Secretion of NO and ROS

In order to identify an effect of TIP1 on generation of NO and reactive oxygen species (ROS) in the cytoplasm, according to the method described in Examples 2-6, RAW 264.7 cells were treated with TIP1 and were stained with DAF-FM (Invitrogen Corp., CA, USA) and DCF-DA (Invitrogen Corp.), respectively, to quantify cytosolic NO and ROS, respectively. In addition, according to the method described in Example 2-7, a NO level in the culture supernatant of RAW 264.7 cells was measured using a NO detection kit. The results are illustrated in FIGS. 5(a)-5(c).

Figure 5A:
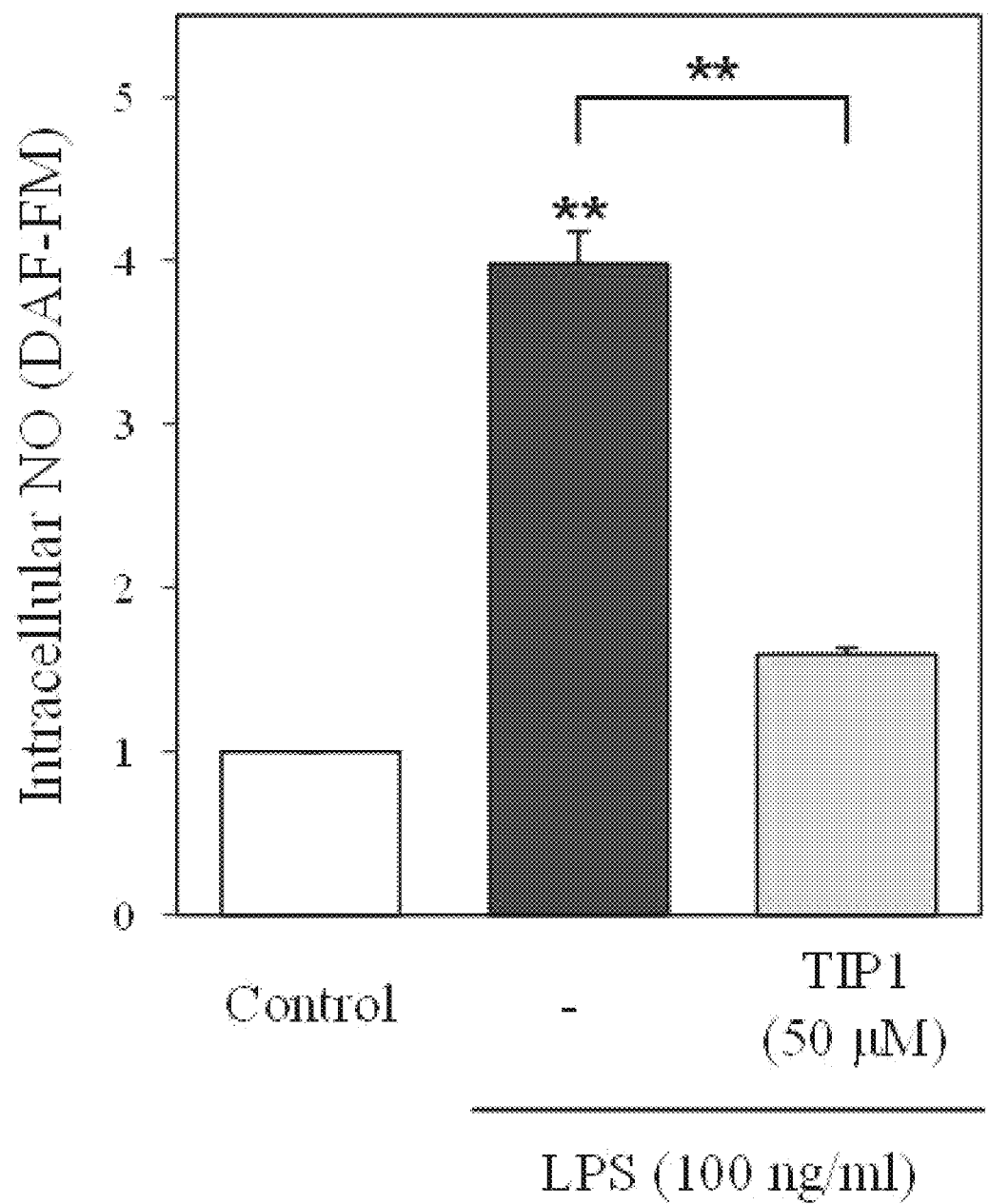
FIGS. 5(a)-5(c) illustrate results obtained by identifying generation levels of NO and ROS in a case where RAW 264.7 cells, which were mouse macrophages, were treated with TIP1 together with LPS.
Figure 5B:
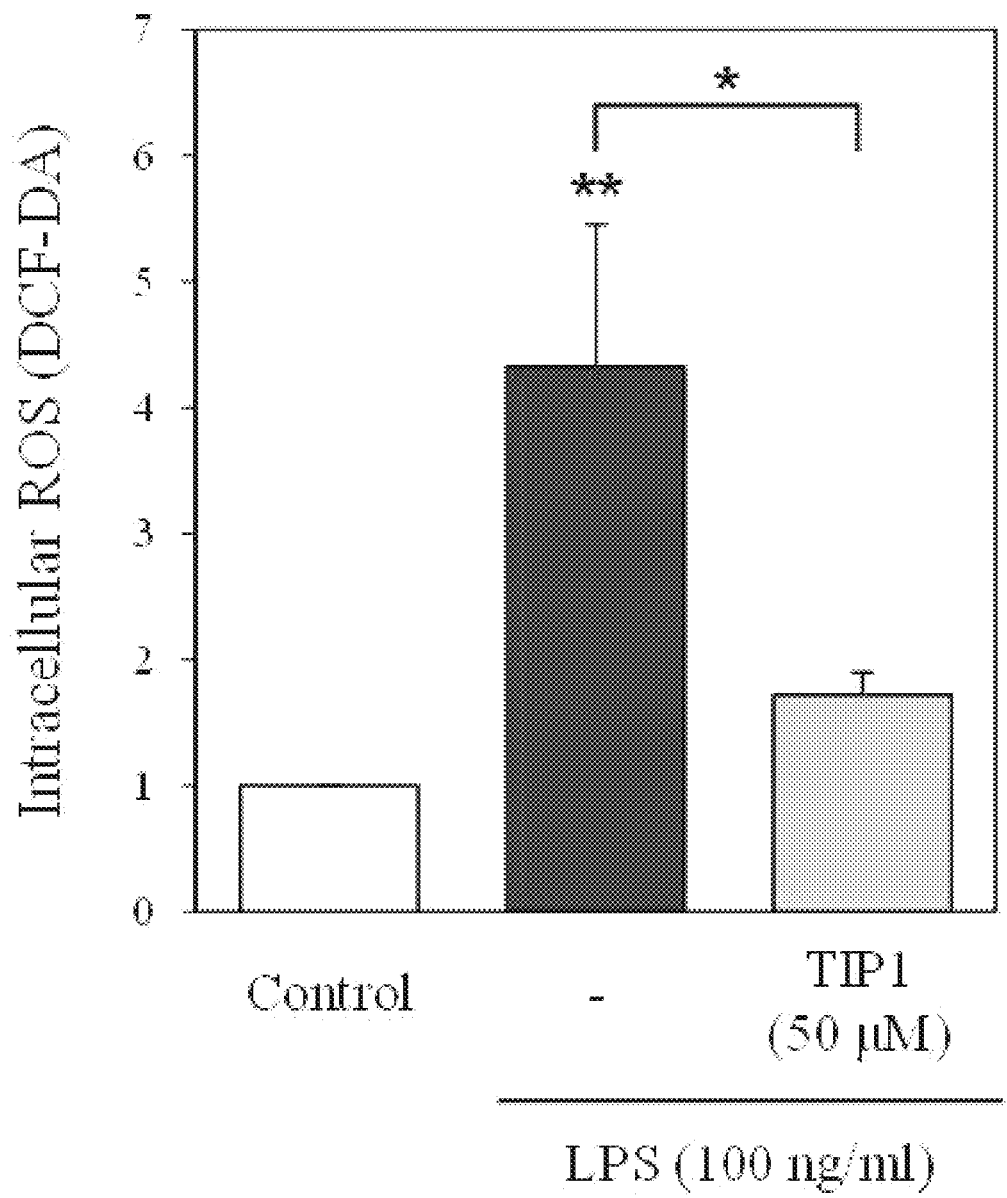
Figure 5C:
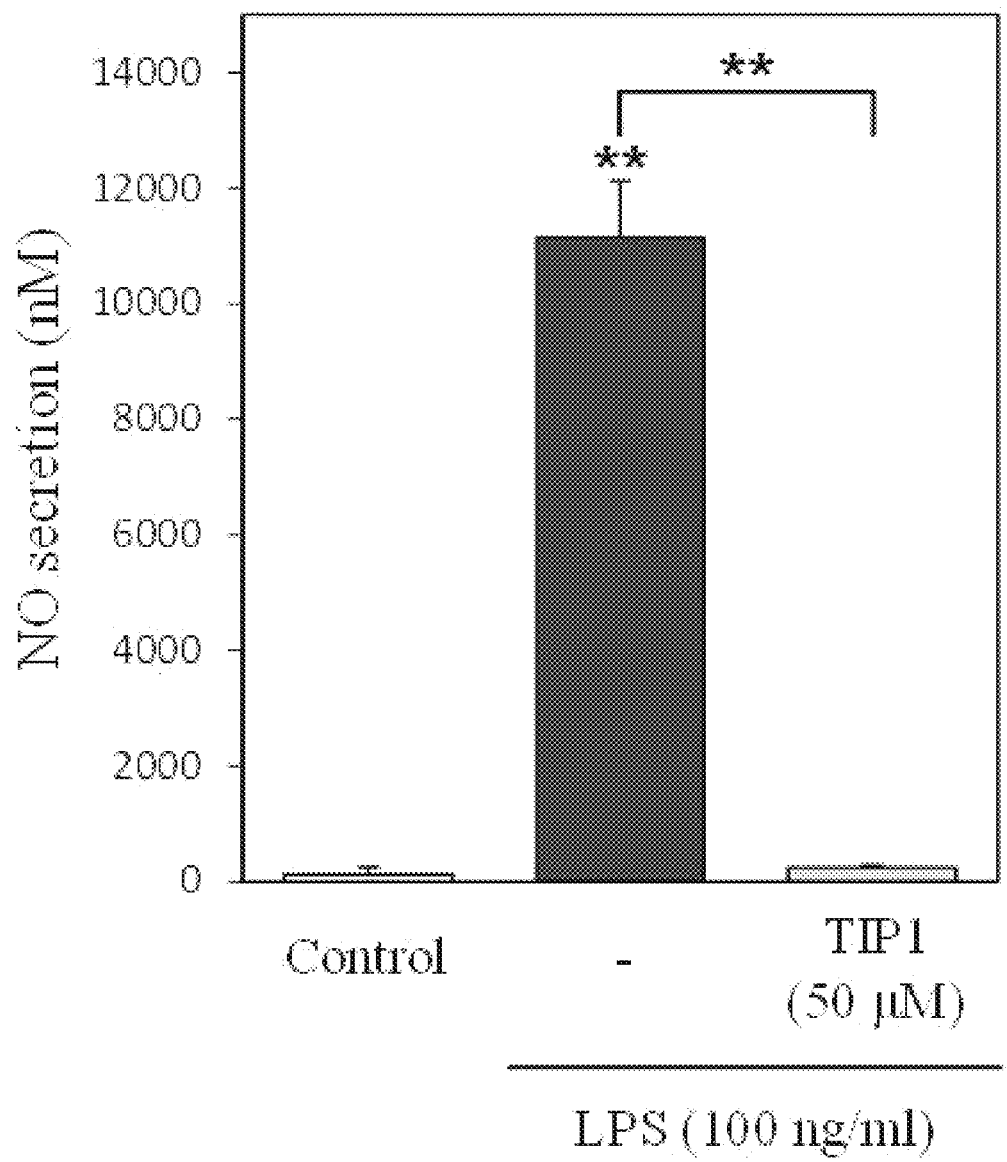
Figure 6A:
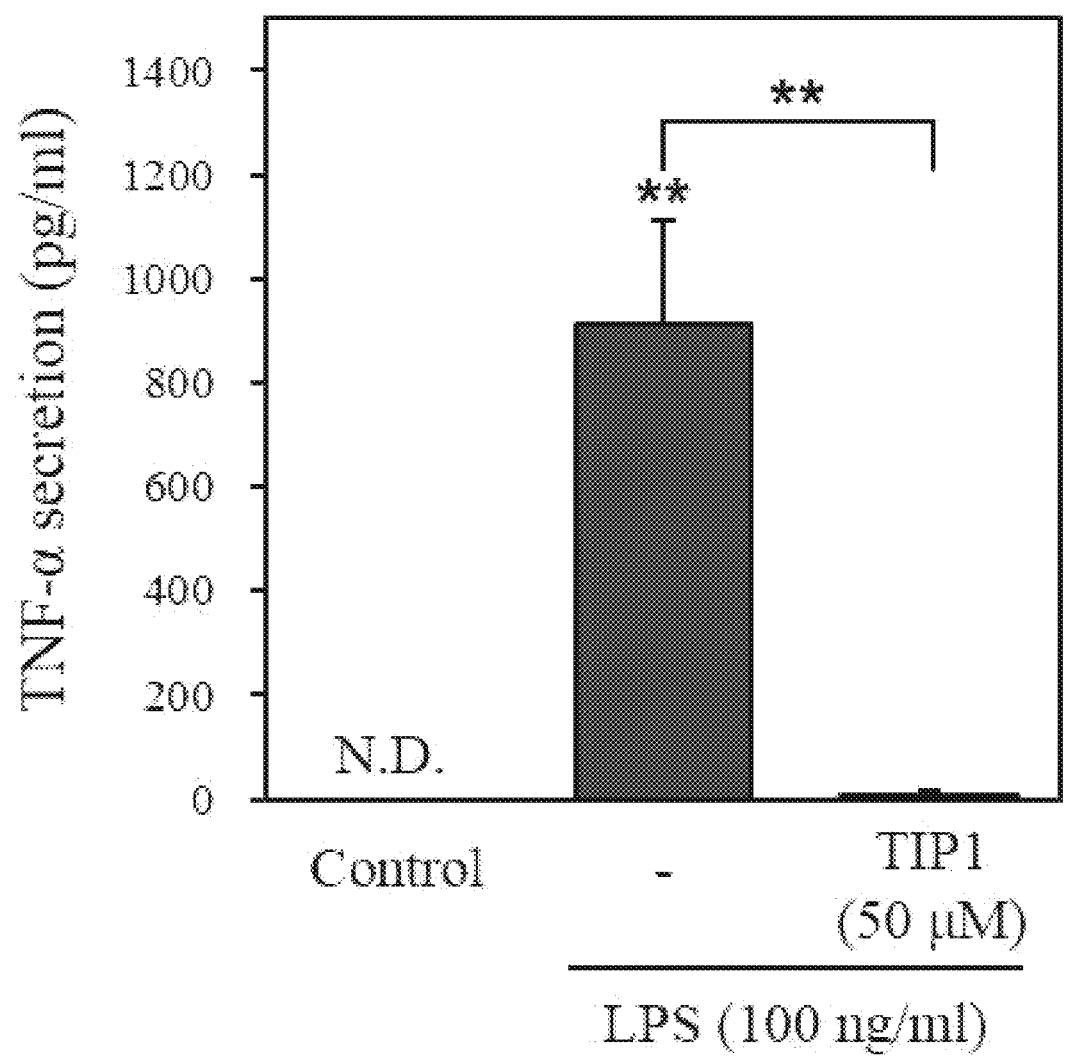
FIGS. 6(a)-6(d) illustrate results obtained by identifying generation levels of cytokines and NO in a case where mouse bone marrow-derived macrophage (mBMDM) cells were treated with TIP1 together with LPS.
Figure 6B:
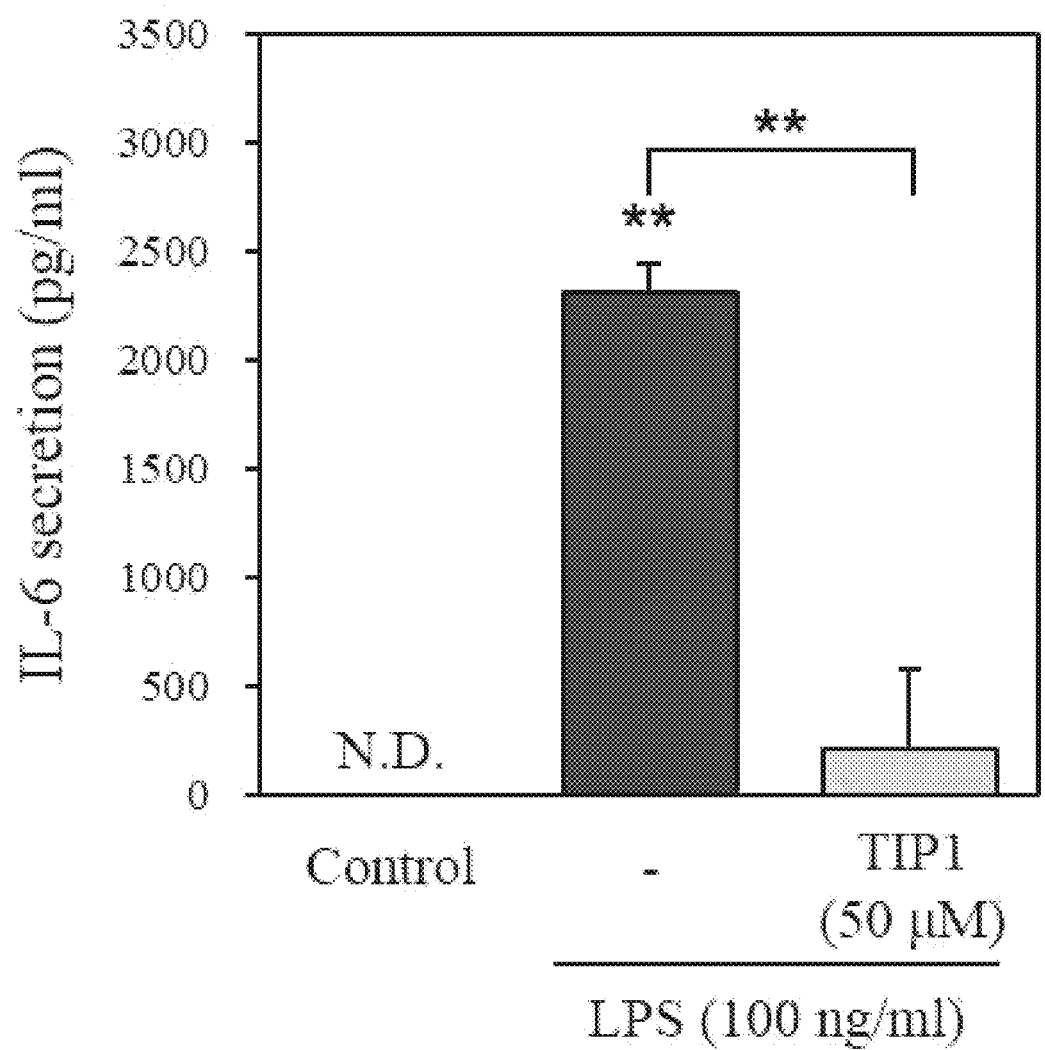
Figure 6C:
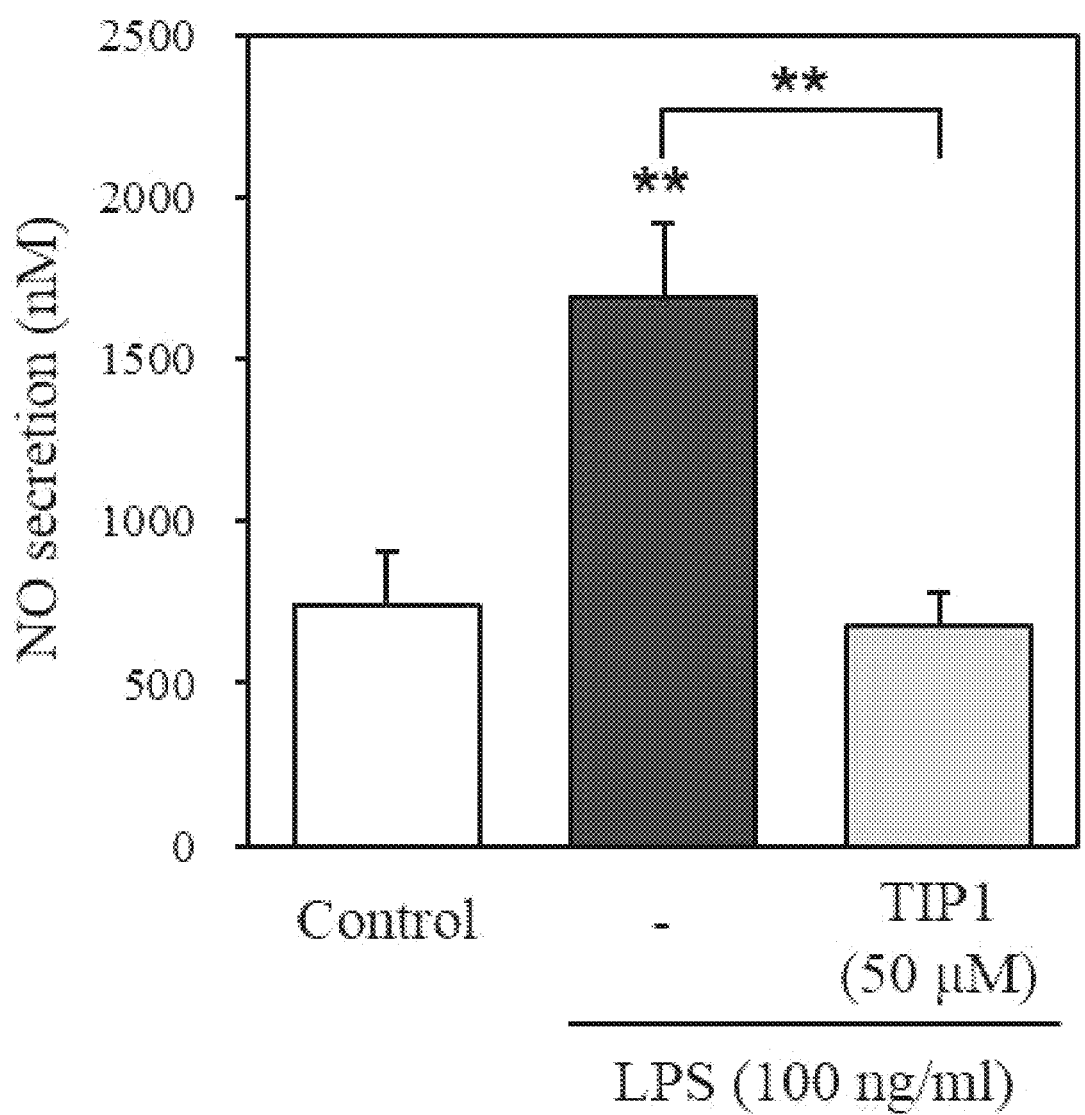
Figure 6D:
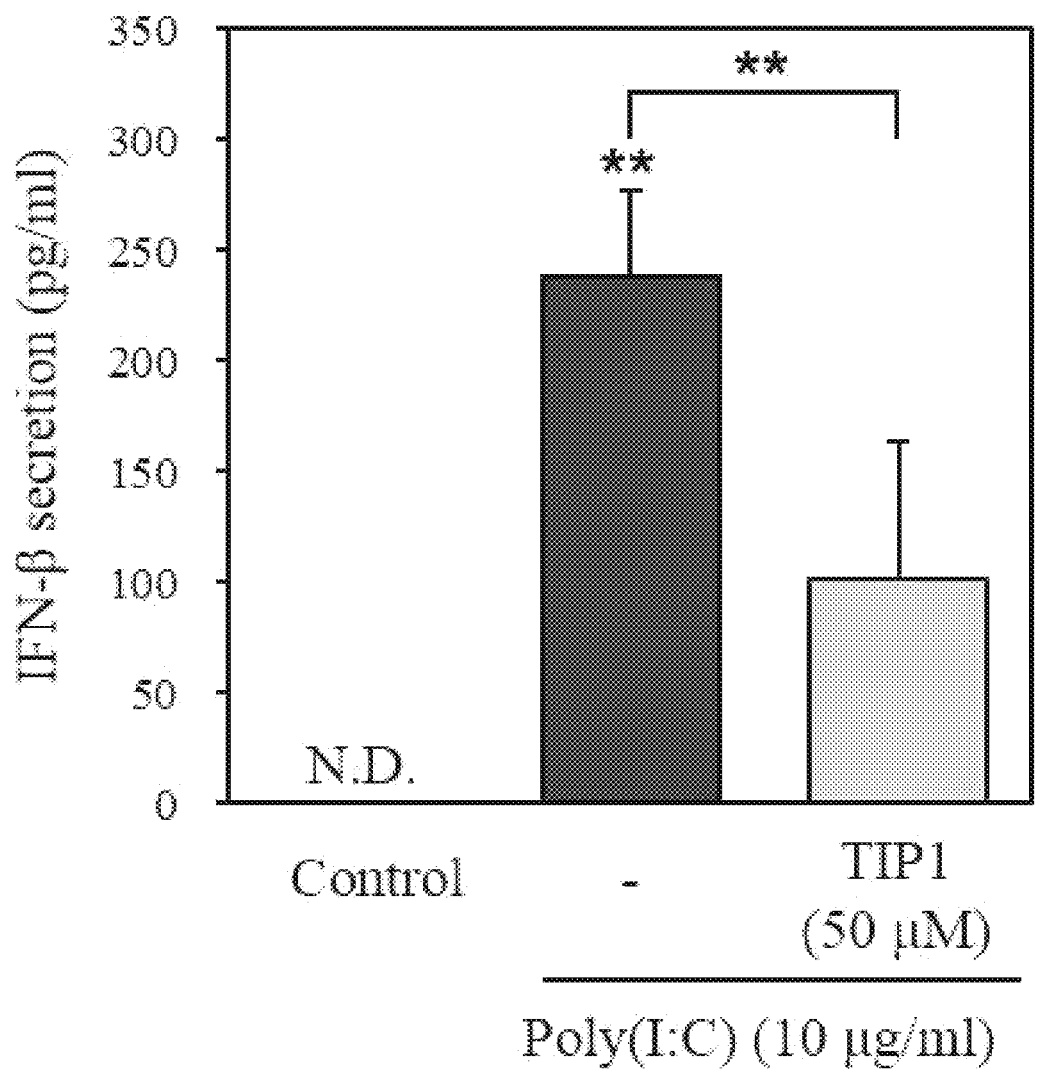

As illustrated in FIGS. 5(a) to 5(c), it was identified that in a case where combined treatment with TIP1 and LPS was performed, TIP1 effectively decreased extracellular secretion of NO as well as generation levels of NO and ROS in the cytoplasm. From these results, it was identified that TIP1 according to the present invention inhibits LPS-induced oxidative stress.

Experimental Example 4. Identification of Effect of TIP1 on Primary Cells

The following experiments were conducted to identify whether in a case where mBMDM cells, which are mouse bone marrow-derived macrophages, and hPBMC cells, which are human peripheral blood mononuclear cells, cultured in Example 2, are treated with TIP1 prepared in Example 1, secretion of cytokines (TNF-α, IL-6, IFN-β) and nitric oxide (NO), and activation of TLR signaling proteins are inhibited.

4-1. Effect of TIP1 on mBMDM Cells

TNF-α, IL-6, IFN-β levels in the culture supernatant of mBMDM cells were measured using mouse TNF-α, IL-6, IFN-β Ready-SET-Go! ELISA kits according to the method described in Example 2-5, and a NO level in the supernatant was measured according to the method described in Example 2-7. The results are illustrated in FIGS. 6(a)-6(d).

As illustrated in FIGS. 6(a) to 6(d), it was identified that TIP1 decreased LPS-induced secretion levels of TNF-α, IL-6, and NO, and inhibited Poly(I:C)-induced generation of IFN-β. From these results, it was identified that TIP1 according to the present invention inhibits LPS- or Poly(I:C)-induced secretion of cytokines and NO in mouse bone marrow-derived macrophages.

4-2. Effect of TIP1 on hPBMC Cells

In order to identify an effect of TIP1 on activity of NF-κB and MAPK in hPBMC cells, Western blotting was performed according to the method described in Example 2-3, and the proteins were visualized. The results are illustrated in FIG. 7.

Figure 7:
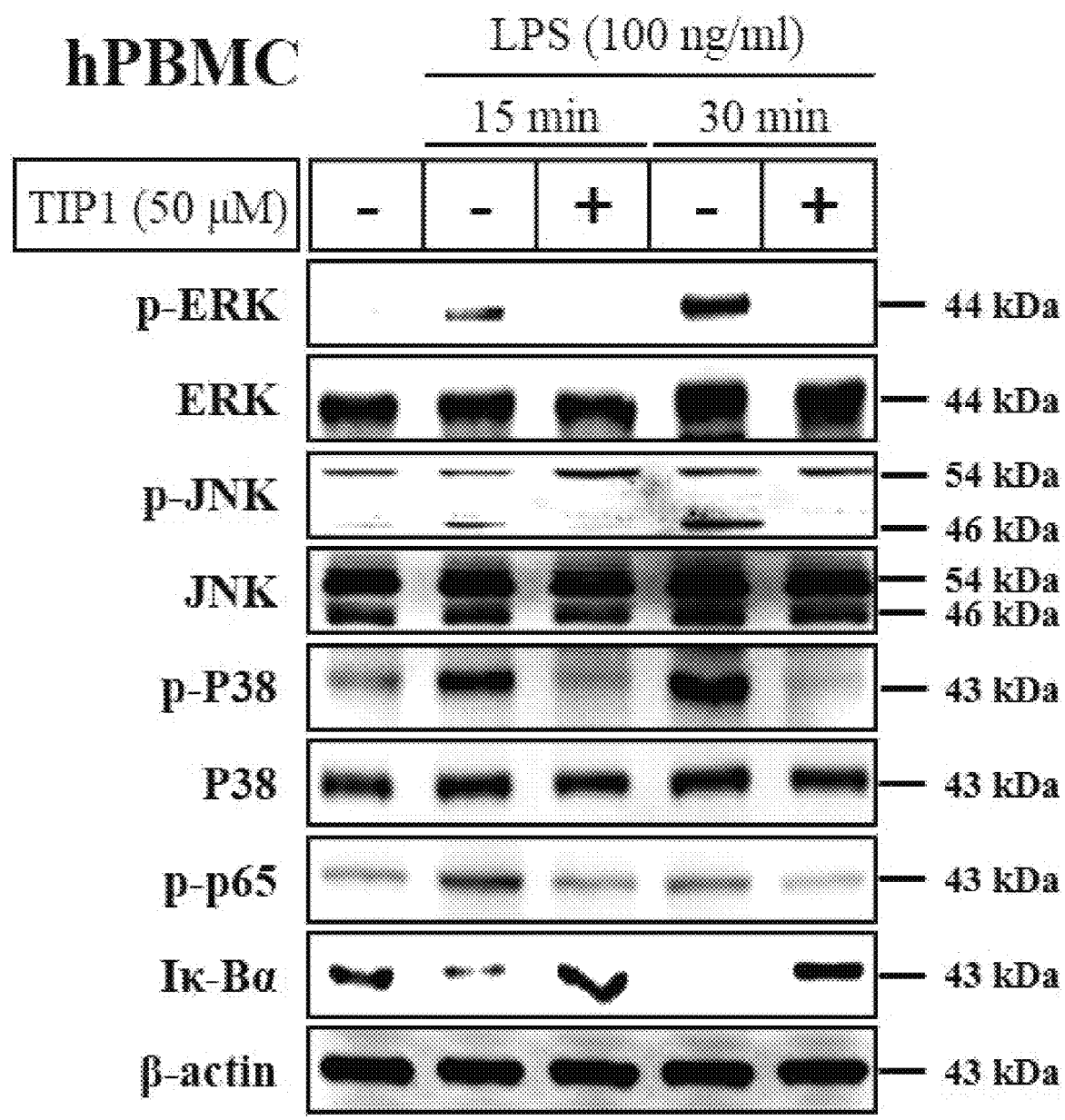
FIG. 7 illustrates results obtained by identifying, through Western blotting, expression levels of p-ERK, ERK, p-JNK, JNK, pp38, p38, p-p65, and Iκ-Bα in human peripheral blood mononuclear cells (hPBMCs) in a case where the cells were treated with TIP1 together with LPS, showing that the expression levels were inhibited by TIP1.

As illustrated in FIG. 7, in a case where hPBMC cells, which are human peripheral blood mononuclear cells and used as a control, were treated with only LPS, NF-κB activity was increased so that Iκ-Bα was degraded, whereas in a case of being treated with LPS together with TIP1, NF-κB activity was inhibited so that Iκ-Bα was less decreased. In addition, it was identified that in a case of being treated with only LPS, MAPK activity is increased so that ERK, JNK, p38 are phosphorylated; however, it was identified that in a case of being treated with LPS together with TIP1, MAPK activity is inhibited so that degree of phosphorylation of the enzymes is decreased.

From these results, it was identified that TIP1 according to the present invention inhibits TLR4 signaling pathways in immortalized cell lines as well as in primary cells directly extracted from animals.

Experimental Example 5. Effect of TIP1 on Other TLR Signaling Pathways

Figure 8:
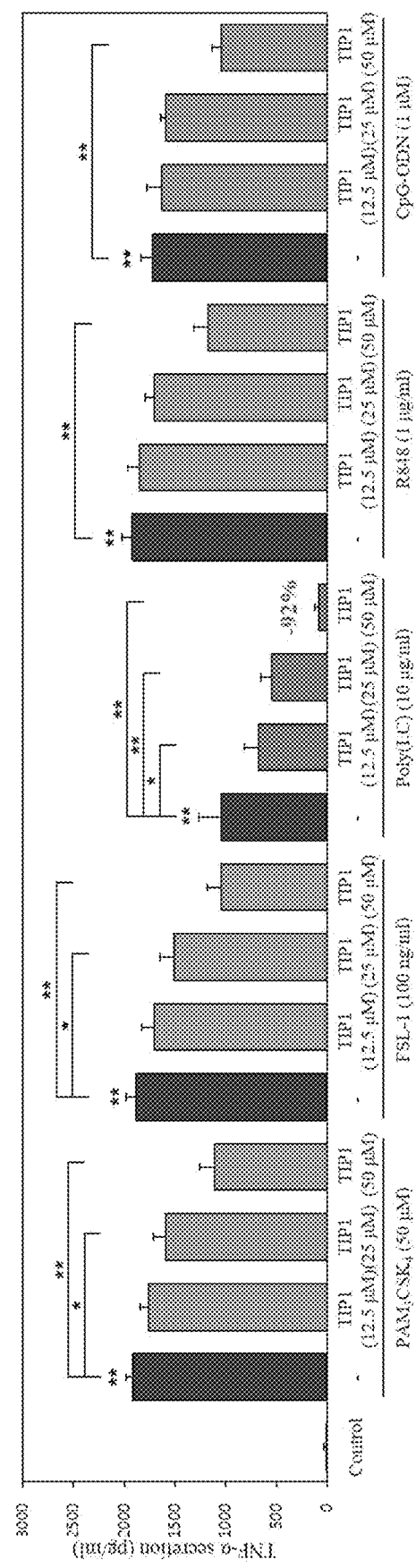
FIG. 8 illustrates results obtained by measuring secretion levels of TNF-α in RAW 264.7 cells, which are mouse macrophages, in a case where the cells were treated with TIP1 together with PAM$_3$CSK$_4$ (TLR1/2), FSL-1 (TLR2/6), Poly(I:C) (TLR3), R848 (TLR7/8), or CpG-ODN (TLR9), which were ligands corresponding to respective TLRs, showing that the secretion levels were inhibited by TIP1.
Figure 9:
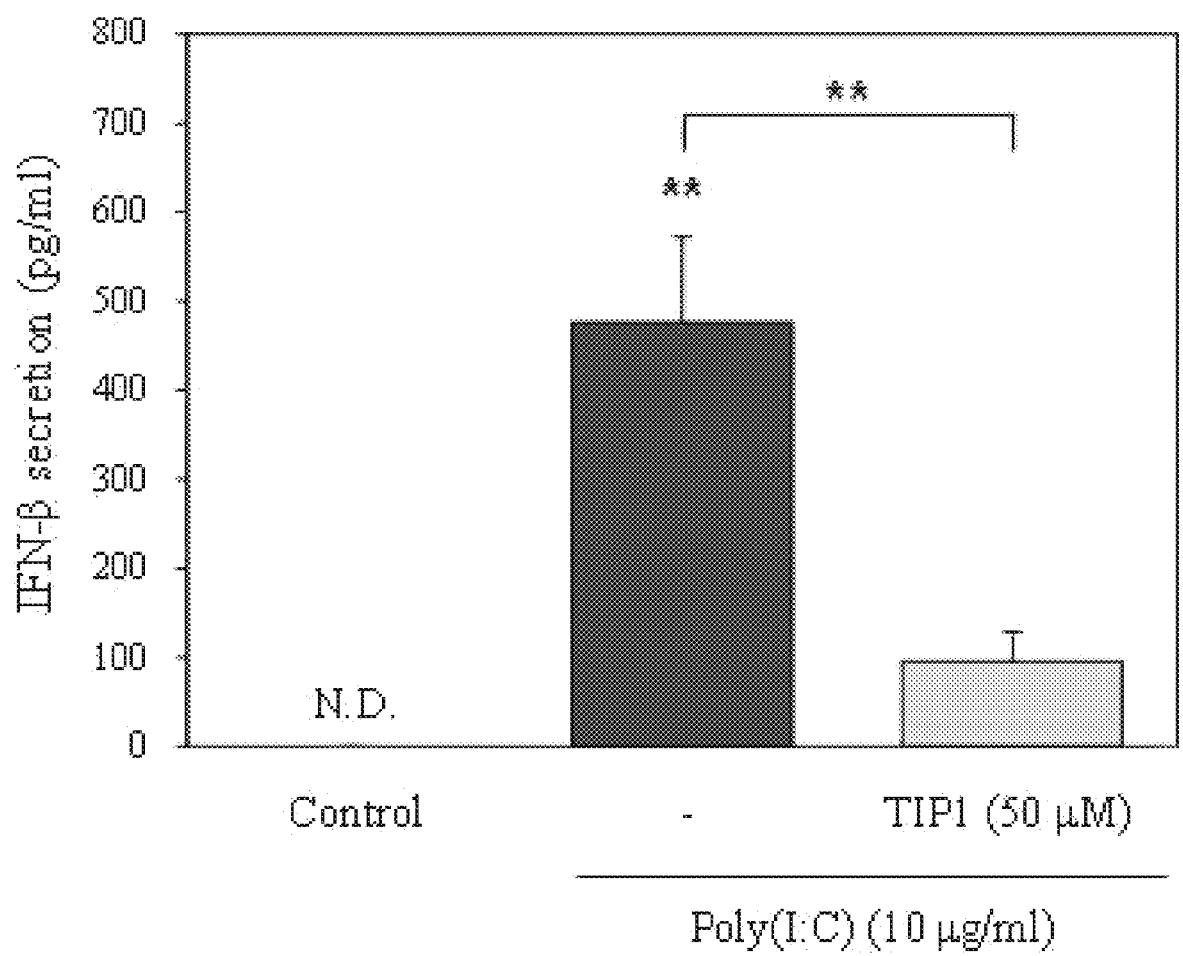
FIG. 9 illustrates results obtained by identifying, through ELISA, a secretion level of IFN-β in a case where RAW 264.7 cells, which were mouse macrophages, were treated with TIP1 together with Poly(I:C), indicating that the secretion level was decreased by TIP1.

In order to identify an effect of TIP1 on signaling pathways of TLR family members other than TLR4, TNF-α levels induced by different TLR ligands in the culture supernatant of RAW 264.7 cells were measured using the method in Example 2-5. The results are illustrated in FIG. 8. In addition, an IFN-β level in the culture supernatant of RAW 264.7 cells was measured using a Ready-SET-Go! ELISA kit. The results are illustrated in FIG. 9.

As illustrated in FIG. 8, it was identified that in a case of being treated with TIP1 together with PAM3CSK4 (TLR1/2) or FSL-1 (TLR2/6) or Poly(I:C) (TLR3) or R848 (TLR7/8) or CpG-ODN (TLR9), a secretion level of TNF-α was decreased; in particular, TIP1 had a high inhibitory effect on TLR3 signaling (92% decrease at 50 μM). In addition, as illustrated in FIG. 9, it was identified that in a case of being treated with TIP1 together with Poly(I:C), a secretion level of IFN-β was decreased. From these results, it was identified that TIP1 according to the present invention has an inhibitory effect on cytokine secretion in TLR1/2, TLR2/6, TLR3, TLR7/8, TLR9 as well as TLR4.

Experimental Example 6. Effect of TIP1 on Degenerative Neurological Diseases

LPS-induced activation of the TLR4 signaling pathway results in NF-κB activity, which immediately leads to expression of NOD-like receptor (NLR), NACHT, LRR and PYD-domains-containing protein 3 (NLRP3), and IL-1β in macrophages. Under these conditions, ATP and potassium efflux agents decrease intracellular potassium levels and induce generation of mature IL-1β by NLRP3 inflammasome.

Taking note of such correlation between activity of the TLR4 signaling pathway and formation of NLRP3 inflammasome, the present inventors subjected THP1 cells, which are human monocytes, and mBMDM THP1 cells, which are mouse bone marrow-derived macrophages, to treatment with LPS/ATP, or to combined treatment with TIP1 and LPS/ATP, and then visualized, through Western blotting, protein expression of NLRP3, pro-caspase-1 (45 kDa), active caspase-1 (10 kDa), pro-IL-1β (35 kDa), and mature IL-1β (17 kDa) according to the method described in Example 2-3. The results are illustrated in FIGS. 10(a) and 10(b).

Figure 11A:
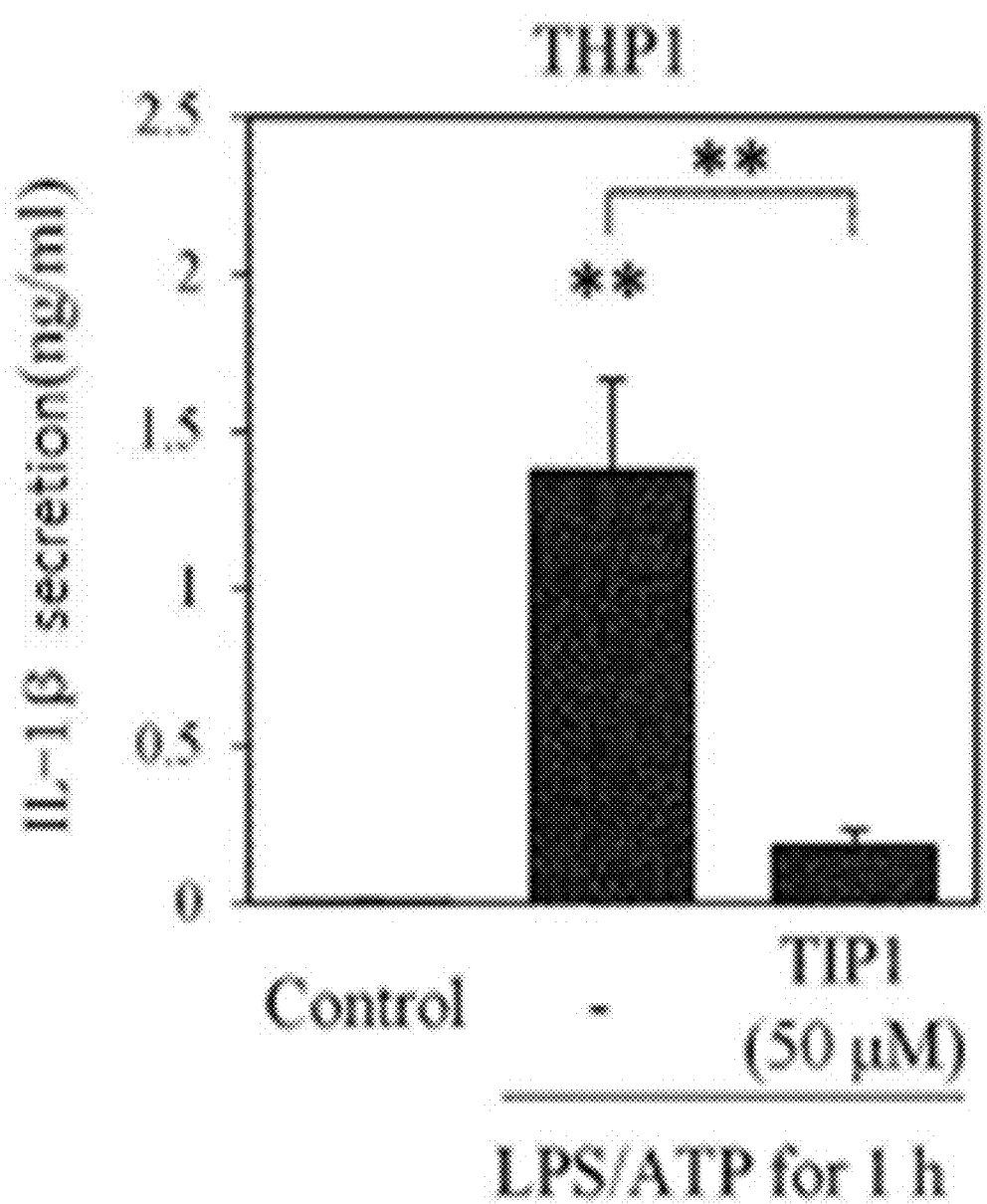
FIG. 11(a) illustrates results obtained by identifying, in THP1 cells, that IL-1β secretion was inhibited in a case where treatment with TIP1 was performed in a state of NLRP3-mediated inflammasome induced by treatment with LPS and ATP.
Figure 11B:
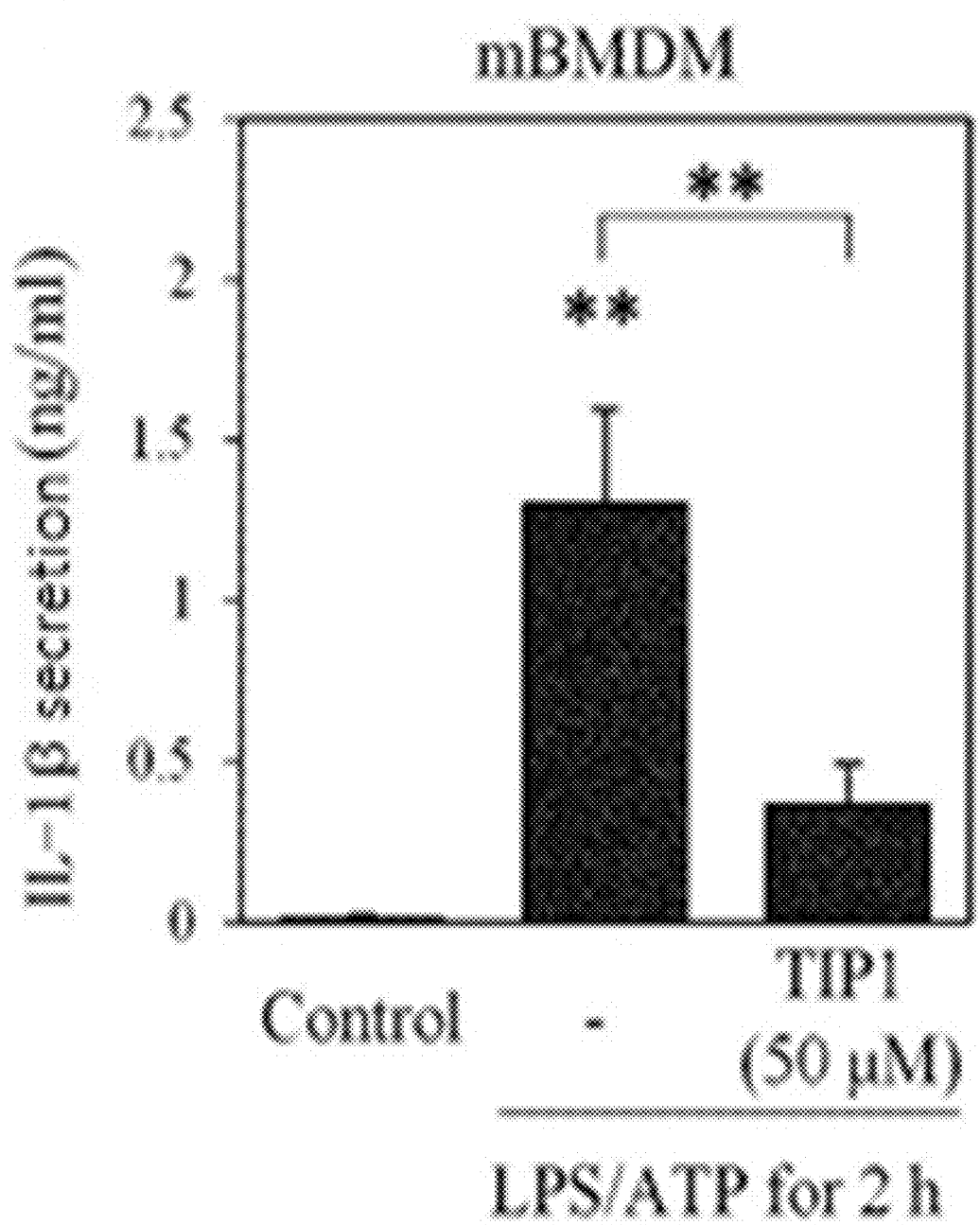
FIG. 11(b) illustrates results obtained by performing an experiment under the same conditions in mBMDM cells.

In addition, in order to identify an effect of TIP1 on cytokine secretion when NLRP3 inflammasome is induced, THP1 cells and mBMDM cells were subjected to treatment with LPS/ATP, or to combined treatment with TIP1 and LPS/ATP, and then IL-1β levels in the culture supernatants were measured using human and mouse IL-1β Ready-SET-Go! ELISA kits according to the method described in Example 2-5. The results are illustrated in FIGS. 11(a) and 11(b).

Figure 10A:
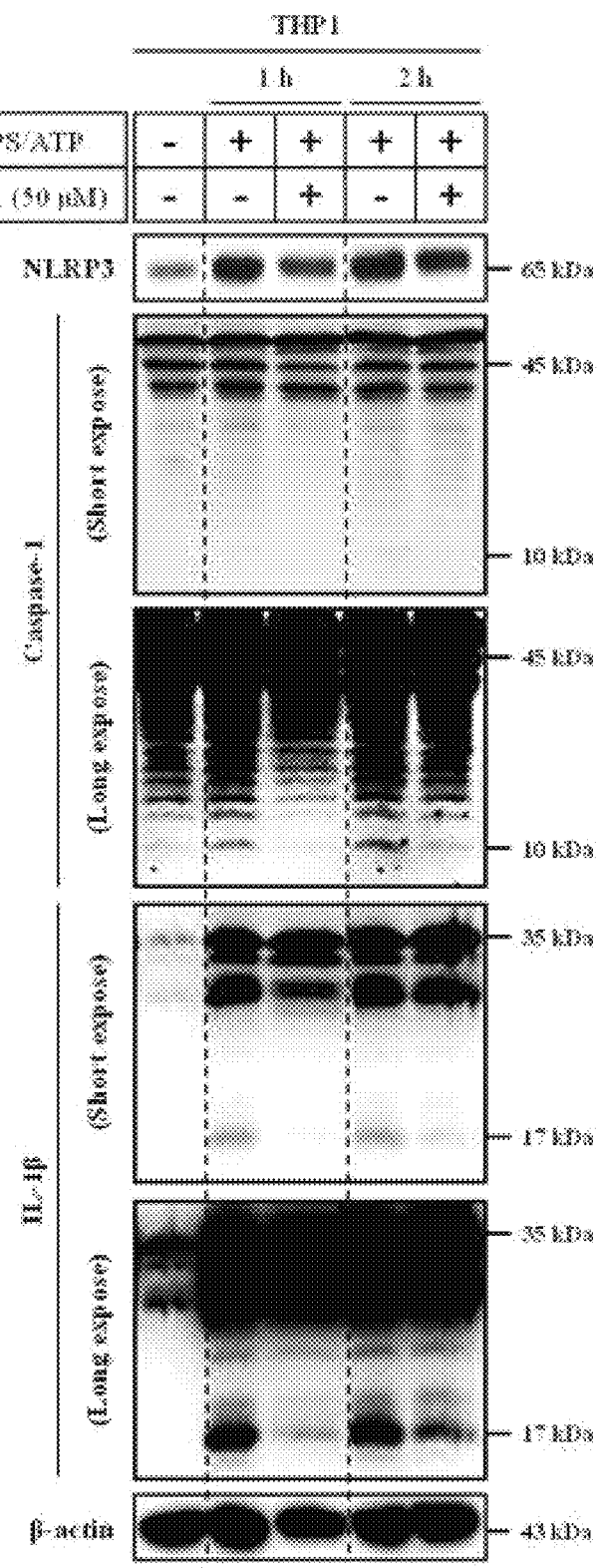
FIG. 10(a) illustrates results obtained by identifying, in THP1 cells, that molecules involved in formation of NACHT, LRR and PYD domains-containing protein 3 (NLRP3)-mediated inflammasome induced by treatment with LPS and ATP, were inhibited by TIP1.
Figure 10B:
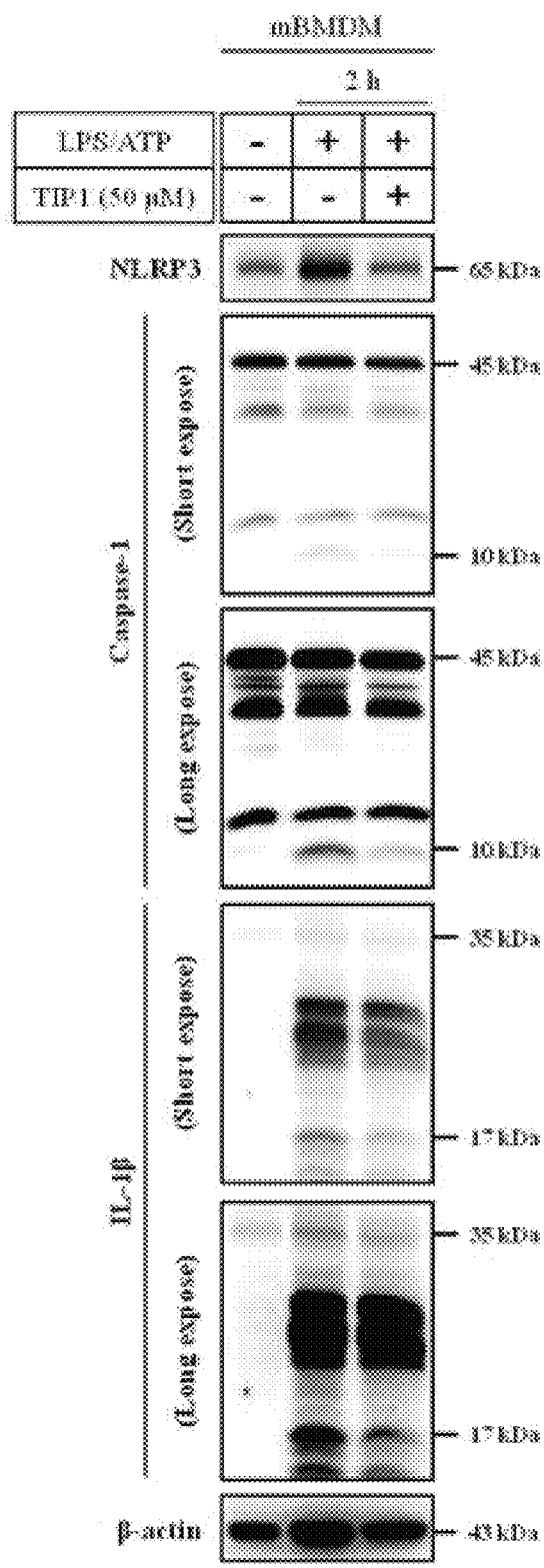
FIG. 10(b) illustrates results obtained by performing an experiment under the same conditions in mBMDM cells.

As illustrated in FIGS. 10(a) and 10(b), it was identified that LPS- and ATP-induced expression of NLRP3, caspase-1, IL-1β in the THP1 and mBMDM cells was inhibited by TIP1. Specifically, it was identified that TIP1 remarkably decreased intracellular expression levels of NLRP3, active caspase-1 (10 kDa), and mature IL-1β (17 kDa), and ultimately inhibited secretion of IL-1β. In addition, as illustrated in FIGS. 11(a) and 11(b), it was identified that in a case where combined treatment with TIP1 and LPS/ATP was performed, a secretion level of IL-1β was decreased. From these results, it was identified that TIP1 according to the present invention blocks the TLR4 signaling pathway, and thus inhibits activation of NLRP3 inflammasome.

NLRP3 inflammasome causes various inflammatory diseases, especially, degenerative neurological diseases, in a case of being abnormally activated. Thus, those that can effectively inhibit activity of NLRP3 inflammasome may be expected to be used as therapeutic agents for degenerative neurological diseases through inhibition of inflammatory responses. Therefore, from these results, the present inventors identified that TIP1 according to the present invention can exhibit a prophylactic or therapeutic effect on degenerative neurological diseases.

Experimental Example 7. Identification of TIP1 Sequence Specificity

In order to identify the minimum amino acid region of TIP1 which binds to the TIR domain of TLR4, using the amino acid sequence of the decoy peptide prepared in Example 1-1, S-H-C-R-V-L-L-I (SEQ ID NO: 1), the present inventors bound each of the sequences S-H-C-R (decoy peptide 1-2, SEQ ID NO: 2) and V-L-L-I (decoy peptide 1-3, SEQ ID NO: 7) to the N-terminus of the same CPP sequence as used in Example 1-1. All peptides used in the present experimental example are listed in Table 3.

TABLE 3

| Name | Sequence | SEQ ID NO |
|---|---|---|
| Decoy peptide 1 (TIP1 W/O CPP) | SHCRVLLI | 1 |

TABLE 3-continued

| Name | Sequence | SEQ ID NO |
|---|---|---|
| Decoy peptide 1-2 | SHCR | 2 |
| TIP1 | RQIKIWFQNRRMKWKK SHCRVLLI | 3 |
| TIP1-2 | RQIKIWFQNRRMKWKKSHCR | 4 |
| Decoy peptide 1-3 | VLLI | 7 |
| TIP1-3 | RQIKIWFQNRRMKWKKVLLI | 8 |

The HEK-Blue™-hTLR4 cells cultured in Examples 1-2 were treated with TIP1 (CPP-SHCRVLLI), TIP1-1 (CPP), TIP1-2 (CPP-SHCR), and TIP1-3 (CPP-VLLI) in Table 3, together with LPS, and then NF-κB activity was measured using the method in Experimental Example 1. In addition, the hPBMC cells cultured in Example 1-2 were treated with TIP1 (CPP-SHCRVLLI), TIP1-1 (CPP), TIP1-2 (CPP-SHCR), and TIP1-3 (CPP-VLLI), together with LPS, and then secretion levels of NO were measured using the method in Example 2-7. The results are illustrated in FIGS. 12(a) and 12(b).

Figure 12A:
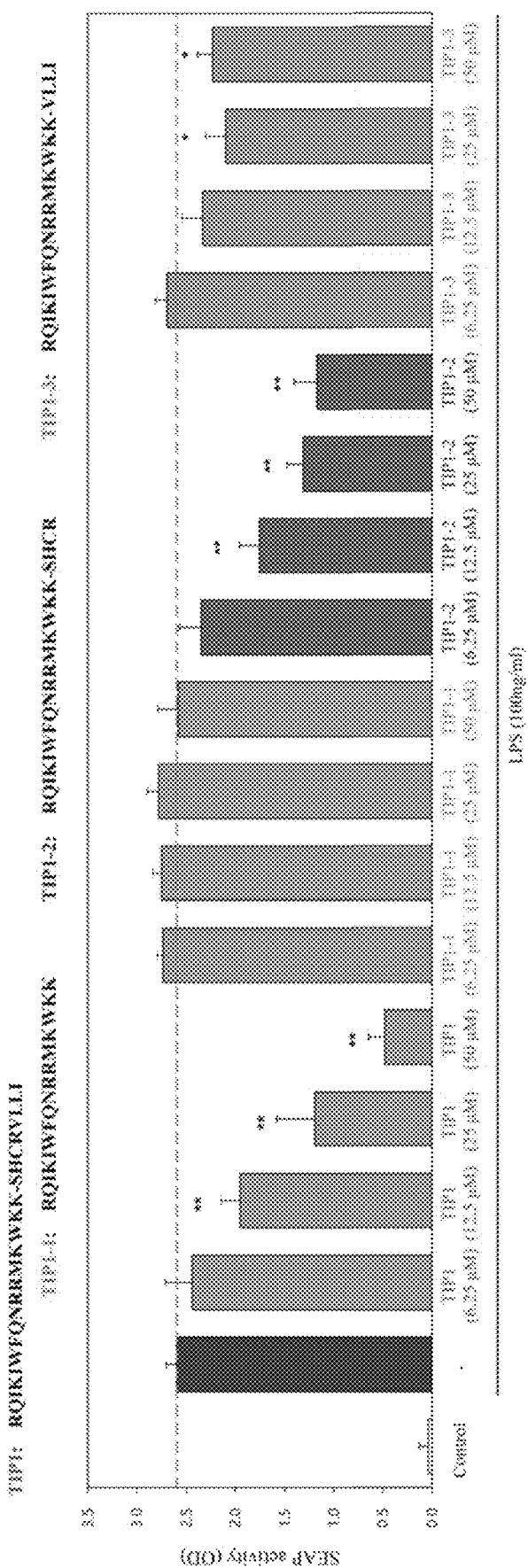
FIGS. 12(a) and 12(b) illustrate SEAP activity and NO secretion levels, respectively.
Figure 12B:
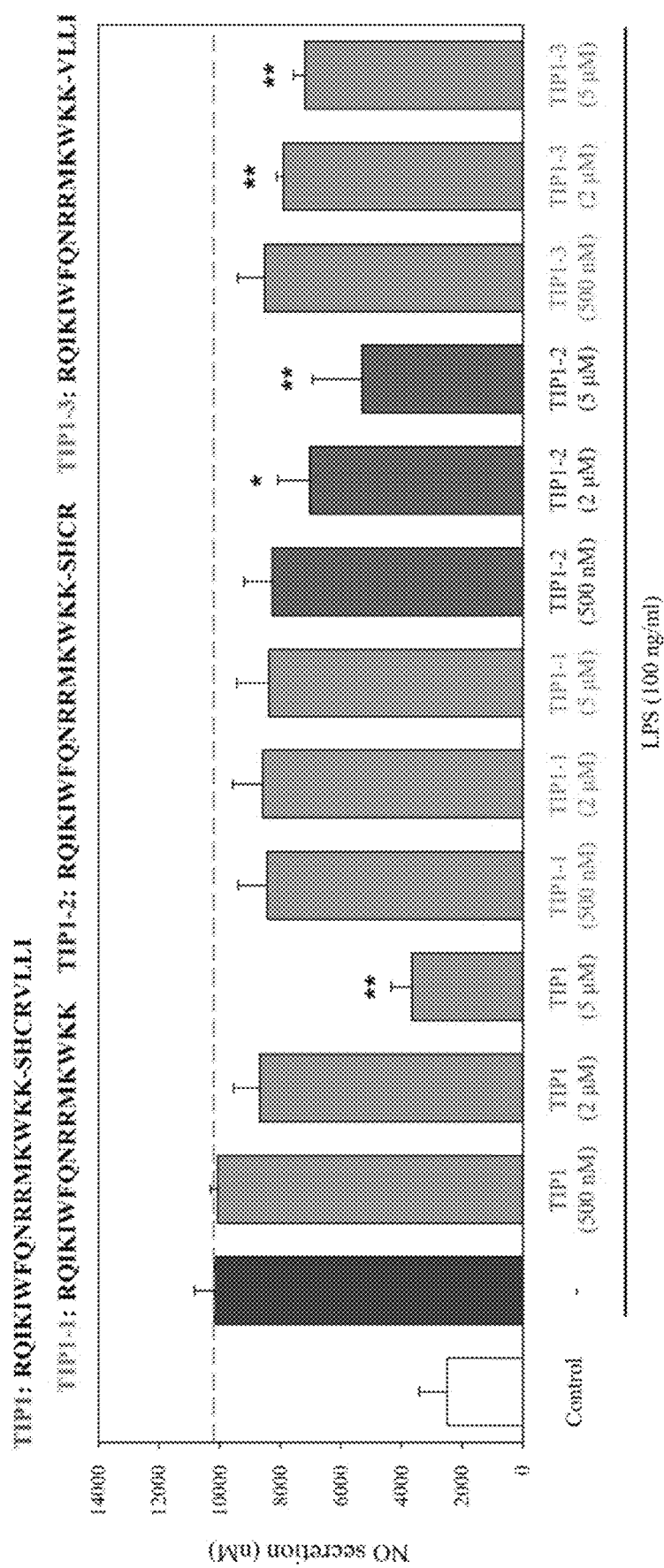

As illustrated in FIG. 12(a), it was identified that TIP1 had the highest inhibitory effect on NF-κB activity and TIP1-2 also decreased NF-κB activity, whereas no or insignificant changes were observed in a case of being treated with TIP1-1 or TIP1-3. In addition, as illustrated in FIG. 12(b), it was identified that TIP1 had the highest decreasing effect on NO secretion level and TIP1-2 also inhibited NO secretion, whereas no or insignificant changes were observed in a case of being treated with TIP1-1 or TIP1-3. From these results, it was identified that among the sequences of TIP1 according to the present invention, the S-H-C-R sequence is important for producing an inhibitory effect.

Experimental Example 8. Identification of Interaction Between TIP1 and TLR4, and MyD88

Protein-protein docking was performed to analyze the binding interface between the TIR domain of TLR4 and TIP1. As a result, TIP1 was expected to bind to the BB loop, the DD loop, and the C-terminal tail in the TIR domain of TLR4; and in order to identify this, surface plasmon resonance assay was performed according to the method described in Examples 2-8.

In addition, in order to identify binding of TIP1 to TLR4, TIP1-FITC was prepared by binding fluorescein isothiocyanate (FITC) to the N-terminus of TIP1. The THP1 cells in Example 1-2 were subjected to treatment with TIP1 (TIP1-FITC) or to combined treatment with LPS and TIP1, and then the number of fluorescently stained cells were counted using immunofluorescent staining and a confocal microscope according to the method described in Examples 2-4, thereby analyzing interactions between the proteins. The results are illustrated in FIG. 13.

Figure 13:
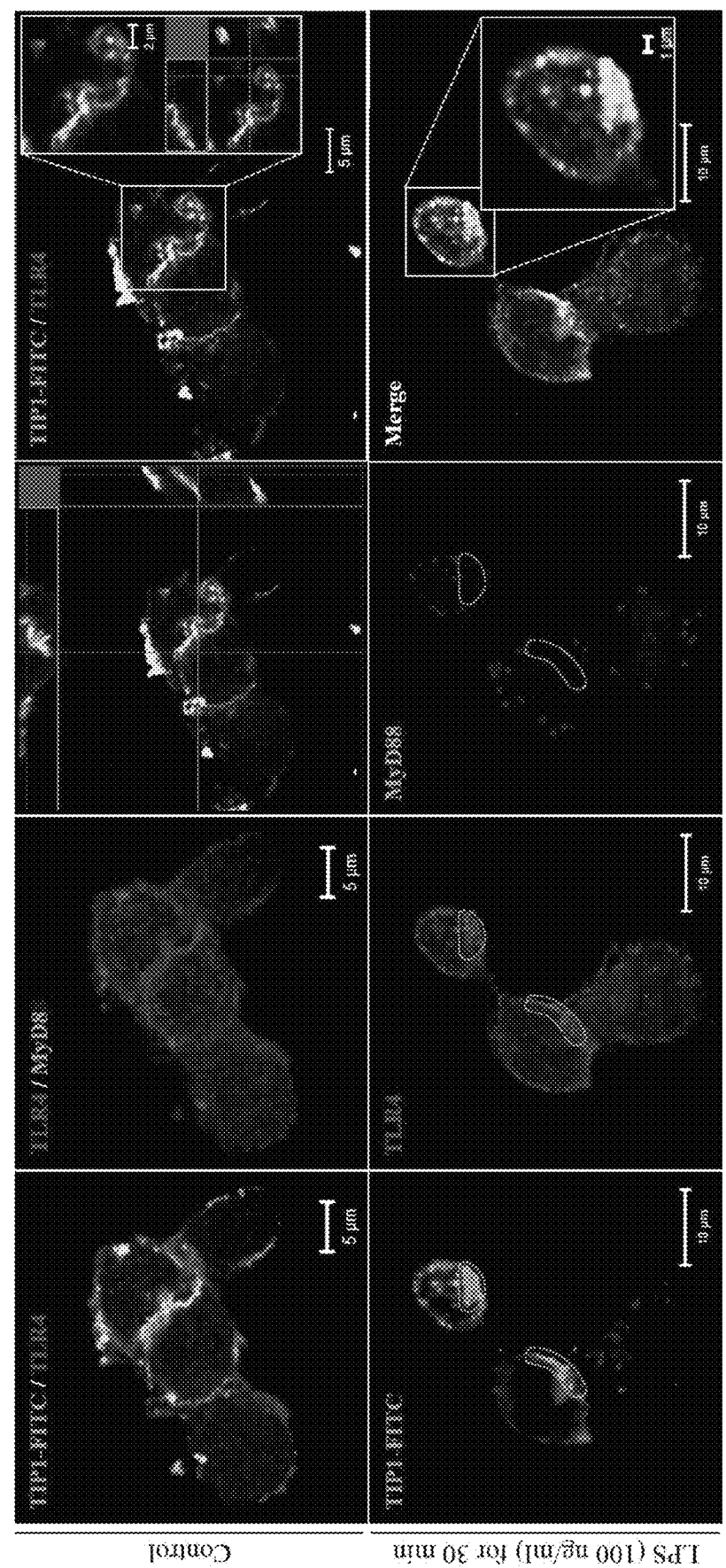
FIG. 13 illustrates results obtained by observing, with a confocal laser scanning microscope, interactions among TIP1 (green), TLR4 (red), and MyD88 (blue) in a case where THP1 cells, which were human monocytes, were treated with TIP1 (TIP1-FITC) to which fluorescein isothiocyanate (FITC) is bound, or treated with TIP1-FITC together with LPS, and identifying that TIP1 was bound to TRL4.

As illustrated in FIG. 13, it was identified that in a case where combined treatment with TIP1-FITC and LPS was performed, TIP1-FITC (green) and TLR4 (red) combined to form a complex, whereas MyD88 (blue) did not bind to the complex site. On the other hand, it was identified that in the absence of LPS, TLR4 was expressed in the plasma membrane, whereas MyD88 was spread within the cell; and in a case where the cells were subjected to treatment with LPS, both TLR4 and TIP1-FITC were introduced into the cells through an endocytosis process, and MyD88 agglomerated on the plasma membrane rather than being spread in the cells. In addition, it was identified that TIP1-FITC-TLR4 were strongly bound to each other, whereas MyD88 formed a weak bond to TIP1-FITC. From these results, it was identified that the inhibitory effect of TIP1 on the TLR4 signaling pathway was due to its binding to the C-terminal tail and the BB loop among the TIR domains of TLR4, while at the same time, the interaction between TIP1 and MyD88 was inhibited, thereby ultimately leading to hindrance of the TLR4 signaling process.

Experimental Example 9. Effect of TIP1 on Cytokine Secretion in Mice In Vivo

All animal experiments were conducted under approval of the Institutional Animal Care and Use Committee (KHNMC AP 2016-006). In order to identify an in vivo effect of TIP1, 8-week-old C56BL/6 (20 to 25 g, n=8) mice were purchased from OrientBio, Inc. (Seoul, Korea) and used for the experiments. The mice were intraperitoneally injected with TIP1 (10 nmol per g animal body weight), and 1 hour later, injected with LPS (5 µg per g animal body weight) for 2 hours. The control was injected with the same volume of PBS. Subsequently, the plasma was isolated through centrifugation from the mouse blood and stored at −80° C. until analysis of secretion levels. TNF-α, IL-12p40 (diluted at 1:100), and IL-6 (diluted at 1:100) levels in the plasma were measured using mouse TNF-α, IL-12p40, IL-6 ELISA MAX Deluxe ELISA kits (BioLegend, San Diego, Calif., USA). Absorbance was measured at 450 nm using a microplate reader spectrophotometer (Molecular Devices In.), and the results were analyzed using Softmax Pro 5.3 software (Molecular Devices Inc.). The results are illustrated in FIGS. 14(a)-14(c).

Figure 14A:
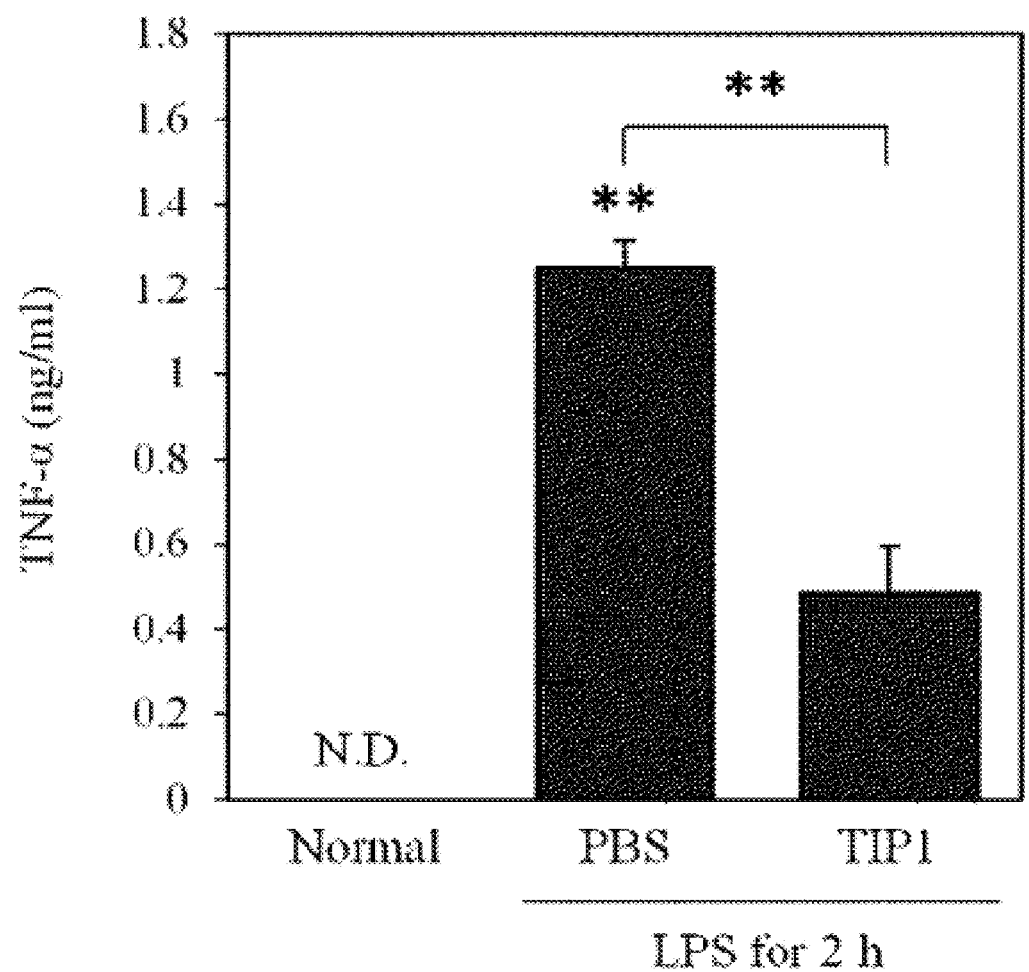
FIGS. 14(a)-14(c) illustrate results obtained by subjecting C57BL/6J mice to combined treatment with phosphate-buffered saline (PBS) and LPS, or with TIP1 and LPS, and then identifying cytokine secretion levels through the blood collected 1 hour or 2 hours after the treatment.
Figure 14B:
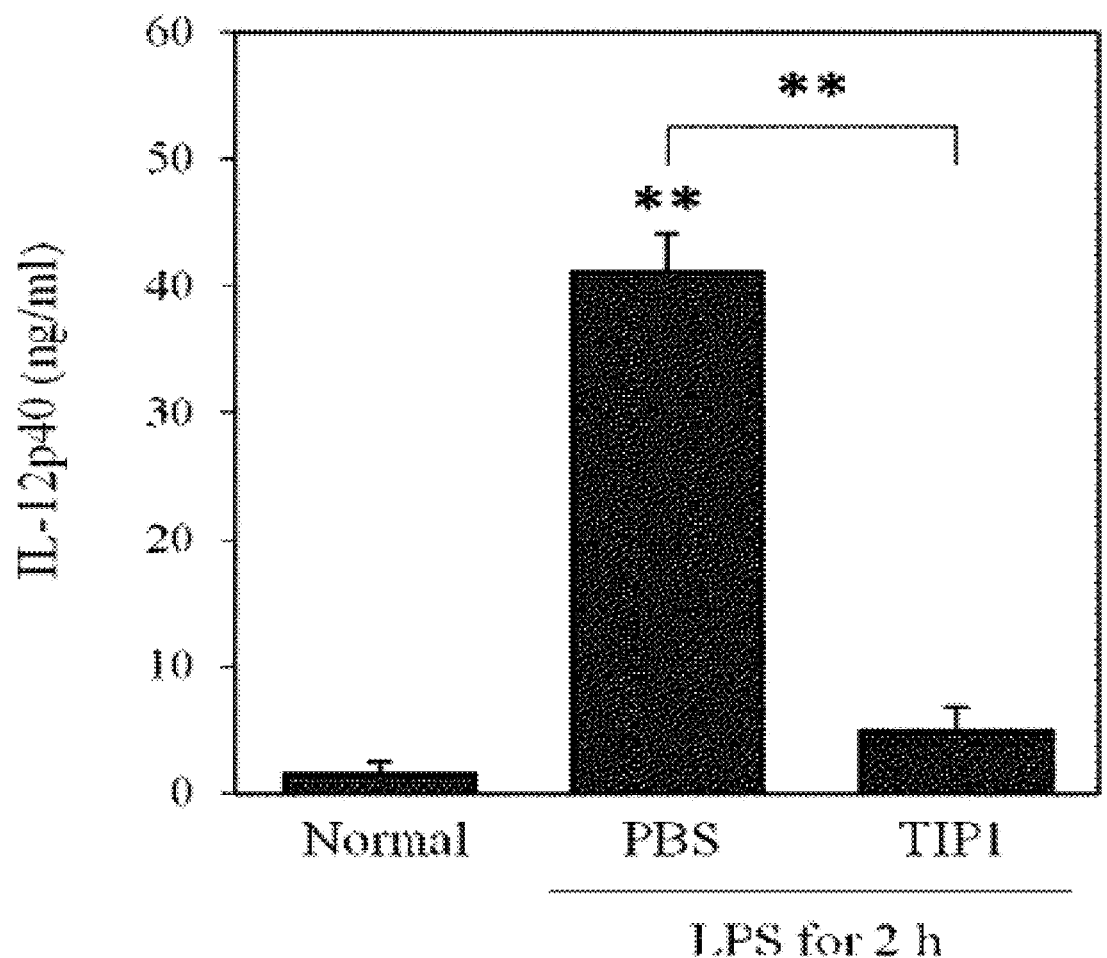
Figure 14C:
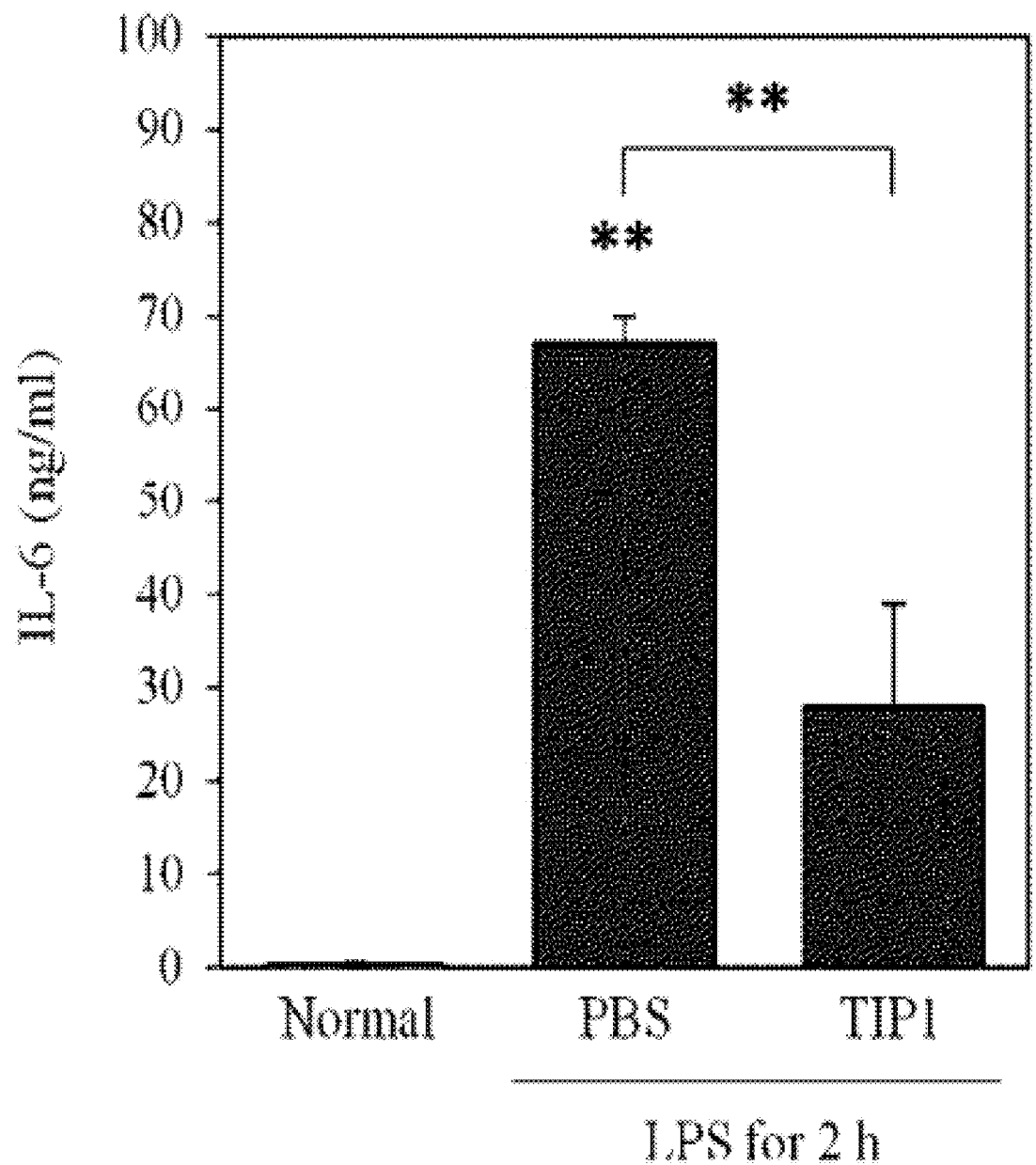

As illustrated in FIGS. 14(a) to 14(c), it was identified that in case where combined treatment with TIP1 and LPS was performed, secretion levels of TNF-α, IL-12p40, and IL-6 were remarkably decreased. From these results, it was identified that TIP1 according to the present invention inhibits the TLR4 signaling pathway, and thus inhibits secretion of cytokines in vivo as well as in vitro.

Experimental Example 10. Effect of TIP1 on Sepsis

In order to identify an effect of TIP1 on sepsis, C57BL/6J and BALB/c mice were subjected to combined treatment with PBS and LPS, or with TIP1 and LPS, and then the following experiments were conducted to identify changes in renal and hepatic damage, and survival rate.

10-1. Effect of TIP1 on Cytokine Secretion in Liver

C57BL/6J mice were subjected to combined treatment (2 hours) with PBS and LPS, or with TIP1 and LPS. Then, liver tissues were extracted and homogenized using the Kontes Pellet Pestle Cordless Motor (Thermo Fisher Scientific, Inc.) that contains an M-PER mammalian protein extraction reagent together with a Protease inhibitor cocktail (Thermo Fisher Scientific, Inc.). Then, proteins were extracted according to the manufacturer's protocol. Subsequently, protein expression of IL-6, TNF-α, and β-actin was visualized through Western blotting according to the method described in Example 2-3, and band intensities were graphically represented. The results are illustrated in FIGS. 15(a) and 15(b).

Figure 15A:
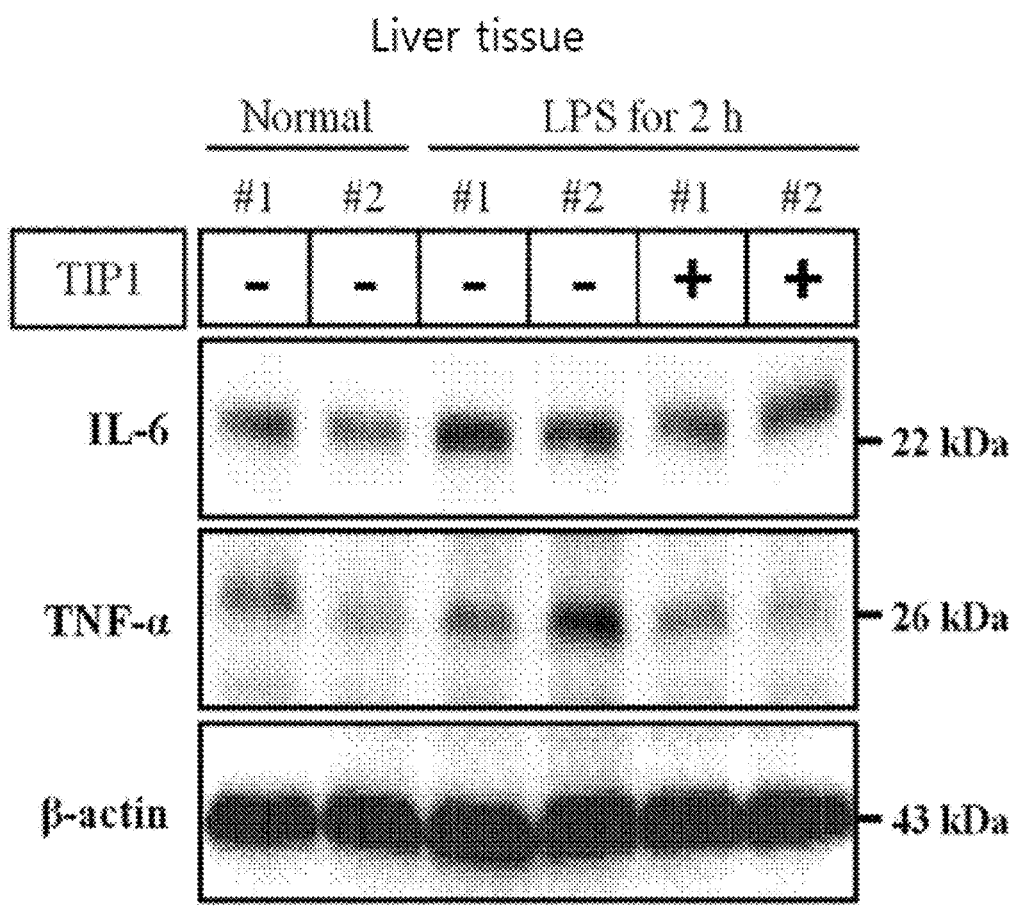
FIGS. 15(a) and 15(b) illustrate results obtained by identifying cytokine secretion levels in liver tissues of C57BL/6J mice in a case where the mice were subjected to combined treatment with PBS and LPS, or with TIP1 and LPS.
Figure 15B:
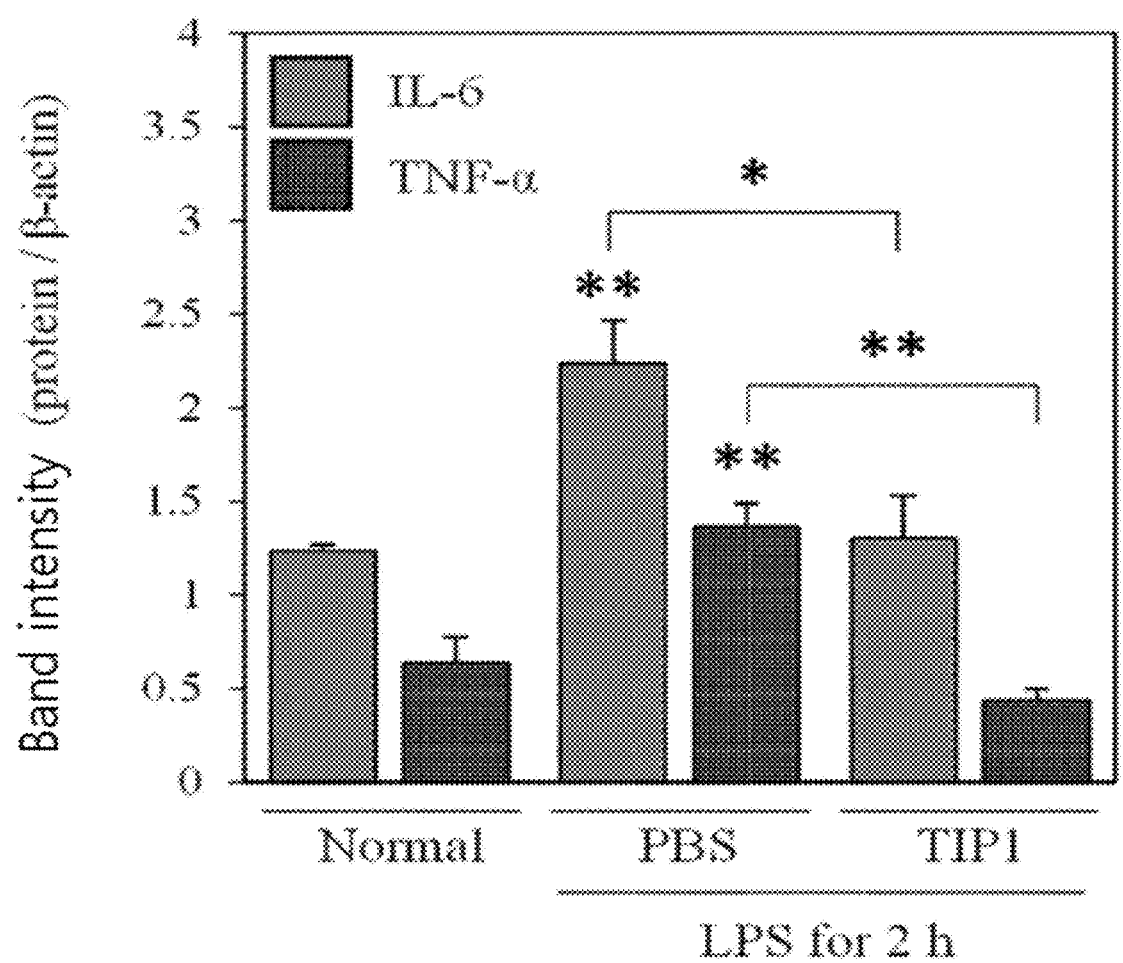
Figure 16A:
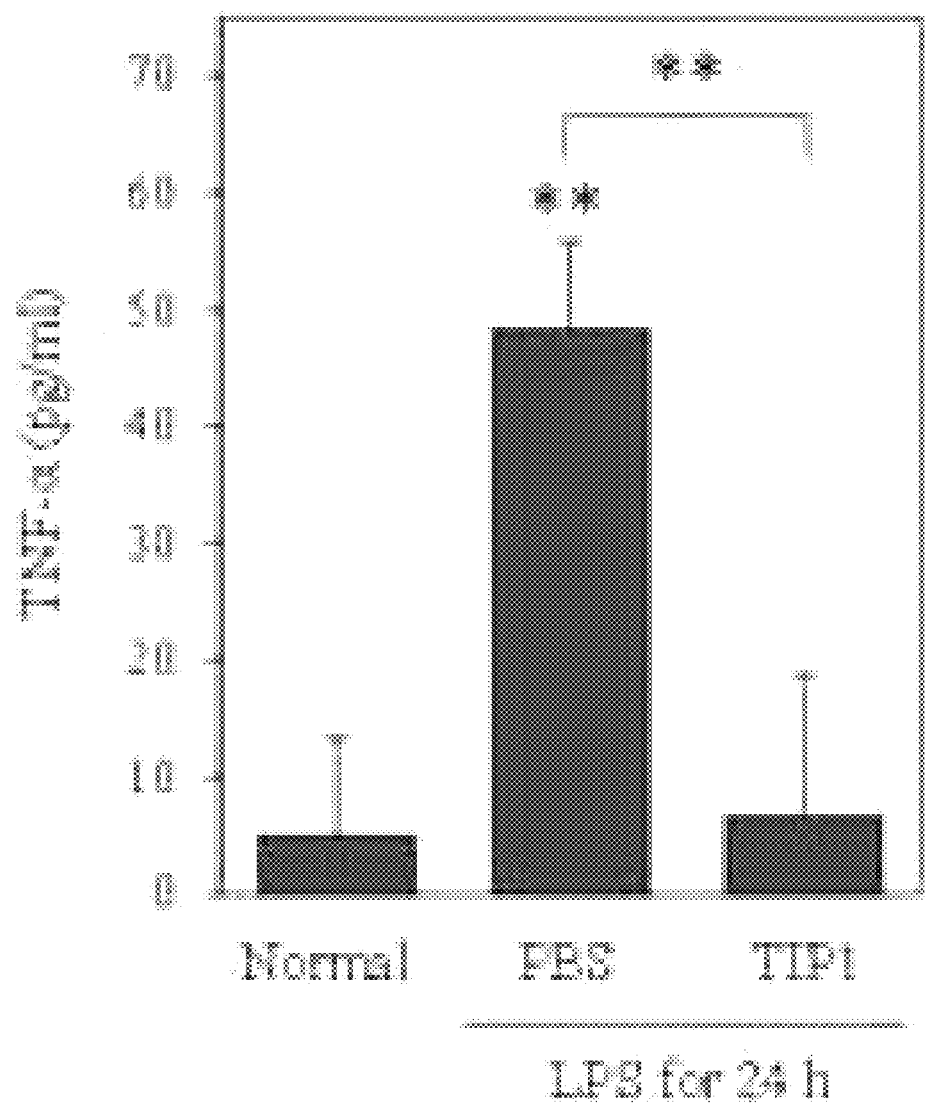
FIGS. 16(a) and 16(b) illustrate secretion levels of TNF-α and IL-6, respectively.
Figure 16B:
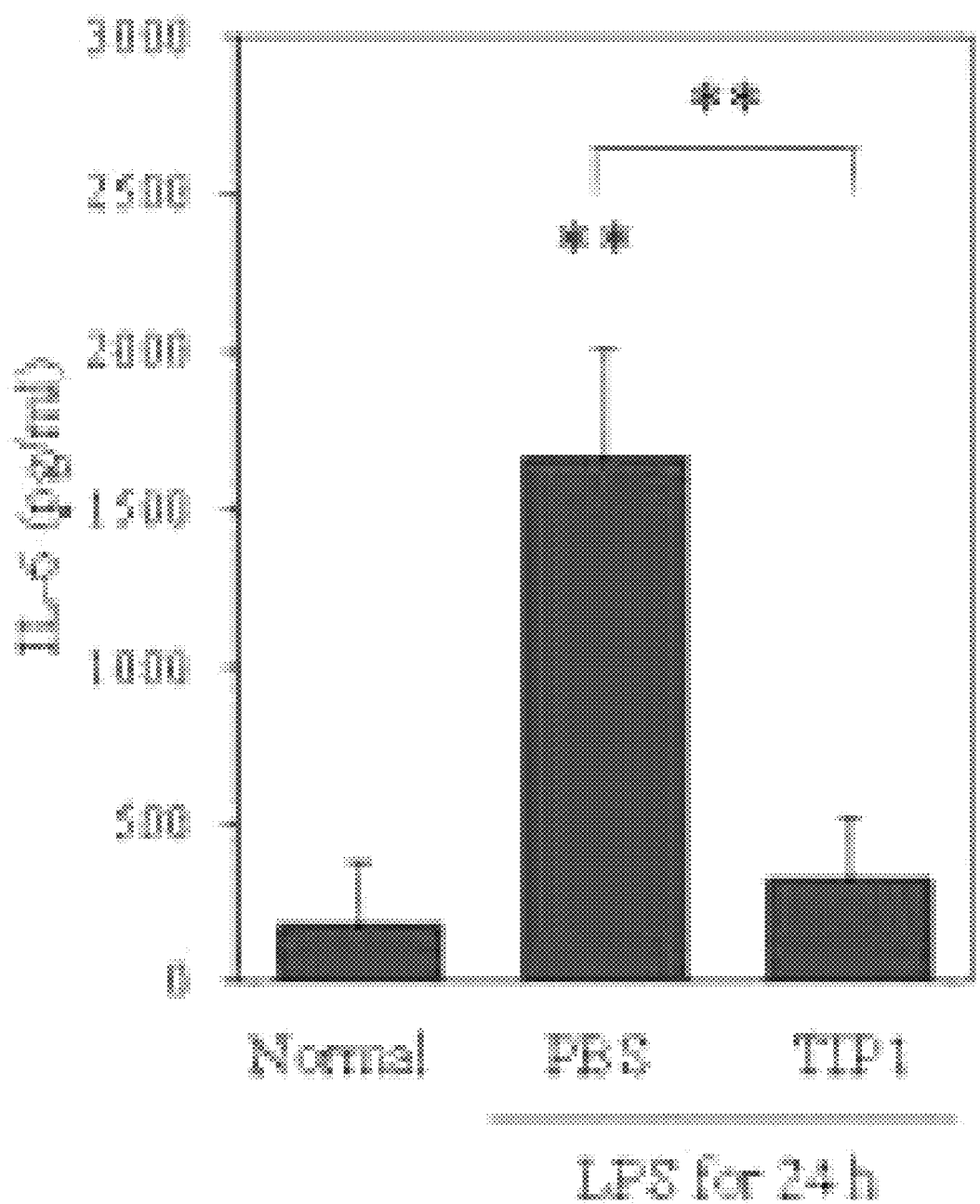
Figure 16C:
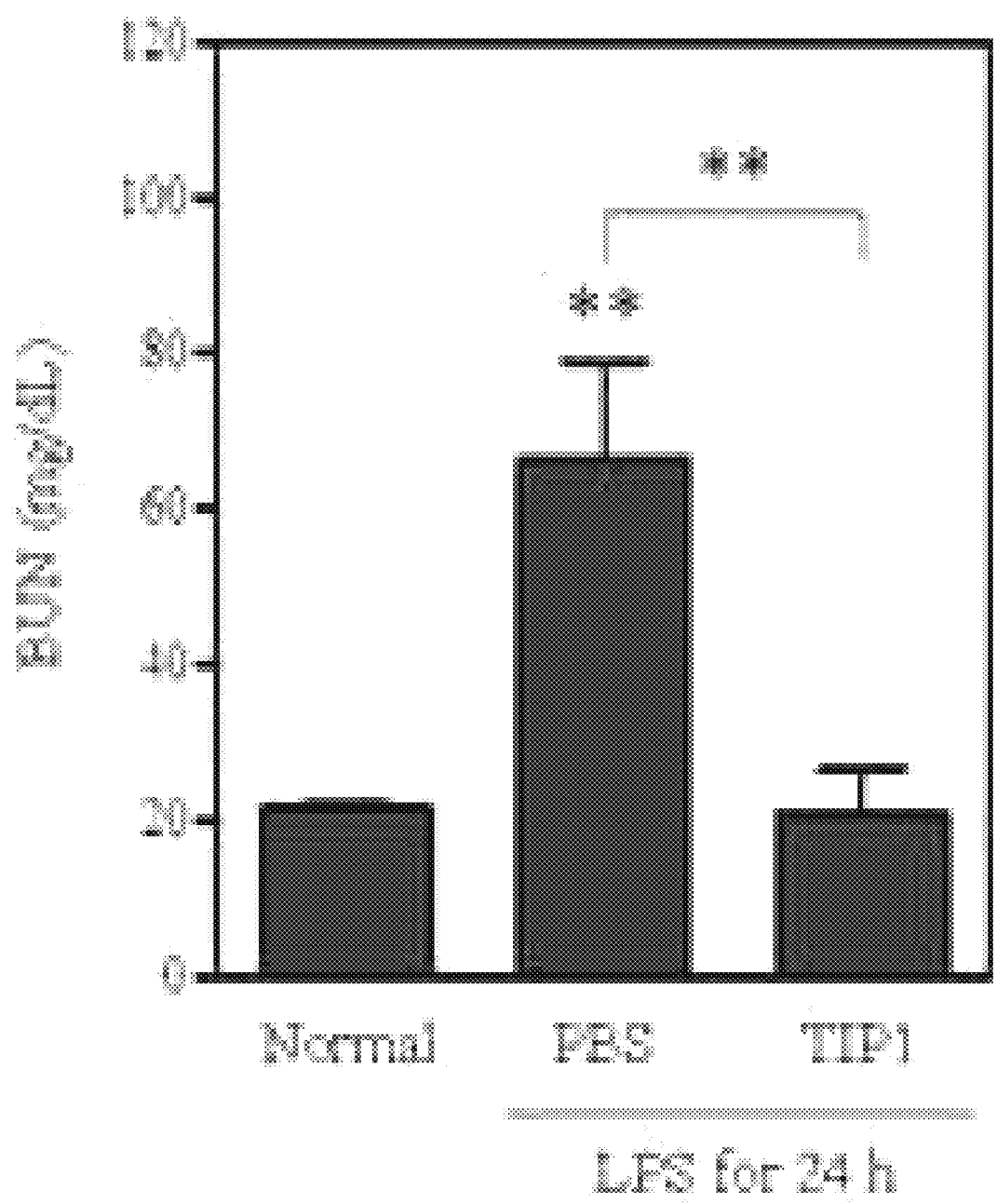
FIGS. 16(c) and 16(d) illustrate secretion levels of blood urea nitrogen (BUN) and creatinine (Cr), which are renal damage markers, respectively.
Figure 16D:
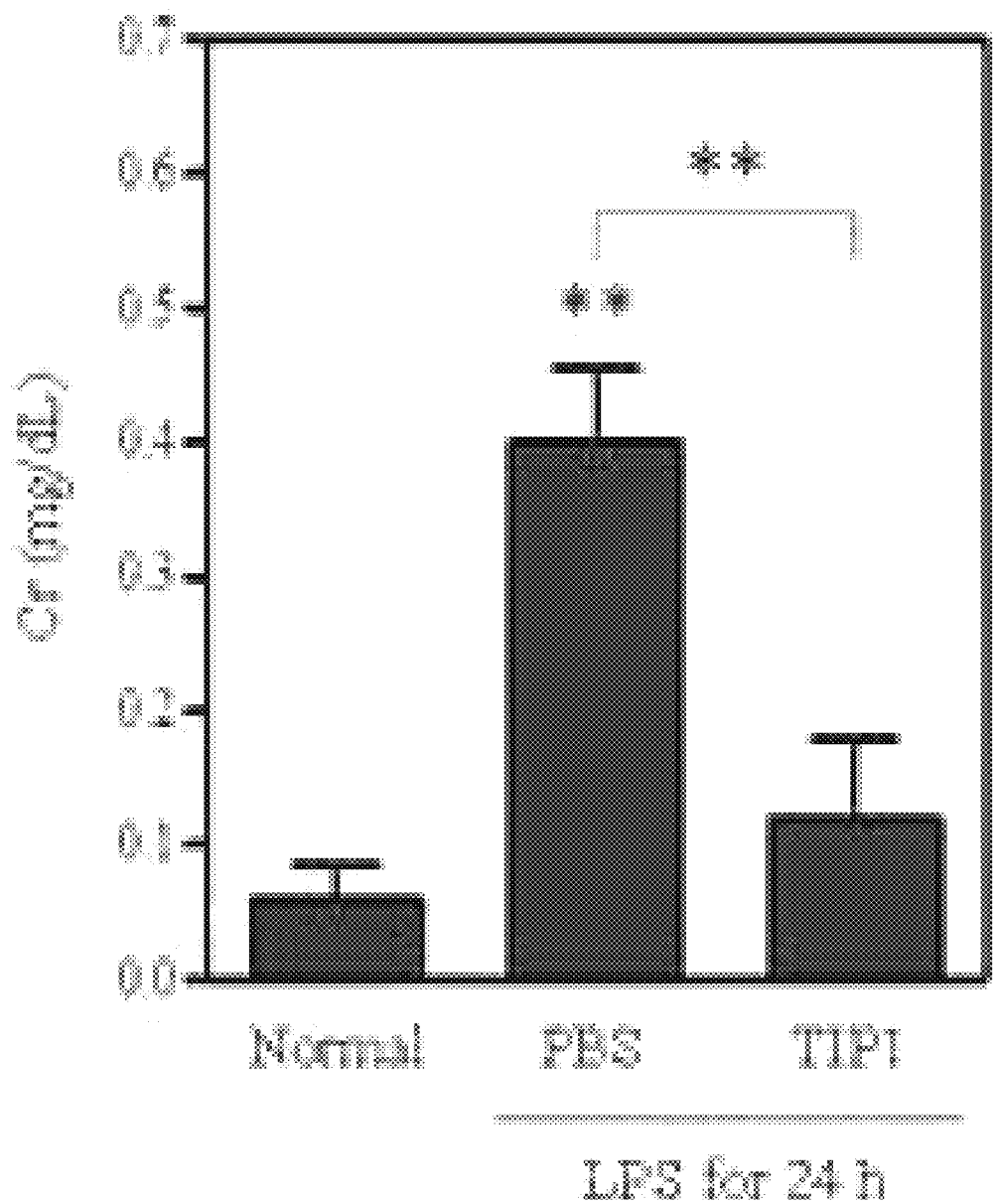
Figure 16E:
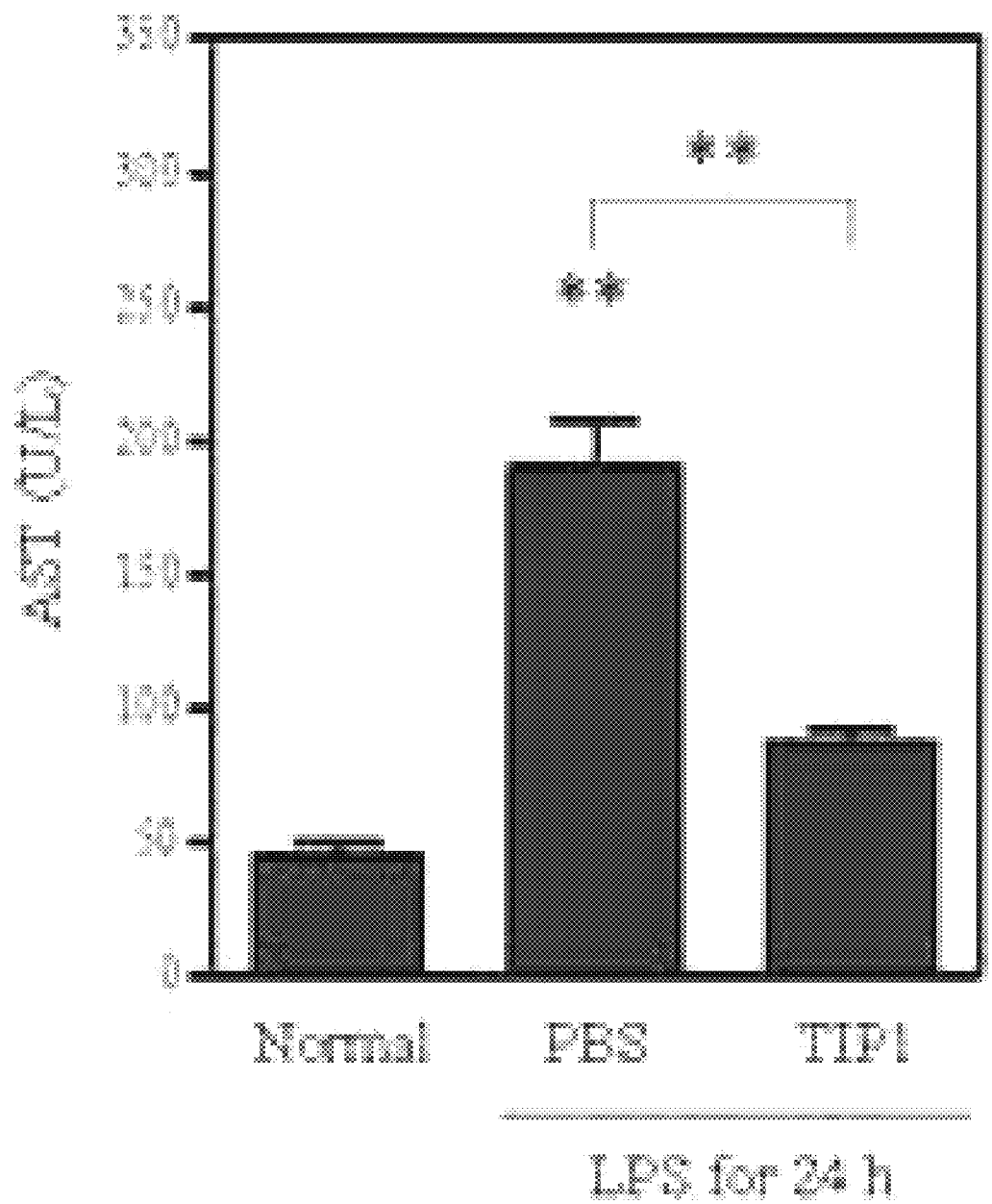
FIGS. 16(e) and 16(f) illustrate secretion levels of aspartate aminotransferase (AST) and alanine aminotransferase (ALT), which are hepatic damage markers, respectively.
Figure 16F:
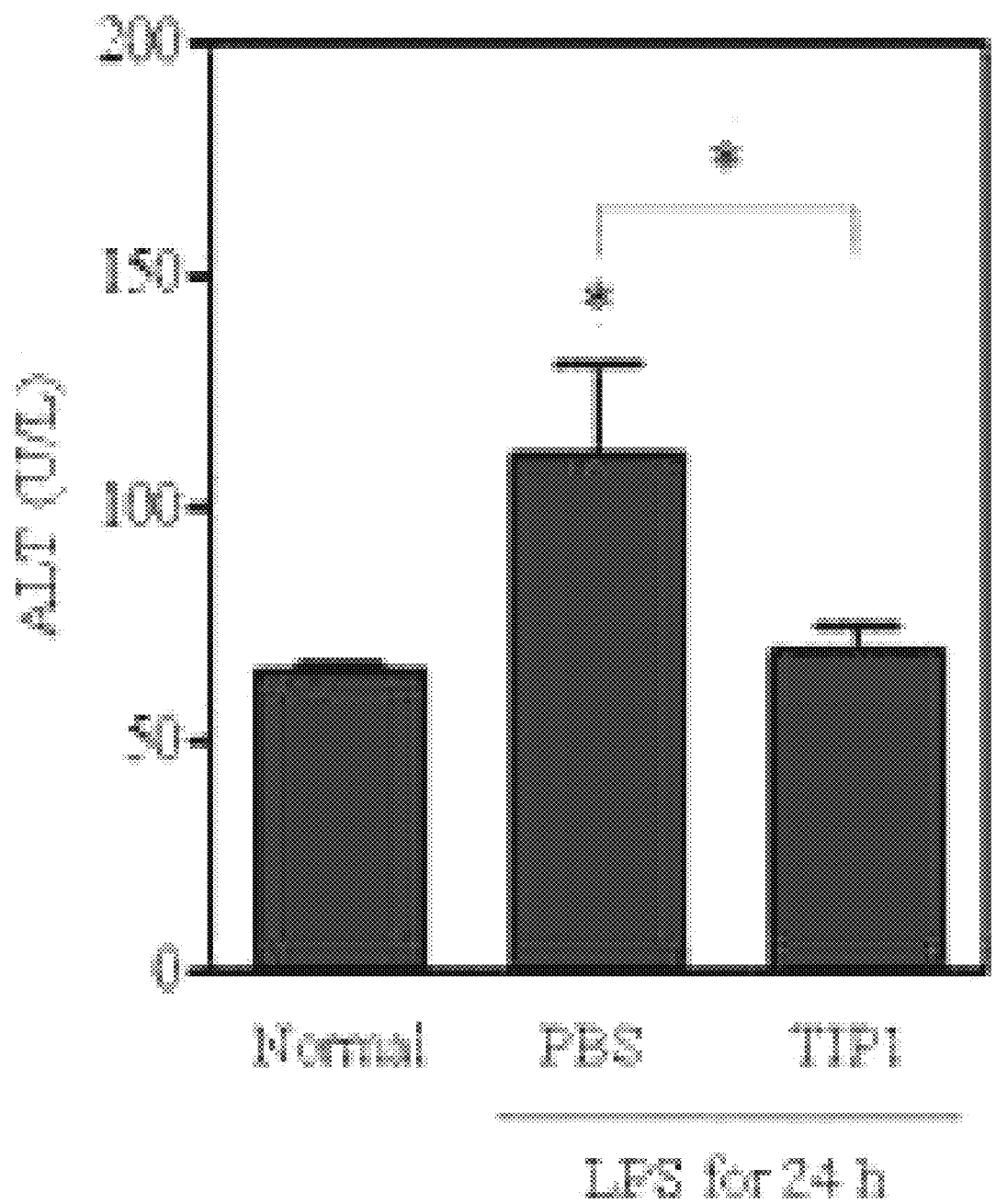

As illustrated in FIGS. 15(a) and 15(b), it was identified that in a case where combined treatment with LPS and TIP1 was performed, LPS-induced expression levels of TNF-α and IL-6 were remarkably decreased in mouse liver tissues.

10-2. Effect of TIP1 on Renal and Hepatic Damage

In order to more accurately identify an anti-inflammatory effect of TIP1 in a mouse sepsis model, an experiment was conducted in the same manner as above. Specifically, C57BL/6J mice were subjected to combined treatment (24 hours) with PBS and LPS, or with TIP1 and LPS, and then the plasma was isolated through centrifugation from the mouse blood. Using the isolated plasma, secretion levels of TNF-α and IL-6 were measured by the method in Experimental Example 9, and changes in secretion levels of the renal damage markers, blood urea nitrogen (BUN) and creatinine (Cr), and the hepatic damage markers, aspartate aminotransferase (AST) and alanine aminotransferase (ALT) were analyzed through VETTEST-8008-system (IDEXX). The results are illustrated in FIGS. 16(a)-16(f).

As illustrated in FIGS. 16(a) to 16(f), it was identified that in a case where combined treatment with TIP1 and LPS was performed, secretion levels of TNF-α and IL-6, and BUN, Cr, AST, and ALT were remarkably decreased. From these results, it was identified that TIP1 according to the present invention can inhibit the TLR4 signaling pathway, and thus alleviate renal and hepatic damage as well as cytokine secretion.

10-3. Effect of TIP1 on Renal Apoptosis

8-Week-old C56BL/6 (20 to 25 g, n=8) mice were subjected to combined treatment (24 hours) with TIP1 and LPS, or with PBS and LPS. Subsequently, renal tissues were isolated and weighed using an electronic balance (ER-180A, A&D Company, Tokyo, Japan); and then, cut into sagittal planes to make slices. The slices were left overnight in a 10% formalin solution, and then solidified by pouring of paraffin wax. The resultant was made into thin sections of 4 μm using a microtome and fixed. In order to identify an effect of TIP1 on apoptosis in the fixed renal tissue, the renal tissue was subjected to TUNEL (terminal deoxynucleotidyl transferase dUTP nick end labeling) (Merck Millipore, Billerica, Mass., USA) staining and the number of the fluorescently stained cells was counted using a confocal laser scanning microscope (LSM-700, Carl Zeiss MicroImaging GmbH, Jena, Germany). The images were analyzed using Zen 2009 software (Carl Zeiss MicroImaging GmbH.). The results are illustrated in FIG. 17.

Figure 17:
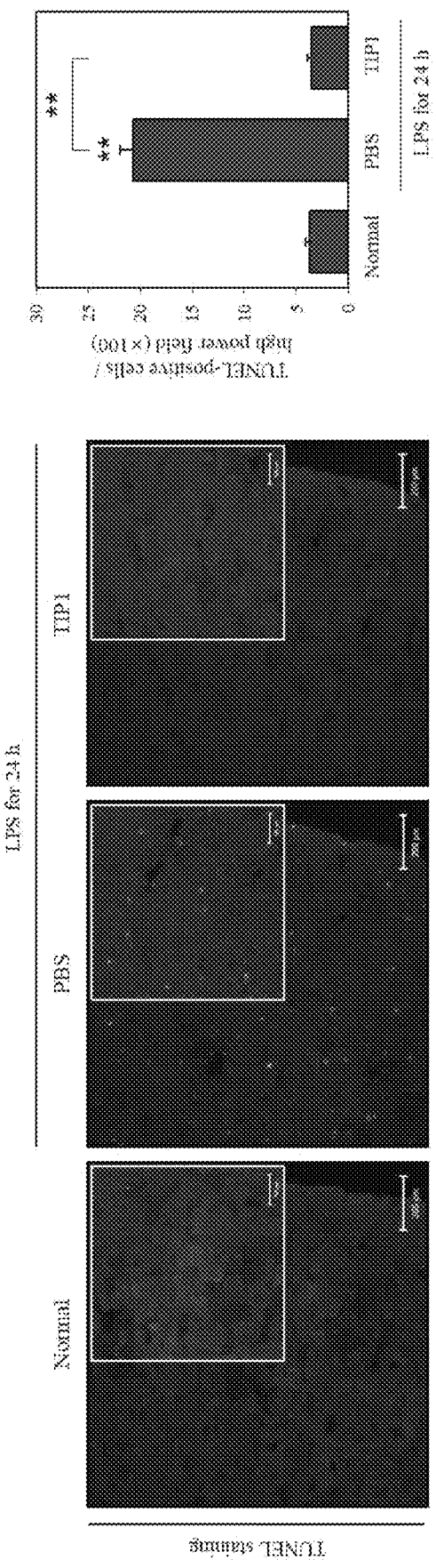
FIG. 17 illustrates results obtained by subjecting C57BL/6J mice to combined treatment with PBS and LPS, or with TIP1 and LPS, and then identifying, with terminal deoxynucleotidyl transferase dUTP nick end labeling (TUNEL) staining, an effect of TIP1 on renal apoptosis, using renal tissue collected 24hours after the treatment, indicating that TIP1 decreased apoptosis.

As illustrated in FIG. 17, it was identified that TUNEL-positive kidney cells were remarkably increased, that is, apoptosis (green spot) in renal tissue was increased, in a case where treatment with only LPS was performed, whereas increased apoptosis (green spot) in renal tissue due to LPS was decreased in a case where combined treatment with TIP1 and LPS was performed.

10-4. Effect of TIP1 on Survival Rate

In order to examine an effect of TIP1 on LPS-induced sepsis, 8-week-old BALB/c (20 to 25 g, n=8) male mice were subjected to treatment with LPS (5 or 10 μg per g animal body weight), and to combined treatment with TIP1 (10 nmol per g animal body weight) and LPS, and then survival rates thereof were measured for 5 days. The control was injected with the same volume of PBS. The results are illustrated in FIG. 18.

Figure 18:
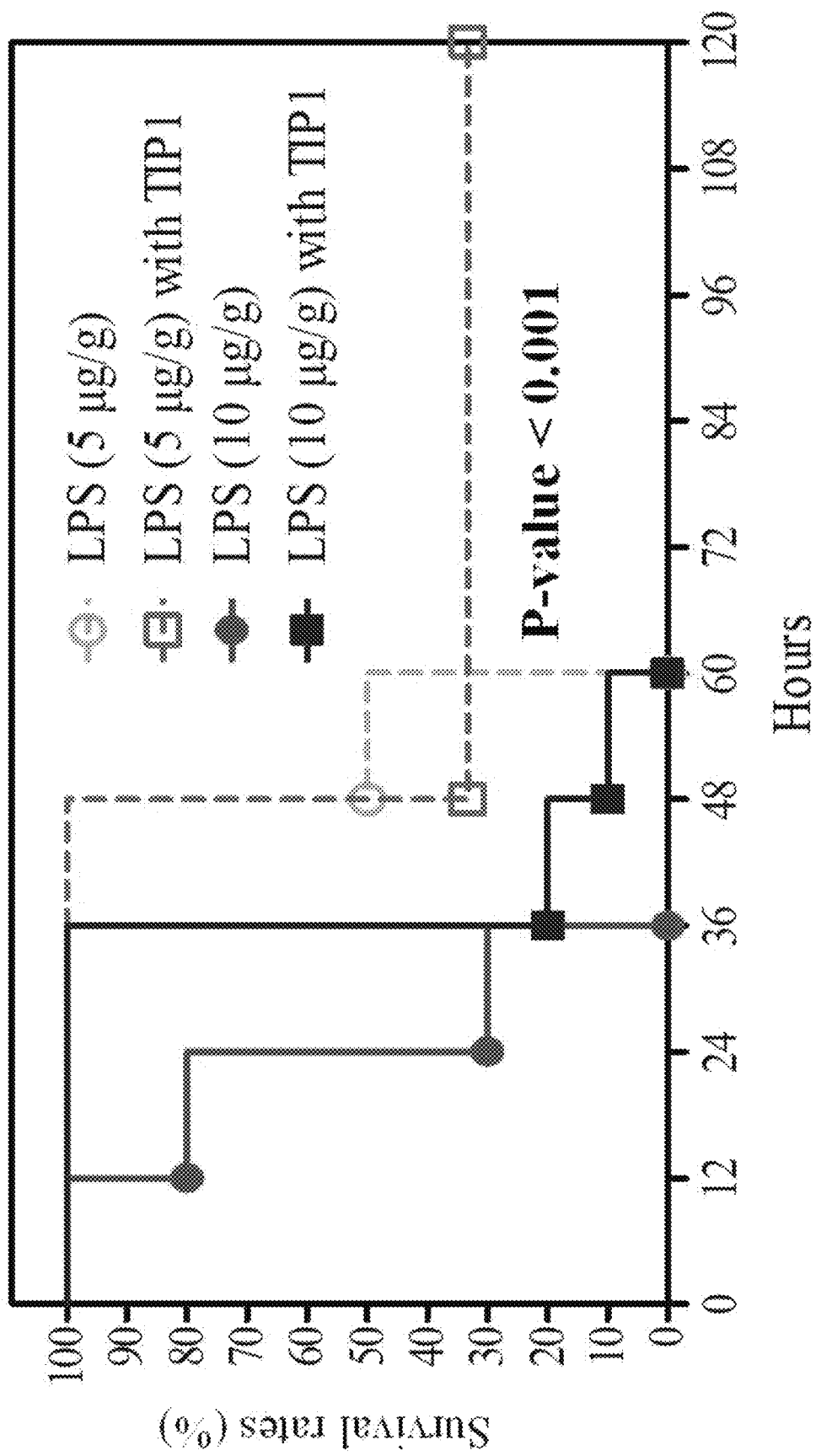
FIG. 18 illustrates that in a case where BALB/c mice were subjected to treatment with LPS, or to combined treatment with TIP1 and LPS, survival rates of LPS-induced sepsis model mice were increased.

As illustrated in FIG. 18, it was identified that an increased survival rate was observed in a case where combined treatment with TIP1 and LPS was performed, as compared with a case where treatment with only LPS is performed. Specifically, in a case of a mild sepsis model obtained by being treated with LPS at 5 μg/g, a survival rate was decreased by 100% in just 3 days; and a survival rate of 30% was maintained for 5 days in case of being treated with LPS together with TIP1. In addition, in a case of a severe sepsis model obtained by being treated with LPS at 10 μg/g, a survival rate was decreased by 70% in just one day, and all mice died two days later; and despite induction of severe sepsis, a survival rate was maintained at 100% for one day and was decreased by 90% after two days, in a case of being treated with LPS together with TIP1. From these results, it was identified that TIP1 according to the present invention inhibits the TLR4 signaling pathway to mitigate the early stage of inflammation so that cytokine secretion, and renal and hepatic damage are decreased, thereby eventually alleviating sepsis.

Experimental Example 11. Effect of TIP1 on Rheumatoid Arthritis

In order to identify an effect of TIP1 on rheumatoid arthritis, arthritis was induced by applying a collagen-induced arthritis (CIA) model to 6- to 7-week-old DBA/1J (20 to 23 g) male mice. Specifically, chicken collagen type II (Sigma-Aldrich Co. LLC) and complete Freund's adjuvant (Sigma-Aldrich Co. LLC.) were mixed at 1:1 and emulsified. Then, 100 μg of the emulsified collagen solution was injected intradermally into the mouse tail to induce primary immunization, which was designated day 0. After 14 days of the primary immunization, the emulsified collagen solution was injected again intradermally into the mouse tail to induce secondary immunization (boosting).

Subsequently, the following two TIP1 treatment plans were designed: ① Plan in which after the secondary immunization (day 15), TIP1 (2.5, 5, and 10 nmol/g) or 5 mg/kg of prednisolone, which is a well known, conventional therapeutic agent for arthritis and is used as a positive control, is injected daily for 30 days; and ② plan in which after complete induction of arthritis (day 35), 10 nmol/g of TIP1 is injected for 10 days. These plans included a total of seven experimental groups (n=8) and named as follows: (1) Non-treated, normal group (normal); (2) control (vehicle-treated) (CIA, n=8); (3) 2.5 nmol/g TIP1-treated group (CIA-TIP1 (2.5 nmol/g)); (4) 5 nmol/g TIP1-treated group (CIA-TIP1 (5 nmol/g)); (5) 10 nmol/g TIP1-treated group (CIA-TIP1 (10 nmol/g)); (6) 5 μg/g prednisolone (conventional therapeutic agent for arthritis)-treated group (CIA-prednisolone (5 μg/g)); (7) 10 nmol/g TIP1-treated group in post-arthritis phase (PAP) (PAP CIA-TIP1 (10 nmol/g)). TIP1 and prednisolone were dissolved in saline and injected intraperitoneally. Then, changes in behavioral development and disorders such as apparent symptoms and body weight, mouse squeaking, foot volume, and arthritis index were analyzed. The results are illustrated in FIGS. 19(a) and 19(b) and 20(a)-20(d).

Figure 19A:
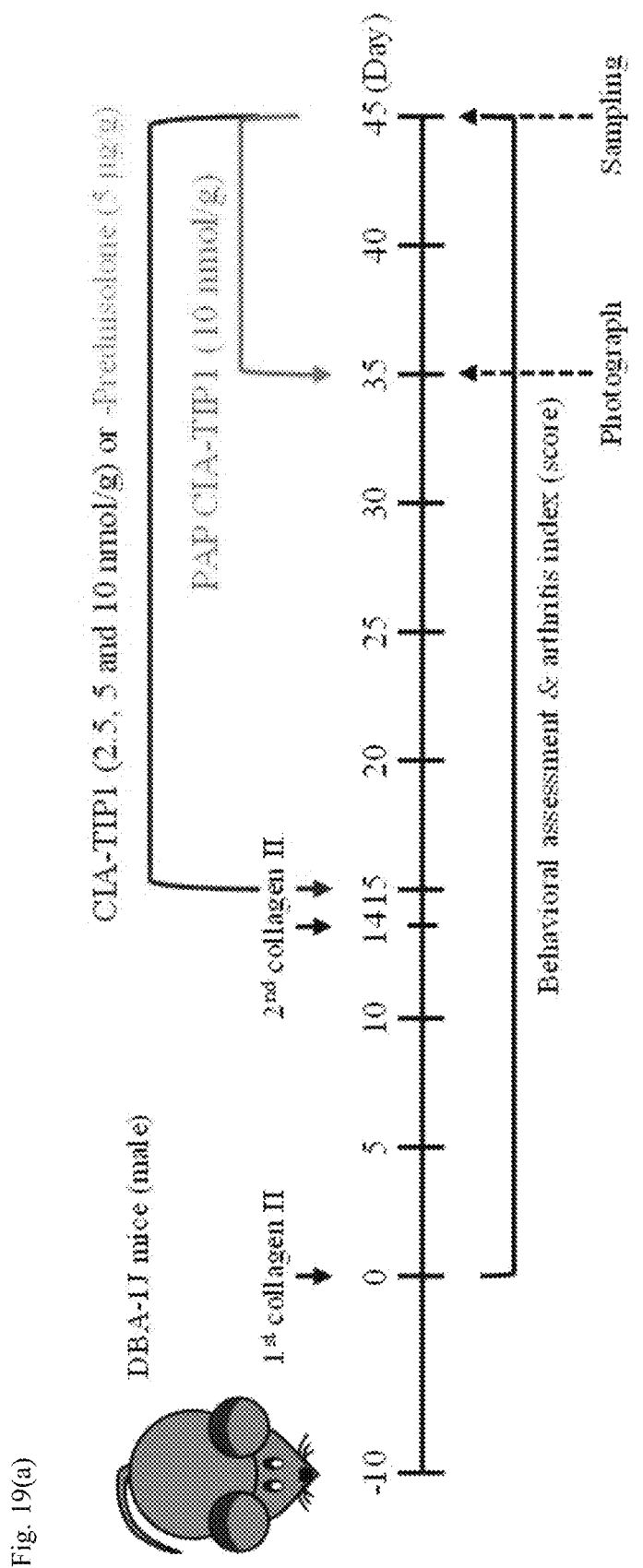
FIG. 19(a) illustrates an experimental design for identifying a therapeutic effect of TIP1 on rheumatoid arthritis using a collagen-induced arthritis (CIA) (collagen-induced rheumatoid arthritis) model of DAB-1J mice.
Figure 19B:
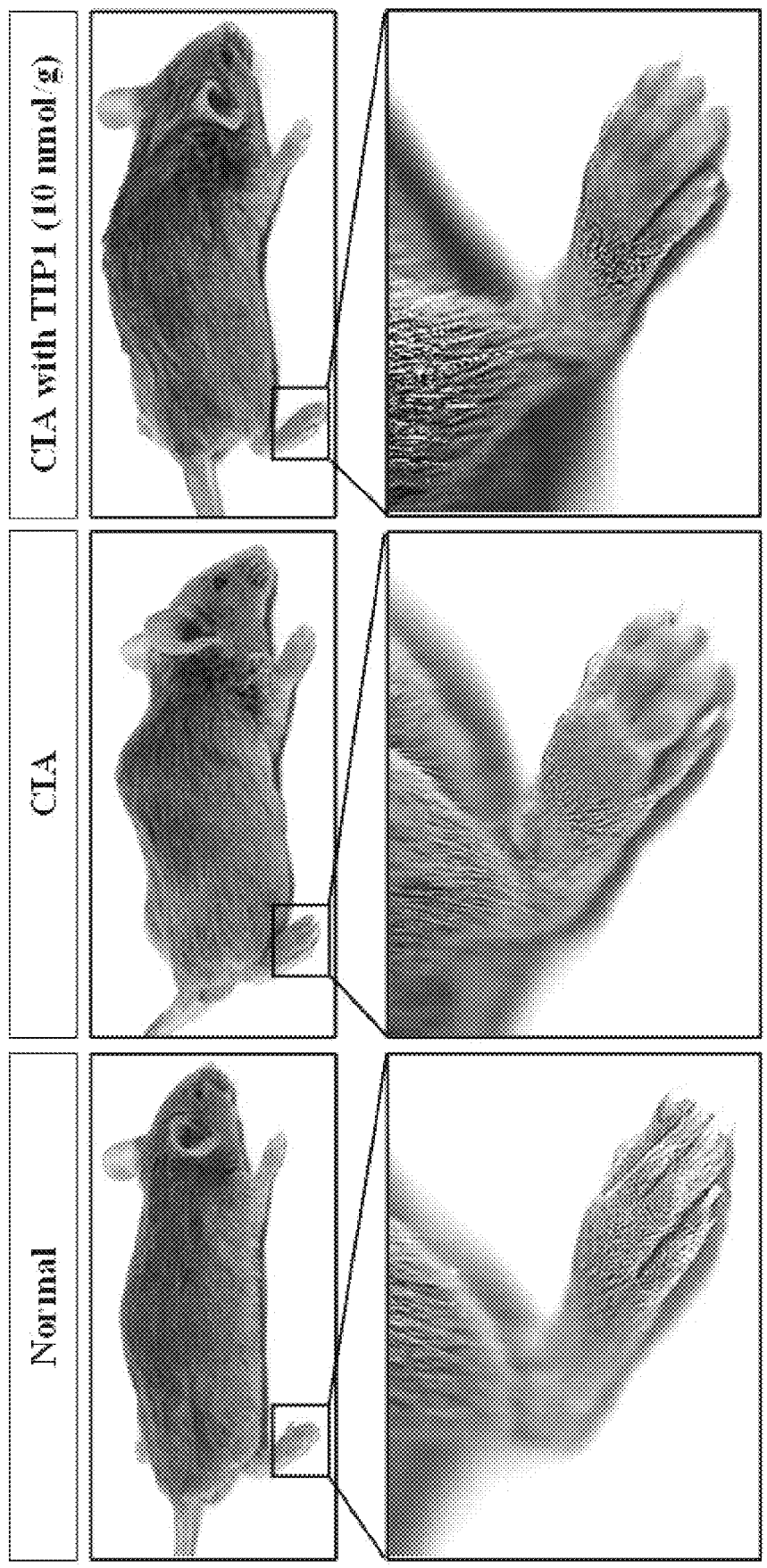
FIG. 19(b) illustrates visual observation of a therapeutic effect in a case where treatment with TIP1 was performed, indicating that rheumatoid arthritis was treated.
Figure 20A:
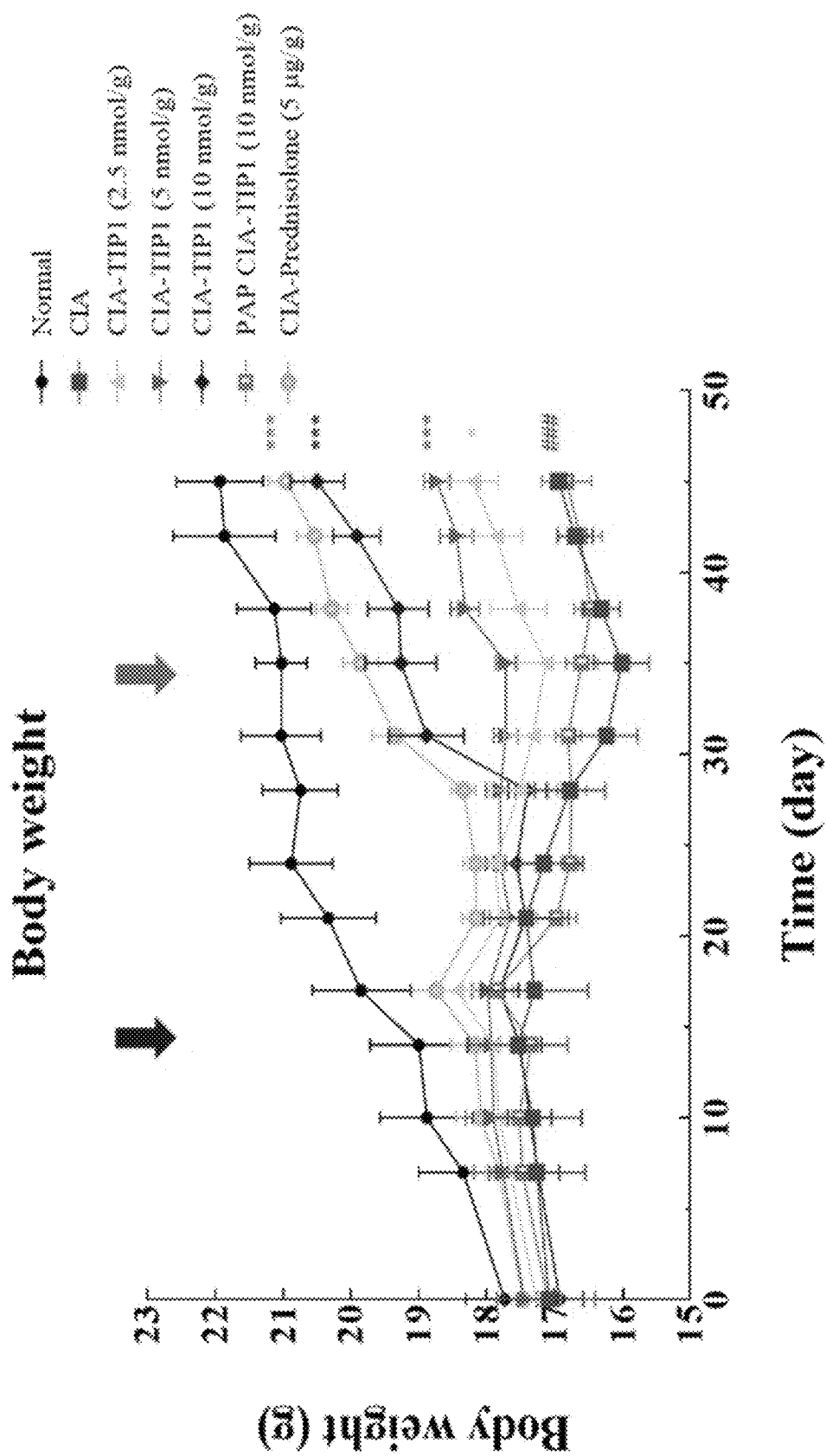
FIGS. 20(a)-20(d) illustrate results obtained by identifying therapeutic effects in a case where a CIA rheumatoid arthritis model of DAB-1J mice was treated with TIP1.
Figure 20B:
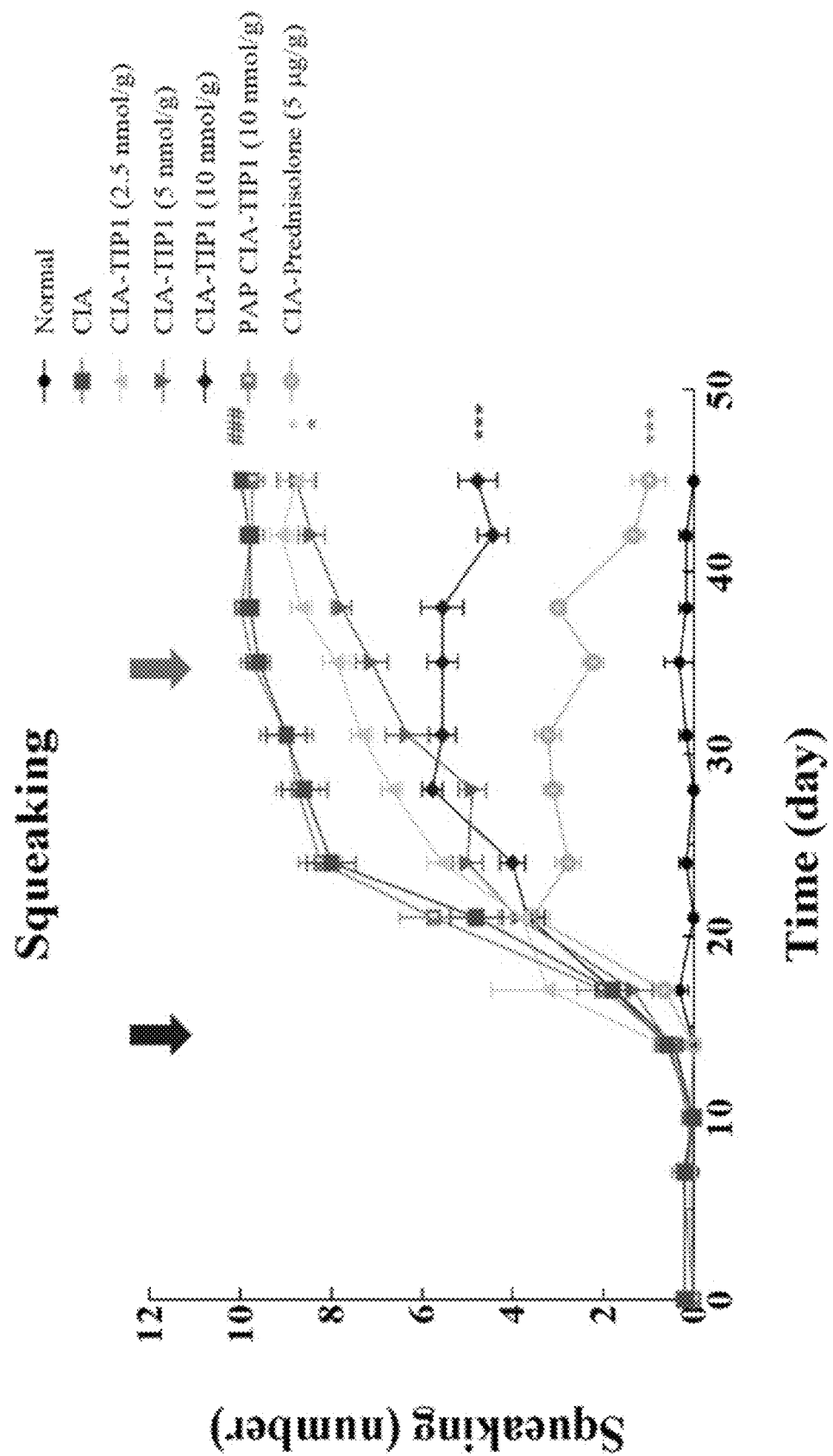
Figure 20C:
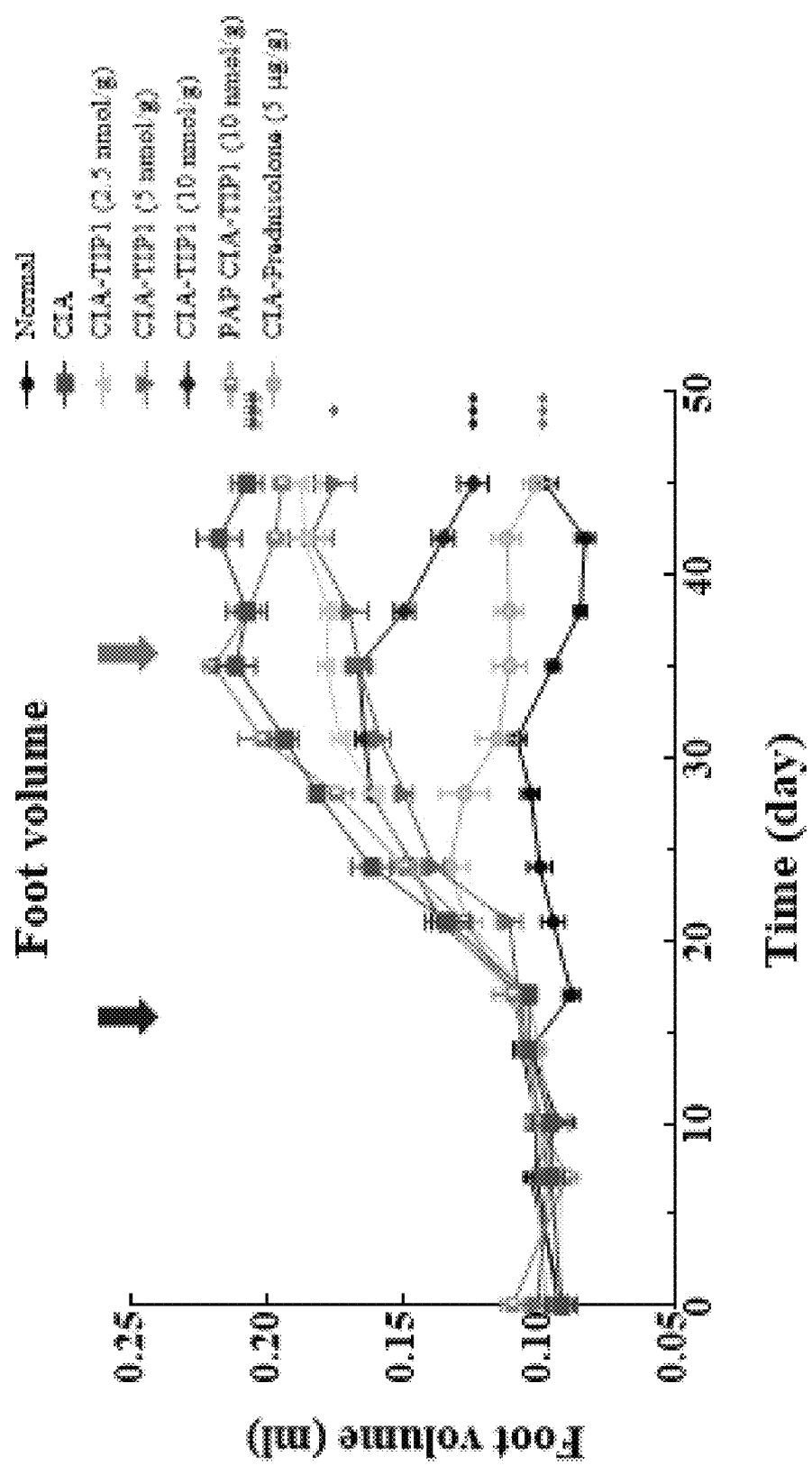
Figure 20D:
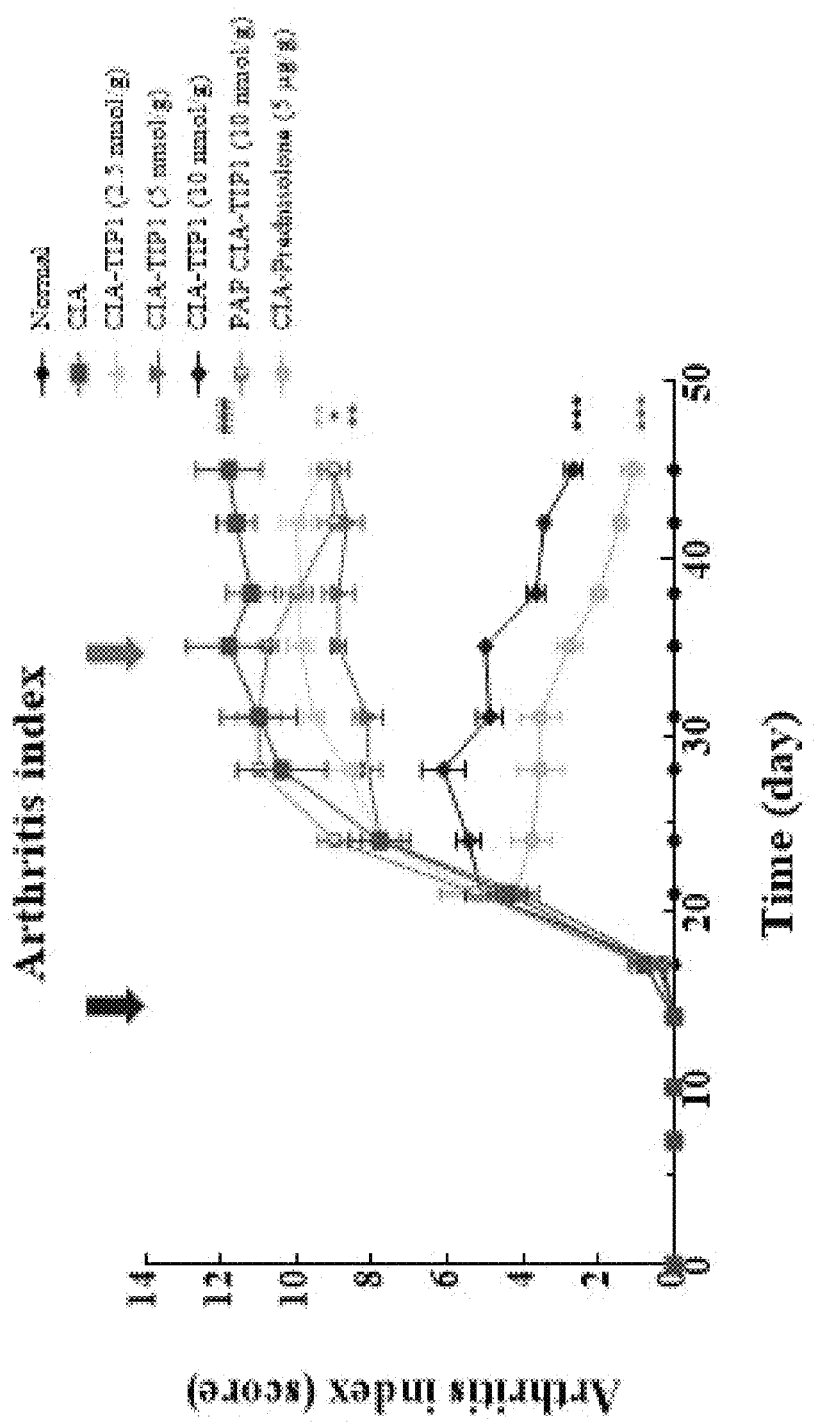

As illustrated in FIGS. 19(a) and 19(b), it was identified visually that the severely swollen foot exhibited by the CIA model was alleviated similarly to the normal mice in a case of being treated with TIP1. In addition, as illustrated in FIGS. 20(a)-20(d), it was identified that TIP1 inhibited body weight loss, squeaking and foot volume, and arthritis index increase, caused by induction of arthritis, to a level similar to that of prednisolone, a conventional therapeutic agent for arthritis.

In addition, DAB-1J mice for which arthritis had been induced through the CIA model were injected once daily with TIP1 and prednisolone for 30 days. Then, the mice were sacrificed on day 45 and joint tissues were sampled. Subsequently, 3D images and bone mineral density (BMD) of the joint tissues were analyzed through micro-computed tomography (Micro-CT). In addition, knee joint regions of the mice were subjected to hematoxylin and eosin (H&E) staining, and changes in synovial hyperplasia were observed in cartilage, subchondral bone, femur, tibia, and meniscus. The results are illustrated in FIGS. 21 and 22.

Figure 21:
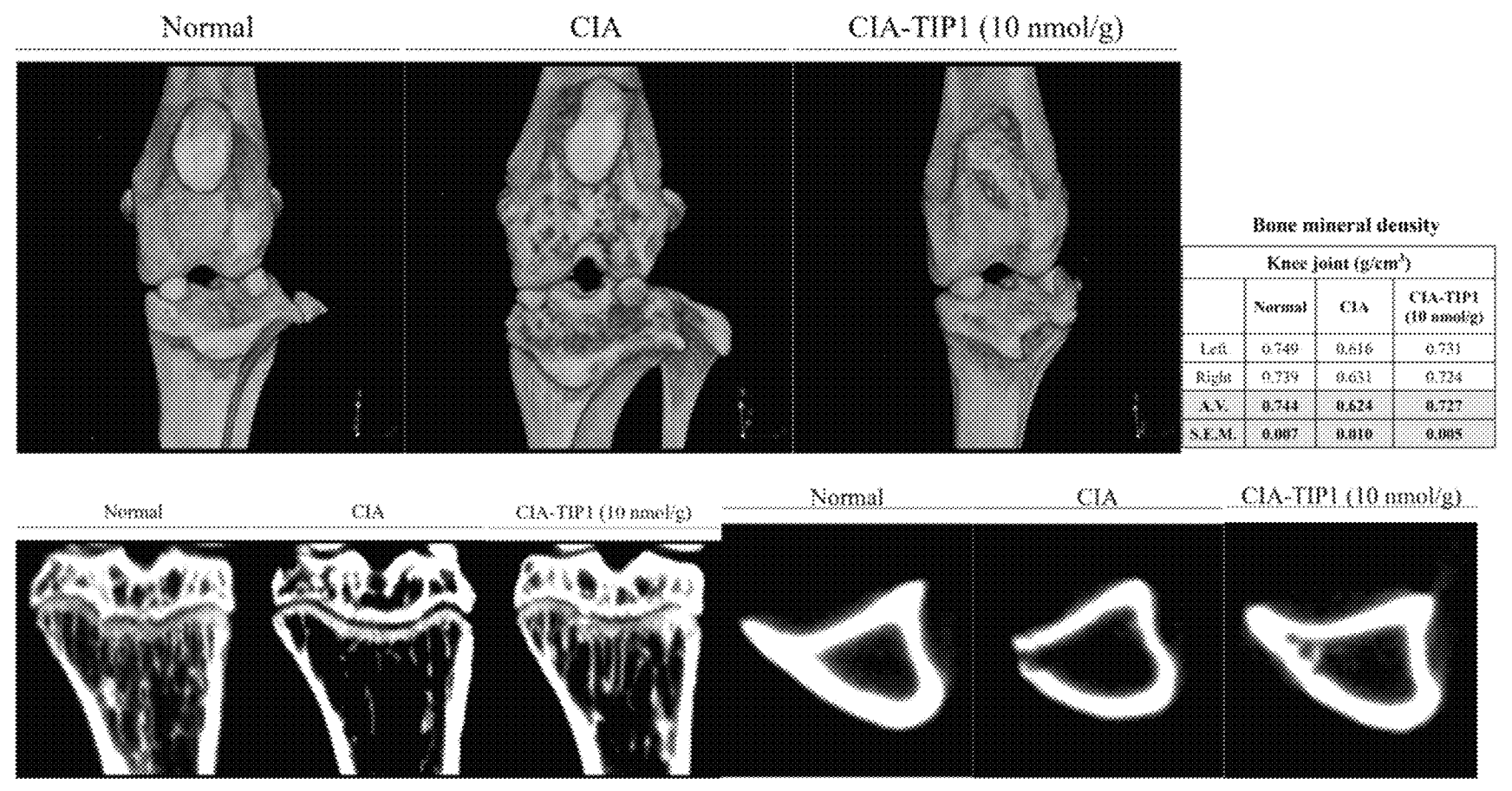
Figure 22:
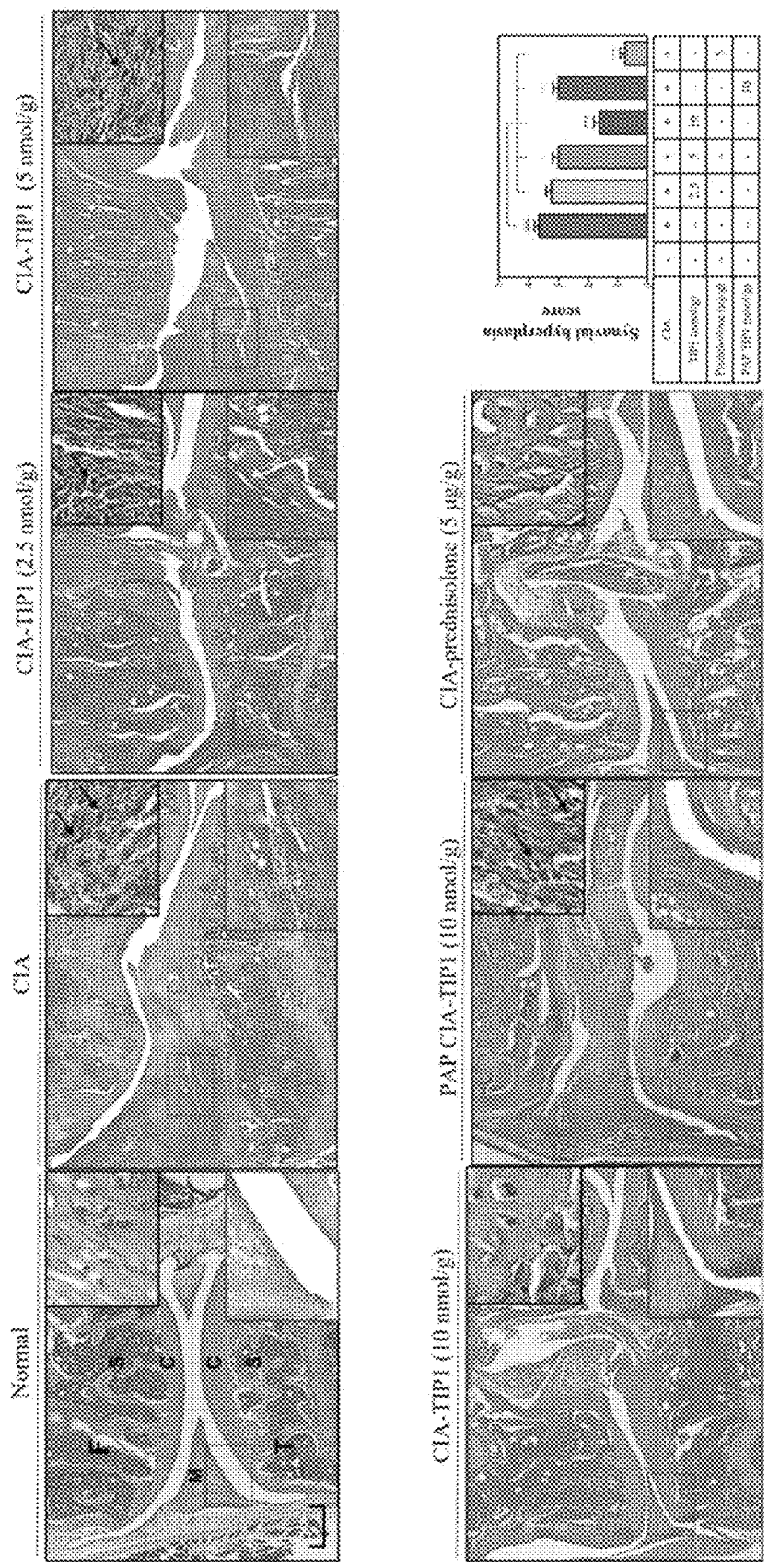
FIG. 22 illustrates results obtained by subjecting a CIA model of DAB-1J mice to treatment with TIP1, subjecting knee joint regions to hematoxylin and eosin (H&E) staining, and comparing a degree of treatment with prednisolone, a conventional therapeutic agent, indicating that TIP exhibits an excellent therapeutic effect.
Figure 23:
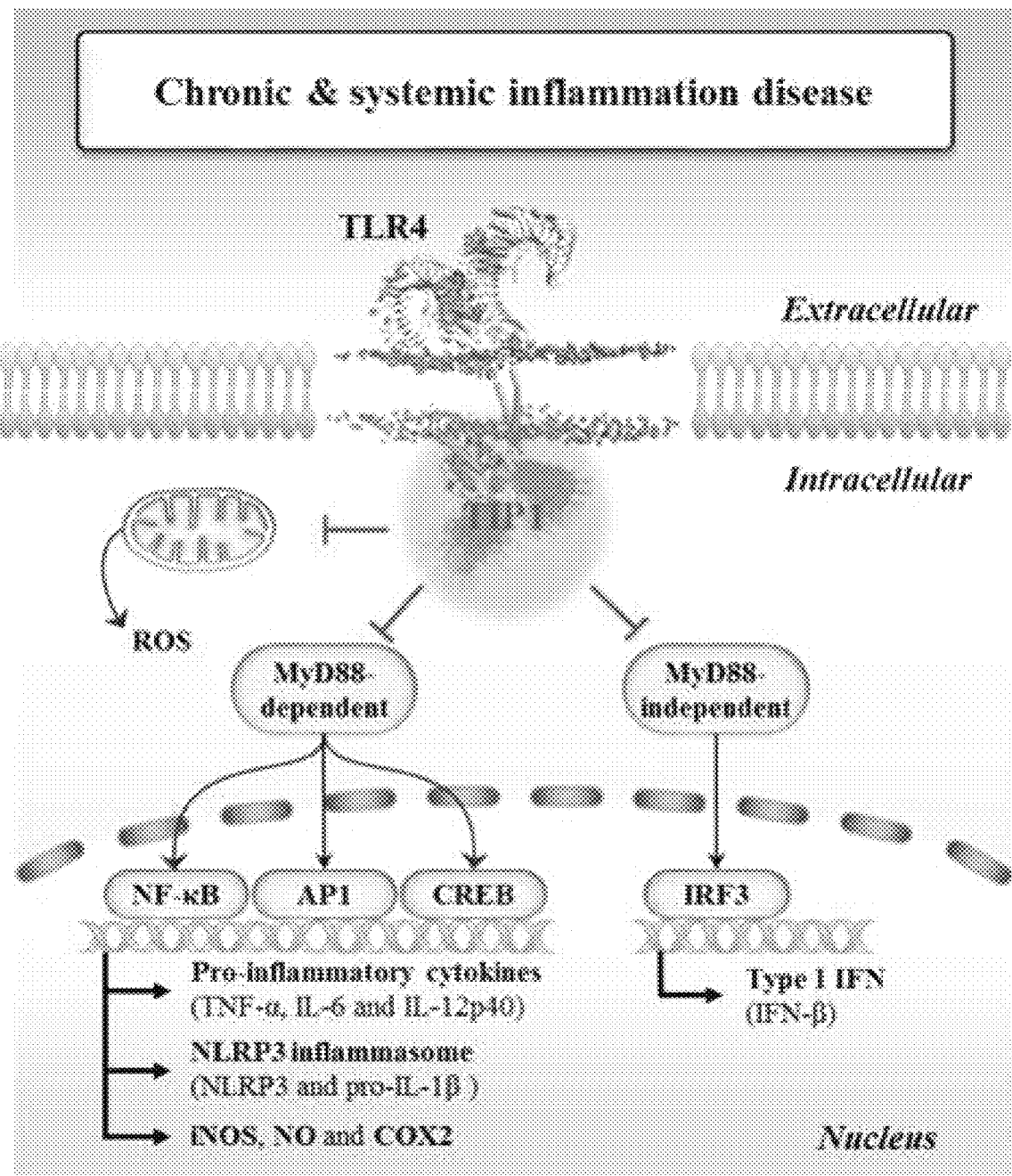
FIG. 23 schematically illustrates a signaling process induced by TLR4 and sites controlled by TIP1.

As illustrated in FIGS. 21 and 22, it was identified that in a case where treatment with TIP1 was performed, bones damaged by the CIA model were alleviated similarly to the normal mice, and histopathological modification in cartilage (C), subchondral bone (S), femur (F), tibia (T), and meniscus (M) was also decreased. From these results, it was identified that TIP1 according to the present invention effectively inhibits the TLR4 signaling pathway, and thus can be usefully used as a therapeutic agent for various acute or chronic inflammatory diseases, including rheumatoid arthritis.

The foregoing description of the present invention is provided for illustration. It will be understood by those skilled in the art that various changes and modifications can be easily made without departing from the technical spirit or essential features of the present invention. Therefore, it is to be understood that the above-described examples are illustrative in all aspects and not restrictive.

The invention claimed is:

1. A fusion peptide, in which a peptide consisting of the amino acid sequence of SEQ ID NO: 1 or SEQ ID NO: 2 is linked to the C-terminus of a cell-penetrating peptide.

2. The fusion peptide of claim 1, wherein the fusion peptide inhibits a signaling pathway mediated by a Toll-like receptor (TLR).

3. The fusion peptide of claim 2, wherein the fusion peptide inhibits a signaling pathway mediated by Toll-like receptor 4 (TLR4).

4. The fusion peptide of claim 2, wherein the fusion peptide inhibits a signaling pathway mediated by any one selected from the group consisting of Toll-like receptor 1/2 (TLR1/2), Toll-like receptor 2/6 (TLR2/6), Toll-like receptor 3 (TLR3), Toll-like receptor 7 (TLR7), Toll-like receptor 8 (TLR8), and Toll-like receptor 9 (TLR9).

5. The fusion peptide of claim 1, wherein blockage of a Toll-like receptor (TLR) signaling pathway by the fusion peptide results in inhibition of expression of tumor necrosis factor α (TNF-α), interleukin 6 (IL-6), or interferon β (IFN-β); inhibition of secretion of Nitric Oxide (NO) or reactive oxygen species (ROS); or inhibition of activity of nuclear factor kappa B (NF-κB), mitogen-activated protein kinase (MAPK), or NACHT, LRR and PYD domains-containing protein 3 (NLRP3) inflammasome.

6. The fusion peptide of claim 1, wherein the fusion peptide inhibits both MyD88-dependent and MyD88-independent Toll-like receptor 4 (TLR4) signaling pathways.

7. The fusion peptide of claim 1, wherein the fusion peptide consists of the amino acid sequence of SEQ ID NO: 3 or SEQ ID NO: 4.

8. A pharmaceutical composition comprising as an active ingredient:
a fusion peptide, in which a peptide consisting of the amino acid sequence of SEQ ID NO: 1 or SEQ ID NO: 2 is linked to the C-terminus of a cell-penetrating peptide; and
a pharmaceutically acceptable carrier.

9. The pharmaceutical composition of claim 8, wherein the fusion peptide consists of the amino acid sequence of SEQ ID NO: 3 or SEQ ID NO: 4.

10. A method for treating a Toll-like receptor (TLR) pathway-mediated disease, comprising:
administering to an individual in need thereof,
a fusion peptide in which a peptide consisting of the amino acid sequence of SEQ ID NO: 1 or SEQ ID NO: 2 is linked to the C-terminus of a cell-penetrating peptide,
wherein the TLR pathway-mediated disease is an autoimmune disease, an inflammatory disease, or a degenerative neurological disease.

11. The method of claim 10, wherein the autoimmune disease is at least one selected from the group consisting of insulin-dependent diabetes, multiple sclerosis, experimental autoimmune encephalomyelitis, rheumatoid arthritis, experimental autoimmune arthritis, myasthenia gravis, thyroiditis, experimental form of uveitis, Hashimoto thyroiditis, primary myxedema, thyroid poisoning, malignant anemia, autoimmune atrophic gastritis, Addison's disease, premature menopause, male infertility, childhood diabetes, Goodpasture syndrome, common pemphigus, pemphigoid, sympathetic ophthalmitis, lens uveitis, autoimmune hemolytic anemia, idiopathic leukocytopenia, primary biliary cirrhosis, chronic active hepatitis Hbs-ve, latent cirrhosis, ulcerative colitis, Sjogren's syndrome, scleroderma, Wegener's granulomatosis, polymyositis/skin myositis, discoid LE, and systemic lupus erythematosus.

12. The method of claim 10, wherein the inflammatory disease is at least one selected from the group consisting of asthma, eczema, psoriasis, allergy, rheumatoid arthritis, psoriatic arthritis, atopic dermatitis, acne, atopic rhinitis, pneumonia, allergic dermatitis, chronic sinusitis, contact dermatitis, seborrheic dermatitis, gastritis, gout, gouty arthritis, ulcer, chronic bronchitis, Crohn's disease, ulcerative colitis, ankylosing spondylitis, sepsis, vasculitis, bursitis, lupus, rheumatoid polymyalgia, temporal arteritis, multiple sclerosis, solid tumor, Alzheimer's disease, atherosclerosis, obesity, and viral infection.

13. The method of claim 10, wherein the degenerative neurological disease is at least one selected from the group consisting of Alzheimer's disease, frontal temporal dementia, Louis dementia, corticobasal degeneration, Parkinson's disease, multiple system atrophy, Huntington's disease, progressive supranuclear palsy, Lou Gehrig's disease, primary lateral sclerosis, and spinal muscular atrophy.

* * * * *